(12) United States Patent
Teague et al.

(10) Patent No.: US 6,300,115 B1
(45) Date of Patent: Oct. 9, 2001

(54) PULLULANASE EXPRESSION CONSTRUCTS CONTAINING α-AMYLASE PROMOTER AND LEADER SEQUENCES

(75) Inventors: W. Martin Teague; Phillip J. Brumm, both of Rockford; Larry N. Allen, Northfield; Igor A. Brikun, Forest Park, all of IL (US)

(73) Assignee: Enzyme Bio-Systems Ltd., Beloit, WI (US)

( * ) Notice: Subject to any disclaimer, the term of this patent is extended or adjusted under 35 U.S.C. 154(b) by 0 days.

(21) Appl. No.: 09/313,677

(22) Filed: May 18, 1999

Related U.S. Application Data
(60) Provisional application No. 60/122,065, filed on May 18, 1998.

(51) Int. Cl.[7] ................................................... C12N 9/44
(52) U.S. Cl. ................ 435/210; 435/320.1; 435/252.31; 435/254.11; 435/325; 435/419; 536/23.1; 536/23.2; 536/24.1; 536/23.4
(58) Field of Search ................... 536/23.1, 23.2, 536/24.1, 23.4; 435/320.1, 252.31, 254.11, 419, 325, 201, 210

(56) References Cited

U.S. PATENT DOCUMENTS

| | | |
|---|---|---|
| 4,469,791 | 9/1984 | Colson et al. . |
| 4,493,893 | 1/1985 | Mielenz et al. . |
| 4,598,048 * | 7/1986 | Diderichsen et al. ............ 435/172.3 |
| 4,604,355 * | 8/1986 | Outtrup .................................. 435/95 |
| 4,711,843 | 12/1987 | Chang . |
| 4,769,327 | 9/1988 | Stephens et al. . |
| 4,806,426 | 2/1989 | Colson et al. . |
| 5,055,403 | 10/1991 | Tomimura . |
| 5,480,801 * | 1/1996 | Wahleithner et al. ............ 435/254.3 |
| 5,514,576 | 5/1996 | Bower . |

FOREIGN PATENT DOCUMENTS

| | | |
|---|---|---|
| 0 057 976 A2 | 8/1982 | (EP) . |
| 0 405 283 A2 | 1/1991 | (EP) . |
| WO 93/10248 | 5/1993 | (WO) . |
| WO 93/10249 | 5/1993 | (WO) . |

OTHER PUBLICATIONS

Jorgensen et al. Cloning of a chromosomal alpha–amylase gene from *Bacillus stearothermophilus*. FEMS Microbiology Letters (1991) 77:271–276.*

Wallace et al. Oligonucleotide probes for the screening of recombinant DNA libraries. Methods in Enzymology (1987) 152:432–442.*

GenBank Accession No. AAA22233, (Apr. 1993).*

Matsudaira P. Limited N–terminal sequence analysis. Methods in Enzymology (1990) 182:602–613.*

Wozney JM. Using purified protein to clone its gene. Methods in Enzymology (1990) 182:738–751.*

GenBank Accession No. BSAMYLA1 (Mar. 1995).*

Aaronson et al., Cloning and expression of the thermostable alpha–amylase gene from *Bacillus stearothermophilus* in *Escheria coli*: a project in biotechnology for the teaching laboratory, *Biotechnology Education* (1992), 3(2):72–77.

Takase, Kenji, Effect of mutation of an amino acid residue near the catalytic site on the activity of *Bacillus stearothermophilus* α–amylase, *Eur. J. Biochem.* (1993), 211:899–902.

Vihinen et al., C–terminal truncations of a thermostable *Bacillus stearothermophilus* α–amylase, *Protein Engineering* (1994), 7(10):1255–1259.

Vihinen, Mauno and Mäntsälä, Pekka, Characterization of a Thermostable *Bacillus stearothermophilus* α–Amylase, *Biotechnology and Applied Biochemistry* (1990), 12:427–435.

Sen, Sribir and Oriel, Patrick, High Level Extracellular Secretion of Thermostable α–Amylase of *Bacillus stearothermophilus* in *Escherichia coli*, *Biotechnology Letters* (1989), 11:383–388.

Tsukagoshi et al., Efficient Synthesis and Secretion of a Thermophilic α–Amylase by Protein–Producing *Bacillus brevis* 47 carrying the *Bacillus stearothermophilus* Amylase Gene, *Journal of Bacteriology* (1985), 164(3):1182–1187.

Metz et al., Nucleotide sequence of an amylase gene from *Bacillus megaterium*, *Nucleic Acids Research* (1988), 16(11):5203.

Song et al., Molecular Cloning and Expression of α–Amylase Gene from *Bacillus stearothermophilus* in *Zymomonas mobilis* ZM4, *Journal of Microbiology and Biotechnology* (1992), 2(2):115–121.

Itoh et al., Artificial insertion of peptides detween signal peptide and mature protein: effect on secretion and processing of hybrid thermostable α–amylases in *Bacillus subtilis* and *Escherichia coli* cells, *Journal of General Microbiology* (1990), 136:1551–1558.

Mielenz, Jonathan R., *Bacillus stearothermophilus* contains a plasmid–borne gene for α–amylase, *Proc. Natl. Acad. Sci.* (1983), 80:5975–5979.

(List continued on next page.)

Primary Examiner—Ponnathapu Achutamurthy
Assistant Examiner—Kathleen Kerr
(74) Attorney, Agent, or Firm—Joseph T. Leone, Esq.; DeWitt Ross & Stevens S.C.

(57) ABSTRACT

Disclosed herein are DNA expression constructs containing an α-amylase promoter sequence derived from *Bacillus stearothermophilus*, an α-amylase leader sequence derived from *Bacillus stearothermophilus*, and a DNA sequence encoding a pullulanase derived from *Bacillus naganoensis*. Microbial hosts transformed to contain the expression constructs secret function pullulanases. Also disclosed is a process for making recombinant pullulanases utilizing the expression constructs and a recombinant pullulanase which can be produced in *Bacillus subtilis*.

25 Claims, 6 Drawing Sheets

OTHER PUBLICATIONS

Tomimura et al., Description of *Bacillus naganoensis* sp. nov., *International Journal of Systematic Bacteriology* (1990), 40(2):123–125.

Zeman, Nancy W. and McCrea, Jan M., Alpha–Amylase Production Using a Recombinant DNA Organism, *Cereal Foods World* (1985), 30(11):777–780.

Yamaguchi et al., Efficient Production of *Bacillus stearothermophilus* α–Amylase in *Bacillus brevis* by Altering Its Signal Peptide, *Biosci. Biotech. Biochem.* (1993), 57(8):1384–1386.

Cocconcelli et al., Single–stranded DNA plasmid, vector construction and cloning of *Bacillus stearothermophilus* α–amylase in Lactobacillus, *Res. Microbiol.* (1991), 142:643–652.

Suominen et al., Effects of signal peptide mutations on processing of *Bacillus stearothermophilus* α–amylase in *Escherichia coli, Microbiology* (1995), 141:649–654.

Nakajima et al., Nucleotide Sequence of the *Bacillus stearothermophilus* α–Amylase Gene, *Journal of Bacteriology* (Jul. 1985), 401–406.

Gray et al., Structural Genes Encoding the Thermophilic α–Amylases of *Bacillus stearothermophilus* and *Bacillus licheniformis, Journal of Bacteriology* (May 1986), 166:635–643.

Jorgensen et al., In Vivo genetic engineering: homologous recombination as a tool for plasmid construction, *Gene* (1990) 96:37–41.

ZAP Express™ Predigested Vector Kit and ZAP Express™ Predigested Gigapack Cloning Kits, BamHI/CIAP–Treated Instruction Manual, Catalog #239212 (ZAP Express™ Predigested Vector Kit).

Gigapack® III Gold Packaging Extract and Gigapack® III plus Packaging Extract, Catalog #200201 (Gigapack III Gold–4).

Original TA Cloning® Kit Instructions, Version C, Invitrogen Corporation, San Diego, CA 92121.

Appendix C *Genius System Product Listing*, User's Guide Version 3.0, Boehringer Mannheim Corporation, Indianapolis, IN 46250–0414.

* cited by examiner pCPC717 pEB200

PULLULANASE EXPRESSION CONSTRUCTS CONTAINING α-AMYLASE PROMOTER AND LEADER SEQUENCES

Priority is claimed to provisional patent application Ser. No. 60/122,065, filed May 18, 1998, and incorporated herein by reference.

FIELD OF THE INVENTION

The invention is directed to recombinant pullulanases, expression constructs which encode the enzymes and drive their expression and secretion in heterologous hosts, microbial hosts transformed to contain the expression constructs, and methods of manufacturing recombinant pullulanases using the transformed hosts.

DESCRIPTION OF THE PRIOR ART

Many high-molecular weight carbohydrates, such as starch, are polymers of glucose in which the glucosidic units are joined by α-1,6-glucosidic linkages or α-1,4-glucosidic linkages. Depolymerization of these carbohydrates into smaller subunits is a common industrial process in the manufacture of various syrups, food additives, and chemicals, such as high maltose syrup, dextrose, and the like. Depolymerization of these complex carbohydrates is conventionally accomplished by enzymatic hydrolysis.

For example, the conventional process for manufacturing d-glucose (dextrose) calls for a two-stage enzymatic hydrolysis of starch. In the first stage, the starch is liquefied by treating it with an α-amylase enzyme at a pH of between about 5.5 and 7.0 and at 104° C. or greater, whereby some of the α-1,4-glucosidic bonds in the starch are hydrolyzed. In the second stage, the liquefact then is treated with one or more enzymes to hydrolyze the α-1,6-glucosidic linkages and the remaining α-1,4-glucosidic linkages, thereby producing the primarily dextrose syrup. This hydrolysis (or "saccharification") is usually accomplished by the addition of a glucoamylase (1,4-α-D-glucan glycohydrolase; EC 3.2.1.3), an enzyme which hydrolyzes both α-1,4- and α-1,6-glucosidic linkages. The presence of α-1,6-glucosidic linkages in starch limits the maximum yield of dextrose in typical saccharifications because the formation of reversion products is much faster than the hydrolysis rate of the α-1,6-glucosidic linkages. Glucoamylase-containing products may be supplemented with other enzymes that increase the rate of α-1,6-glucosidic hydrolysis to maximize yield. Pullulanase (α-dextrin 6-glucanohydrolase; EC 3.2.1.41) is one such enzyme.

Because of the large demand for these hydrolyzing enzymes, much work has been done to identify novel enzymes and to optimize their functionality at the elevated temperatures and acidic conditions required in many commercial manufacturing protocols.

For an early discussion on the production of a recombinant α-amylase, see Zeman and McCrea (1985), *Cereal Foods World* 30(11):777–780.

Mielenz et al., U.S. Pat. No. 4,493,893 (issued Jan. 15, 1985), describe the cloning of a thermostable α-amylase from *Bacillus stearothermophilus* and expression of the α-amylase in *B. subtilis* and *Escherichia coli*.

Colson et al., U.S. Pat. No. 4,469,791 (issued Sep. 4, 1984) and U.S. Pat. No. 4,806,426 (issued Feb. 21, 1989), describe the production of α-amylases in genetically-engineered microbes. In these patents, a gene encoding an α-amylase was isolated from *B. megaterium* (NCIB No. 11568). Of particular note is the description of the plasmid pUB110 in the U.S. Pat. No. 4,806,426. The pUB110 plasmid can be used as a vector for insertion of the recombinant DNA sequences described below into bacterial hosts. As noted in the U.S. Pat. No. 4,806,426 the pUB110 plasmid has been found to be particularly stable and is replicated to high copy numbers in *B. subtilis* host cells.

Stephens et al., U.S. Pat. No. 4,769,327 (issued Sep. 6, 1988), describe vectors for the expression of fusion proteins in bacterial hosts. The vectors include promoter and leader sequences from the *B. licheniformis* α-amylase gene.

Tomimura, U.S. Pat. No. 5,055,403 (issued Oct. 8, 1991), describes a thermoduric and aciduric pullulanase enzyme isolated from *B. naganoensis*, ATCC No. 53909. This pullulanase retains at least 50% of its pullulan-hydrolyzing activity for 232 hours in aqueous solution at 60° C., pH 4.5. (See also Tomimura et al. (1990), *Int. J. Syst. Bacteriol.* 40(2):123–125.)

A series of mutant precursors of *B. stearothermophilus* α-amylase having altered leader peptides is described in Yamaguchi et al. (1993), *Biosci. Biotechnol. Biochem.* 57(8):1384–1386. The mutated peptides were then expressed in *B. brevis*. This study found that more efficient extracellular production of the *B. stearothermophilus* α-amylase in *B. brevis* was accomplished by introducing point mutations at positions between −6 and −4 of the leader sequence or by replacing the entire *B. stearothermophilus* α-amylase leader sequence with the leader sequence of the *B. brevis* middle wall protein.

A similar study on the effects of leader peptide mutations on the expression of recombinant *B. stearothermophilus* α-amylase in *E. coli* is presented in Suominen et al. (1995), *Microbiology* 141:649–654.

*B. stearothermophilus* α-amylase has also been cloned into other microbial hosts, such as lactobacilli. See Cocconcelli et al. (1991), *Res. Microbiol.* 142:643–652. Other references (largely cumulative to those discussed above) describing the cloning of α-amylases from *B. stearothermophilus* include Jørgensen et al. (1991), *FEMS Microbiol. Lett.* 77:271–276; Nakajima et al. (1985), *J. Bacteriol.* 163(1):401–406; and Gray et al. (1986), *J. Bacteriol.* 166 (2):635–643.

Jørgensen et al. (1990), *Gene* 96:37–41 describes a homologous in vivo recombination yielding a plasmid containing the leader sequence of a *B. licheniformis* α-amylase-encoding gene operationally linked to the structural gene of *B. stearothermophilus* α-amylase. When transformed into *B. subtilis*, this plasmid drives the expression of an α-amylase which is reported as being identical to the mature α-amylase secreted by wild-type *B. stearothermophilus*.

PCT Application WO 93/10249 describes a construct containing a *B. licheniformis* α-amylase promoter sequence operationally linked to the structural gene for *B. stearothermophilus* α-amylase. When transformed into *B. subtilis*, the construct drives the expression of functional *B. stearothermophilus* α-amylase.

U.S. Pat. No. 5,514,576 to Bower (issued May 7, 1996) describes the cloning of a rice pullulanase gene into a recombinant yeast host.

SUMMARY OF THE INVENTION

The immediate goal of the subject invention was to move the genetic information encoding the pullulanase described in U.S. Pat. No. 5,055,403 into a host organism which is better suited for commercial enzyme production. In so doing, it was discovered that constructs containing the native B. naganoensis promoter and leader sequences operationally linked to the pullulanase gene yielded negligible enzyme production. However, a construct containing the pullulanase coding sequence from B. naganoensis operationally linked to the promoter and leader sequences from the B. stearothermophilus α-amylase gene was found to drive high level production of the B. naganoensis pullulanase when transformed into a suitable bacterial host.

A first embodiment of the invention is drawn to a DNA expression construct comprising, in 5' to 3' order: an α-amylase promoter sequence derived from B. stearothermophilus, operationally linked to an α-amylase leader sequence derived from B. stearothermophilus, operationally linked to a DNA sequence encoding a pullulanase derived from B. naganoensis. The construct drives the expression and secretion of the encoded pullulanase in heterologous hosts.

A second embodiment of the invention is a DNA expression construct as described above which further comprises a DNA sequence encoding an N-terminal fragment of B. stearothermophilus α-amylase operationally disposed between the leader sequence and the DNA sequence encoding a pullulanase such that the expression construct expresses a fusion protein comprising N-terminal residues of B. stearothermophilus α-amylase bonded to a pullulanase. Here, the construct drives the expression of a fusion protein which retains its pullulan-hydrolyzing activity.

A third embodiment of the invention is directed to a DNA expression construct comprising, in 5' to 3' order: an α-amylase promoter sequence derived from B. stearothermophilus, operationally linked to an α-amylase leader sequence derived from B. stearothermophilus, operationally linked to a truncated DNA sequence encoding a fragment of a pullulanase derived from B. naganoensis. The construct drives the expression and secretion of the encoded truncated pullulanase in heterologous hosts.

A fourth embodiment of the invention is a process for manufacturing a recombinant pullulanase which comprises transforming a microbial host to contain an expression construct as described in the first or second embodiment and then culturing the transformed host on a suitable growth medium wherein the transformed host expresses the encoded pullulanase.

A fifth embodiment of the invention is a fusion protein having pullulanase activity as shown in SEQ. ID. NO: 16. This fusion protein is stably expressed and secreted in several heterologous hosts and has excellent pullulan-hydrolyzing activity (see Example 1).

The primary advantage of the invention is that the expression constructs described herein drive the expression and secretion of large amounts of a thermoduric and aciduric pullulanase in a transformed host. This pullulanase is an industrially valuable enzyme, finding use in the enzymatic hydrolysis of starch.

The invention is also advantageous in that it allows the pullulanase to be produced in large quantities in a well-characterized heterologous host such as B. subtilis, a bacteria known to produce large amounts of protein.

A still further advantage of the present invention is that it provides for the production of fusion proteins which retain their thermoduric and aciduric pullulanase activities, but can be produced from a wide range of heterologous hosts, including E. coli.

Yet another advantage of the invention is that truncated versions of the B. naganoensis pullulanase (i.e,. enzymes in which from 10 to 200 N-terminal amino acids have been deleted from the full-length pullulanase) retain their pullulanase activity and are secreted in significantly higher quantities than is the full-length pullulanase. While not being limited to any particular mechanism, it is believed that the cause of the increased yield of the truncated enzyme as compared to the full-length enzyme is a corresponding increase in plasmid stability. It is believed that the full-length pullulanase gene is unstable during growth of the host and undergoes partial deletion events, thereby lessening yield of the full-length enzyme. The truncated form of the pullulanase, however, apparently does not undergo this partial deletion, thereby resulting in higher yields of the truncated enzyme.

Further aims, objects, and advantages of the genetic constructs will appear more fully from a complete reading of the Detailed Description and attached claims.

DETAILED DESCRIPTION OF THE INVENTION

Definitions

Figure 1:
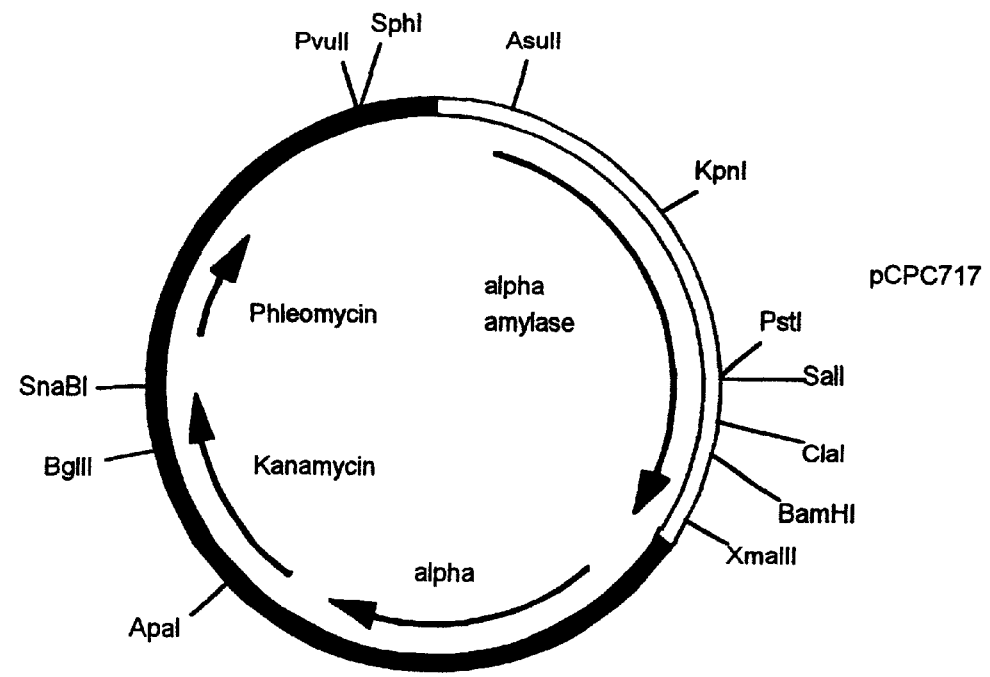
FIG. 1 is a schematic diagram depicting the introduction into pCPC717 (ATCC 39704) of a new KpnI restriction site, thereby yielding the plasmid pEB200.
Figure 1:
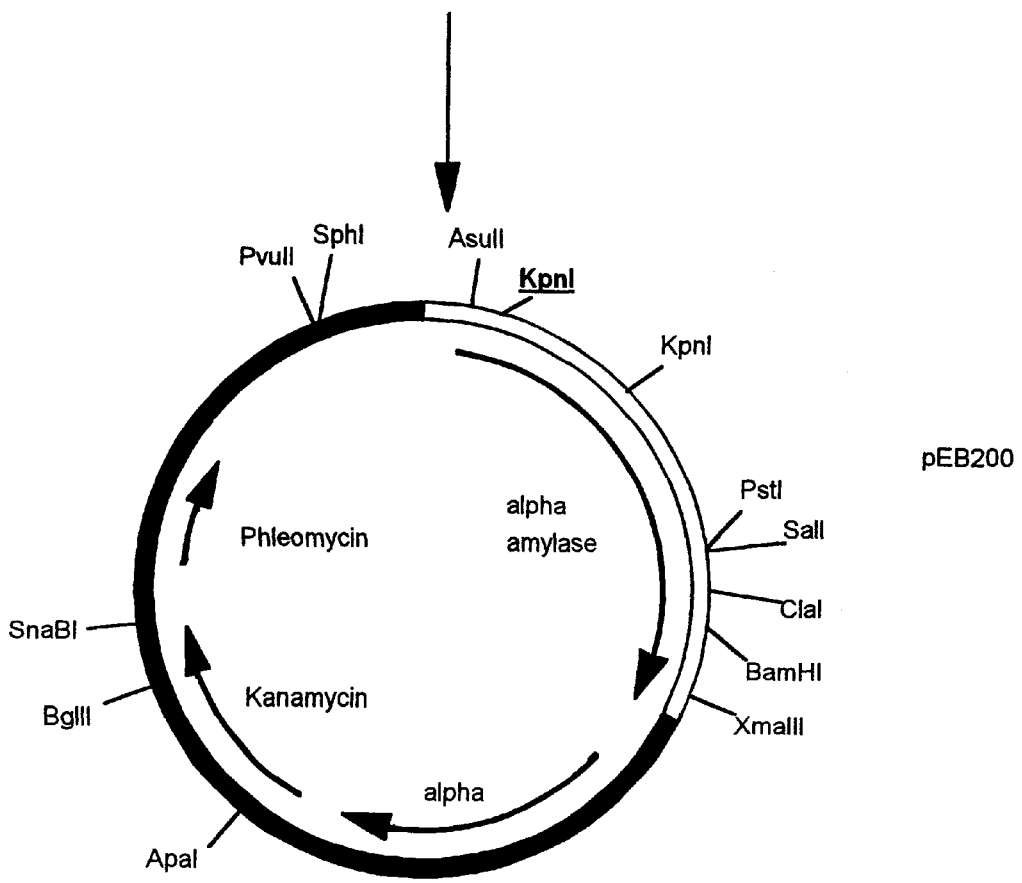

To provide a clear and consistent understanding of the specification, the following definitions are used herein.

Bacillus naganoensis—Bacteria having the characteristics of ATCC No. 53909, deposited with the American Type Culture Collection on May 18, 1989. (ATCC was formerly located in Rockville, Md.; it is now located at 10801 University Boulevard, Manassas, Va. 20110-2209.) See U.S. Pat. No. 5,055,403.

Bacillus stearothermophilus—Bacteria having the characteristics of ATCC Nos. 31195; 31196; 31197; 31198; 31199 and 31783, variants and mutants thereof, and submutants of the mutants.

Bacillus subtilis—Any strain of B. subtilis. Preferred strains are α-amylase-negative strains, such as strains having the characteristics of ATCC No. 31785 and Bacillus Genetic Stock Center No. 1A289 (Bacillus Genetic Stock Center, Ohio State University, Columbus, Ohio) or strains having the characteristics of B. subtilis NCIB 11,979, an asporogenic strain. (NCIB is the National Collection of Industrial Bacteria, Torry Research Station, P.O. Box 31, Aberdeen AB9 8DG, Scotland.)

Expression construct—A DNA construct containing at least one sub-sequence encoding a protein of interest which is operationally linked to one or more regulatory sub-sequences which drive expression of the encoded protein when the construct is transformed into a suitable host cell. Such constructs may also contain sub-sequences encoding means for selecting host cells transformed to contain the construct, such as sub-sequences which confer antibiotic resistance or dietary limitations to transformed cells.

Leader Peptide—An N-terminal extension of generally from about 10 to about 35 predominately hydrophobic amino acid residues. In bacteria, the leader peptide initiates a secretory pathway resulting in mobilization of the mature protein out of the cytoplasmic compartment. The leader peptide is cleaved from the mature protein chain post-translation and forms no part of the mature protein. "Leader peptide" is synonymous with the term "signal peptide."

Leader Sequence—A DNA sequence located between the transcription start site of an operon and the first structural gene. "Leader sequence" is synonymous with the term "signal sequence." The leader encodes a short peptide called the "leader peptide."

Operationally Linked—When referring to joined DNA sequences, "operationally linked" denotes that the sequences are in the same reading frame and upstream regulatory sequences will perform as such in relation to downstream structural sequences. DNA sequences which are operationally linked are not necessarily physically linked directly to one another but may be separated by intervening nucleotides which do not interfere with the operational relationship of the linked sequences.

Polymerase Chain Reaction (PCR)—A technique in which cycles of denaturation, annealing with a primer pair, and extension with DNA polymerase are used to generate a large number of copies of a desired polynucleotide sequence. See U.S. Pat. Nos. 4,683,195 and 4,683,202 for a description of the reaction.

Promoter—The DNA sequence site where RNA polymerase binds to the beginning of an operon. Once bound, the RNA polymerase travels along the DNA in the 5' to 3' direction and assembles the corresponding RNA sequences. While the promoter functions as the start signal for RNA synthesis, the promoter itself is not transcribed.

Pullulanases—Enzymes of the classification EC 3.2.1.41 which specifically cleave the α-1,6-glucosidic linkages of pullulan, starch, glycogen, and amylopectin.

Genetic Engineering

Many of the steps noted below for the manipulation of DNA, including digesting with restriction endonucleases, amplifying by PCR, hybridizing, ligating, separating and isolating by gel electrophoresis, transforming cells with heterologous DNA, selecting successful transformants, and the like, are well known and widely practiced by those skilled in the art and are not extensively elaborated upon herein. Unless otherwise noted, the DNA protocols utilized herein are described extensively in Sambrook, J.; Fritsch, E. F.; Maniatis, T. (1989), *Molecular Cloning: A Laboratory Manual;* Cold Spring Harbor Laboratory Press: New York, N.Y.

Host Cells

For industrial applications, the recombinant DNA described herein is incorporated into a host microbe. The host microbe may be any host amenable to transformation, including, but not limited to, microbes of the genera Saccharomyces, Bacillus, Aspergillus, Pichia, Kluyveromyces, Escherichia and the like. It is preferred that the host cell be a yeast or a bacterium, a bacterium being more preferred. The most preferred host is an asporogenic strain of *B. subtilis*.

Isolation of α-Amylase Promoter and Leader Sequences

The expression constructs described herein utilize promoter and leader sequences for an α-amylase structural gene derived from *B. stearothermophilus*. In the ultimate constructs, the α-amylase promoter and leader sequences are separated from their natural downstream coding sequences and operationally linked to a DNA sequence encoding a pullulanase enzyme, preferably a pullulanase derived from *B. naganoensis*. The construct is then transformed into a suitable host wherein the α-amylase promoter and leader sequences induce expression and secretion of the downstream pullulanase.

DNA encoding α-amylase promoter sequences and leader sequences is preferably isolated from plasmids found naturally in many strains of *B. stearothermophilus*. The preferred source is *B. stearothermophilus* ATCC No. 31783. The DNA can be isolated in the same fashion as described in U.S. Pat. No. 4,493,893.

As described in U.S. Pat. No. 4,493,893, total DNA from *B. stearothermophilus* is isolated by standard procedures (chloroform/phenol precipitation is preferred). Plasmid DNA is separated from total DNA by cesium chloride/ethidium bromide density gradient ultracentrifugation, in standard fashion.

The isolated plasmid DNA then digested with HindIII and mixed with similarly digested *E. coli* plasmid pBR327. The plasmid pBR327 contains the gene for ampicillin resistance which enables antibiotic selection of cells successfully transformed to contain the plasmid. The pBR327 plasmid is available commercially from Life Sciences, formerly Bethesda Research Laboratories, St. Petersburg, Fla. The co-mingled linear DNA sequences are then ligated using T4 DNA ligase to re-circularize the plasmids.

The plasmids are then transformed into suitable host cells (*E. coli* C600, ATCC No. 23724, is preferred) using any means known to the art, such as treating the cells with calcium chloride or by electroporation.

Successful transformants are selected by antibiotic resistance. Amylase activity is confirmed by transferring colonies to plates containing starch, allowing growth to occur, and then staining the plates with iodine. Undigested starch is stained blue by exposure to iodine. Colonies which express α-amylase are surrounded by distinct clear zones of digested starch.

Following this procedure, it was found that α-amylase-producing cells contained either a 6.0 kb or a 5.4 kb *B. stearothermophilus* insert containing the sequences required to express the α-amylase. Examination of the two inserts showed them to be identical with the exception of an additional 0.6 kb stretch of DNA at one end of the larger fragment. The plasmid containing the 6.0 kb insert, designated pCPC605 (ATCC 39708), was used for further manipulations.

Selective deletions of DNA from pCPC605 were used to localize the α-amylase gene to a smaller fragment of *B. stearothermophilus* DNA. Specifically, digesting pCPC605 with BamHI yielded pCPC611 (ATCC 39707). The pCPC611 plasmid was transformed into *E. coli* as described above and found to drive α-amylase production.

The pCPC611 plasmid was then partially digested with Sau 3A such that each plasmid was cut only once at one of more than 20 possible Sau 3A recognition sites. Separately, the *B. subtilis* plasmid pUB110 was digested with BamHI, mixed with the Sau 3A digested pCPC611, recircularized with T4 DNA ligase, and transformed into a *B. subtilis* host using standard procedures. This process yielded a number of differently-sized plasmids containing the α-amylase gene, depending upon the insertion site of pCPC611 into pUB110, the direction of insertion, and the amount of E. coli plasmid remaining in the recircularized plasmids.

A stable colony producing high yields of α-amylase was selected and designated pCPC704 (ATCC 39702). Analysis showed this plasmid to be one of the smallest found; almost all of the pBR327 E. coli DNA was deleted. This is not entirely unexpected because DNA from E. coli is unstable in B. subtilis and is often eliminated from a recombinant plasmid during transformation into B. subtilis. The pCPC704 plasmid contains all of pUB10 and the α-amylase gene of B. stearothermophilus.

The pCPC704 plasmid was further shortened by digestion with Bcl I and BamHI to yield pCPC712 (ATCC 39703). The last remaining E. coli DNA from pBR327 was then removed from the construct by digestion with Sau 3A followed by ligation. This yielded the plasmid designated pCPC717 (ATCC 39704) depicted in FIG. 1. The pCPC717 plasmid contains the α-amylase gene sequence and the sequences encoding the antibiotic resistance protein, kanamycin phosphotransferase, contained in the starting pUB110 plasmid. (If desired, the kanamycin resistance marker in pCPC717 can be eliminated by digestion with Sau 3A and BglII, thereby yielding pCPC 720, ATCC 39705.) It is preferred that the plasmid pCPC717, modified as described below, is used a source of the α-amylase promoter and leader sequences. The complete nucleotide base sequence of pCPC717 is presented in SEQ. ID. NO: 14.

Isolation of Pullulanase-Encoding DNA Sequences

The α-amylase promoter and leader sequences described above are ultimately separated from their natural downstream coding sequences and operationally linked to a DNA sequence encoding a pullulanase enzyme. Any DNA sequence encoding a pullulanase enzyme, derived from any source, can be used in the present invention. For sake of brevity only, the following is description of the preferred pullulanase enzyme, which is derived from B. naganoensis.

Preliminary attempts at cloning the B. naganoensis pullulanase gene suggested that active expression of this gene in E. coli, either on a plasmid or a phage, using the native B. naganoensis pullulanase promoter and leader sequences, is incompatible with E. coli cell physiology. Expression constructs containing the native pullulanase promoter, leader, and structural sequences from B. naganoensis were made in the same fashion as described below. All attempts to transform an E. coli host with such a construct were unsuccessful.

Inactive overlapping fragments of the pullulanase gene were cloned and sequenced (described below). This resulted in the availability of the entire DNA sequence of the pullulanase gene for cloning into a different host, such as B. subtilis. The DNA sequence of the B. naganoensis pullulanase and the amino acid sequence encoded thereby are presented together in SEQ. ID. NO: 1. The SEQ. ID. NO 2 depicts the amino acid sequence of the native, mature B. naganoensis pullulanase separate from its DNA sequence.

The N-terminal amino acids of the pullulanase enzyme, isolated as described in U.S. Pat. No. 5,055,403, were sequenced in conventional fashion along with several internal fragments generated by trypsin digestion. This information was used to design oligonucleotides for PCR amplification of a DNA probe directly from B. naganoensis chromosomal DNA.

PCR amplification of B. naganoensis chromosomal DNA using SEQ ID. NOS: 4 and 6 as primers yielded a 1.6 kb fragment which was cloned into the pCR™II plasmid (Invitrogen, San Diego, Calif.).

Amino acid sequence and initial oligonucleotide primers:
N-Terminus:
  Asp-Gly-Asn-Thr-Thr-Asn-Ile-Val-Val-His-Tyr-Phe-Arg-Pro (SEQ. ID. NO: 3)
  5'-GA(T/C)-GGN-AA(T/C)-ACN-ACN-AA(T/C)-AT(A/T/C)-GTN-GTN-CA(T/C)-TA-3' (SEQ. ID. NO: 4)
Tryptic Digest 1:
  Tyr-Asn-Val-Pro-Glu-Gly-Tyr-Gln (SEQ. ID. NO: 5)
  5'-TCC-TTC-AGG-GAC-GTT-GTA-3' (SEQ. ID. NO: 6)
Tryptic Digest 2:
  Asp-Ala-Glu-Ala-Ala-Ala-Gln-Pro-Ala-Val-Ser-Asn-Ala-Tyr-Leu-Asp-Ala (SEQ. ID. NO: 7)
  5'GTT-TCG-AAT-GCG-TAT-TTG-GAT-3' (SEQ. ID. NO: 8)
  5'-ATC-CAA-ATA-CGC-ATT-CGA-AAC-3' (SEQ. ID. NO: 9)

Sequence data from this clone resulted in the design of two more efficient PCR primers for the isolation of the 1.6 kb DNA probe.
  5'-ATG-TGG-CCG-GAG-AAC-GGT-GG3' (SEQ. ID. NO: 10)
  5'-GTT-GCG-AGG-GTC-ATA-ACC-CCA-AT-3' (SEQ. ID. NO: 11)

Sequencing the Bacillus naganoensis Pullulanase Gene

B. naganoensis chromosomal DNA was isolated in standard fashion and digested with the restriction enzyme Sau 3A, mixed with predigested "ZAP Express"™ BamHI/CIAP-treated vector (Stratagene, La Jolla, Calif., catalog no. 239,212) and ligated. The ligated DNA was encapsidated in vitro (Stratagene, catalog no. 200201) resulting in the construction of biologically-active phage particles. The phage particles were used to infect E. coli XL1-Blue MRF' (Δ(mcrA)183 Δ(mcrCB-hsdSMR-mrr)173 endA1 supE44 thi-1 recA1 gyrA96 relA1 lac {F' proAB lacl$^q$ZΔM15 Tn10 (Tet$^r$)}) (Stratagene) which was then grown on LB agar plates. The phage plaques were transferred to HATF membranes (Millipore Corporation, Marlborough, Mass.) and screened by hybridization to the 1.6 kb digoxigenin-labeled (Boehringer Mannheim, Indianapolis, Ind.) DNA probe. Positive plaques were picked and purified by successive rounds of infection, plating, and hybridization. Following purification, DNA was prepared from each of the positive phages and the sequences of the inserts were determined by DNA sequencing (Sanger's method).

Insertion of B. naganoensis Pullulanase Gene into pCR™II

Using the known N-terminal and C-terminal sequence of the pullulanase enzyme, DNA of the mature pullulanase gene is generated by PCR directly from B. naganoensis chromosomal DNA using two oligonucleotides:
  5'-GGG-GGT-ACC-GAT-GGG-AAC-ACC-ACA-AAC-ATC-G-3' (SEQ. ID. NO: 12)
  5'-GGA-TCC-TAA-GTT-CAT-TTA-GGT-CGA-TGA-AGG-3' (SEQ. ID. NO: 13)

Figure 2:
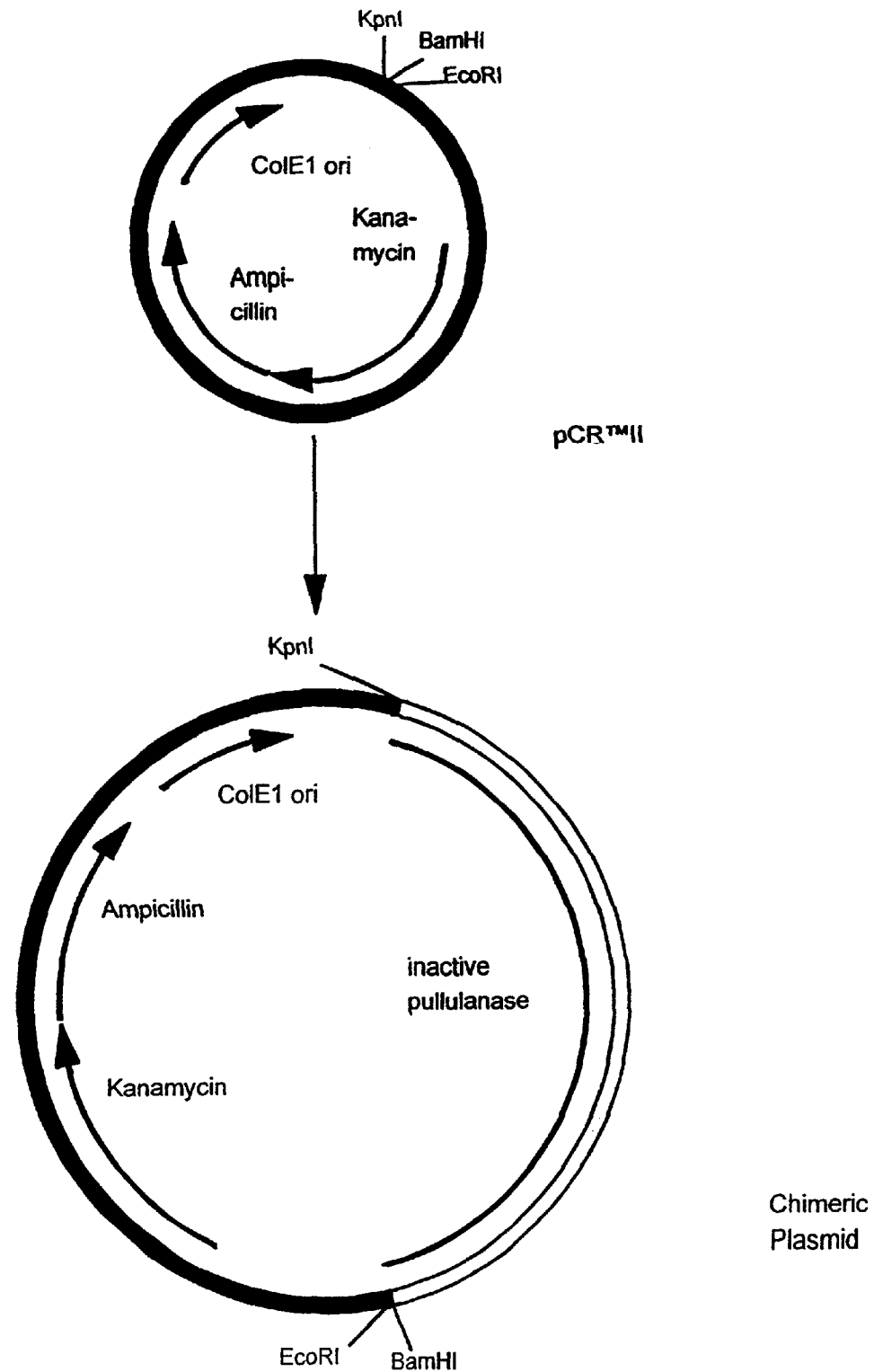
FIG. 2 is a schematic diagram depicting the introduction of the coding sequence of B. naganoensis pullulanase into the unique KpnI restriction site of the commercially-available plasmid pCR™II to yield the chimera plasmid or "chimera."

Referring now to FIG. 2, the primers were designed so that the PCR product would contain a KpnI site at the 5' end and a BamHI site at the 3' end. The PCR fragment was gel purified and cloned onto the pCR™II plasmid, which has unique sites for KpnI and BamHI. The pCR™II starting plasmid is depicted schematically in the top construct of FIG. 2. The ligation mixture was transformed into the E. coli K-12 derivative INVαF' (Invitrogen). The resulting chimeric plasmid contains the pCR™II plasmid along with the mature pullulanase gene minus promoter and leader sequences. This construct, designated the "Chimeric Plasmid" is presented schematically in the bottom construct of FIG. 2.

Operationally Linking the Pullulanase Gene to the α-Amylase Promoter and Leader Sequences A large scale plasmid DNA preparation was made from a positive pCR™II clone. This plasmid DNA was digested with KpnI and BamHI and the *B. naganoensis* fragment was subcloned into the pEB200 plasmid (SEQ. ID. NO: 15). The pEB200 plasmid is identical to the pCPC717 plasmid described above, with the exception of a single base pair change (GGCACC to GGTACC) near the 3' end of the α-amylase leader sequence. (Compare base pair 480 of SEQ. ID. NO: 14 with base pair 480 of SEQ. ID. NO: 15.) The single base pair change causes no change in the encoded amino acid, but creates a KpnI site. The introduction of the KpnI site into pCPC717 to yield pEB200 is depicted in FIG. 1. (The new KpnI site is present at the 1:00 o'clock position of the pEB200 plasmid).

Figure 3:
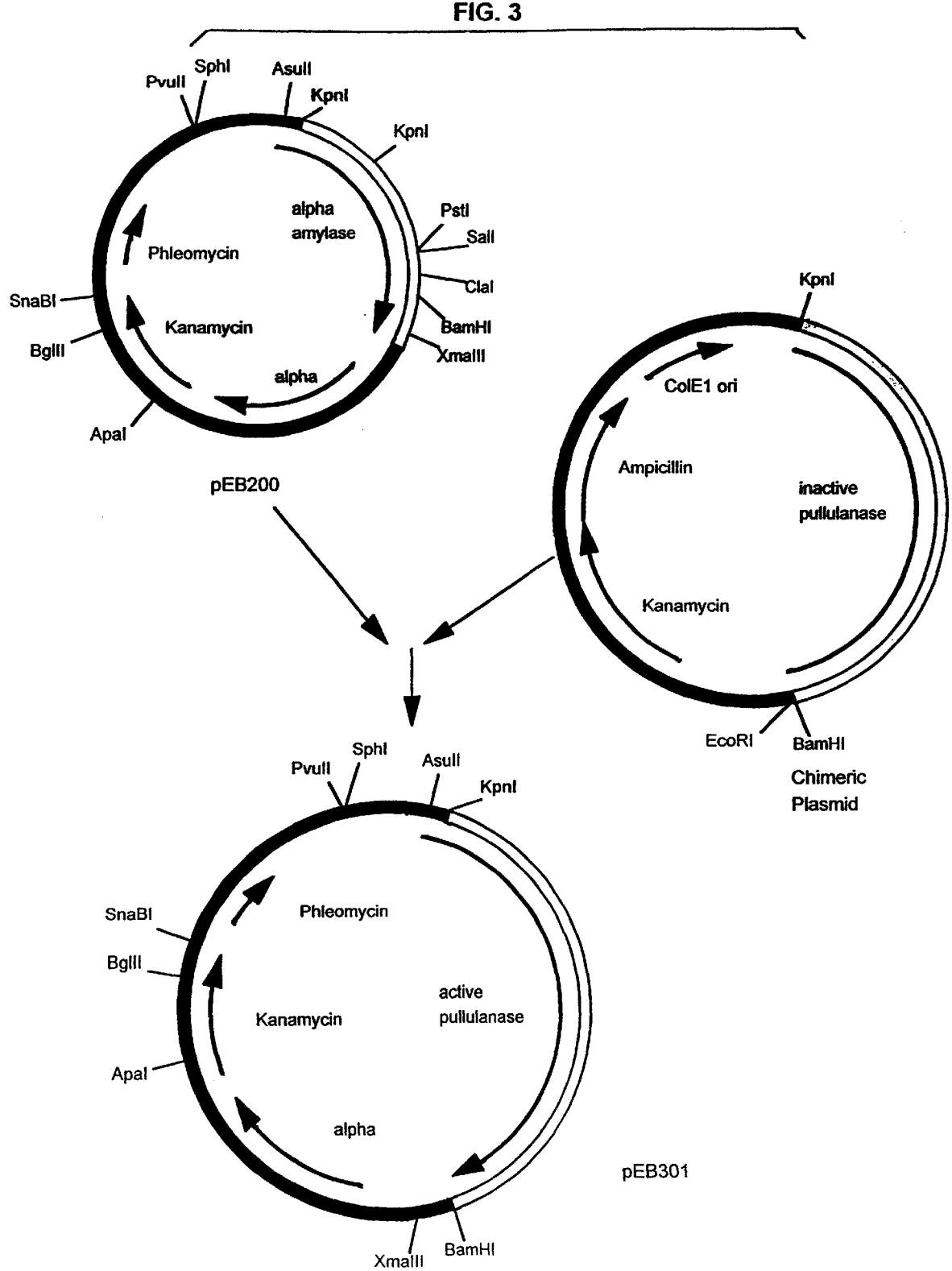
FIG. 3 is a schematic diagram depicting the insertion of the coding sequence of B. naganoensis pullulanase into pEB200 in place of the coding sequence for B. stearothermophilus α-amylase to yield pEB301.

Referring now to FIG. 3, the pEB200 plasmid was cut with KpnI and BamHI and ligated to the similarly digested "Chimeric Plasmid" containing the pullulanase coding region. The new plasmid, designated pEB301 in FIG. 3, contains the *B. stearothermophilus* α-amylase promoter sequence, the *B. stearothermophilus* α-amylase leader sequence, the first seven N-terminal amino acids of the mature *B. stearothermophilus* α-amylase enzyme itself, and the entire mature pullulanase coding sequence from *B. naganoensis*. The SEQ. ID. NO: 16 depicts the nucleotide base sequence of pEB301 and the transcribed amino acid sequence of both the leader sequence (nucleotides 361 to 462 of SEQ. ID. NO: 16) and the expressed pullulanase (nucleotides 463 to 3261 of SEQ. ID. NO: 16). The SEQ. ID. NO: 17 depicts the amino acid sequence of the *B. stearothermophilus* α-amylase leader sequence linked to the expressed pullulanase protein. The SEQ. ID. NO: 18 presents the DNA coding region of just the expressed pullulanase, and SEQ. ID. NO: 19 is the amino acid sequence of the fusion protein expressed by the pEB301 construct.

Transforming *B. subtilis* with pEB301

The plasmid pEB301 was transformed into *B. subtilis* strain B1-109 using the conventional competent cell method, selected by kanamycin resistance (40 μg/ml), and screened for halos on double strength LB, 1% amylopectin 1.5% agar plates. Plasmid DNA was isolated from a transformant and the plasmid retransformed into strain B1-163, a low protease derivative of strain B1-109. Cultures of this transformant produced about 42 U/ml of pullulanase in 46 hours under the conditions described in Example 1.

Construction of a Truncated Pullulanase

In this construct, 318 base pairs were removed from the coding region of pEB301, thereby yielding a construct which drives the expression of a pullulanase fragment which is 106 amino acid residues shorter than the pullulanase expressed by pEB301. This construct has been designated pEB303 and is illustrated in SEQ. ID. NO: 20. The truncated pullulanase expressed by pEB303 when transformed into a suitable host is shown in SEQ.ID. NO: 21

To remove the unwanted portions of pEB301, primers were generated which would introduce useful restriction sites. For the C-terminal primer, SEQ. ID. NO: 13, described above, was used:

5'-GGA-TCC-TAA-GTT-CAT-TTA-GGT-CGA-TGA-AGG-3' (SEQ. ID. NO: 13).

This primer contains a BamH1 restriction site (underlined).

For the new N-terminal of the construct, a primer containing a 5' Kpn1 restriction site (underlined) was used:

5'-GGG-GGT-ACC-GCA-CAA-CCT-GCT-GTA-AGT-AAC-GC-3' (SEQ. ID. NO: 22).

Figure 5:
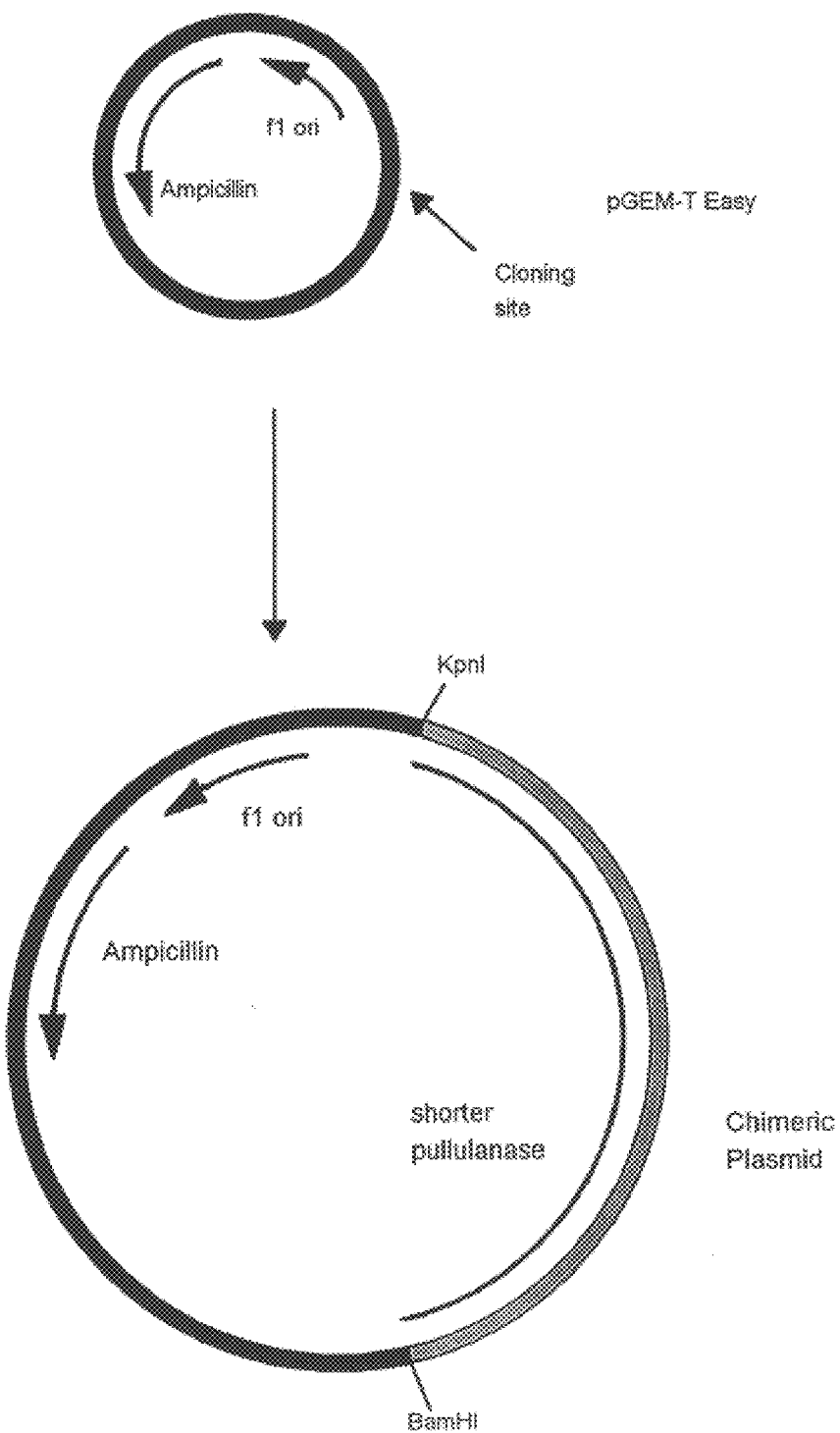
FIG. 5 is a schematic diagram depicting the generation of a truncated fragment of DNA encoding B. naganoensis pullulanase from pEB301 and ligating the truncated fragment into a plasmid.

PCR amplification products of pEB301 are cloned into pGEM-T-Easy (Promega) and transformed in *E. coli* INVαF'. See FIG. 5 for a schematic representation of this step.

Cloning the shortened pullulanase into *B. subtilis* was accomplished by first selecting a clone shown to contain the truncated construct by miniprep. The plasmid DNA was then digested with Kpn1 and BamH1 to free the truncated sequence and the pullulanase fragment was gel purified.

Plasmid pEB200 was then also digested with Kpn1 and BamH1 and the larger pEB200 fragment (containing the plasmid replication region, the *B. stearotherophilus* α-amylase promoter, leader, and the first seven amino acids of the mature protein) was gel purified.

Figure 6:
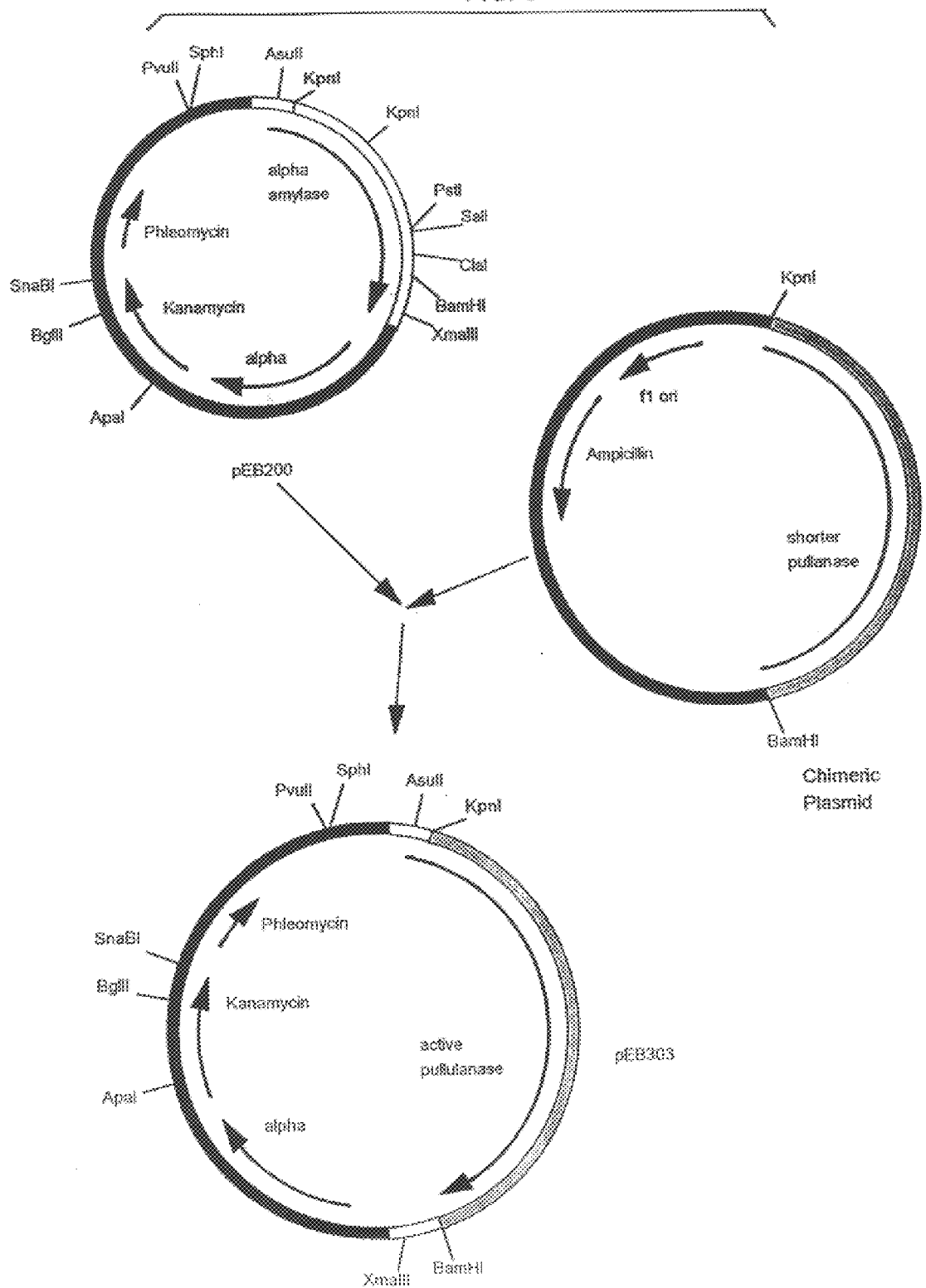
FIG. 6 is a schematic diagram depicting the generation of pEB303.

Ligation of the pEB200 fragment to the truncated pullulanase fragment generates pEB303. See FIG. 6. The pEB303 plasmid is isolated from a positive transformant and then used to transform *B. subtilis* strain B1-163, as noted hereinabove.

The pEB303 plasmid was also isolated from *B. subtilis* and sequenced to confirm the junction between the *B. stearothermophilus* DNA and the new N-terminus of the truncated pullulanase gene.

The truncated pullulanase enzyme was isolated and purified and subjected to N-terminal protein sequencing. The protein leader is removed at the same position as in the full-length pullulanase encoded by pEB301. See SEQ. ID. NO: 20 for the amino acid sequence of the truncated pullulanase.

N-Terminal Sequence of the Recombinant Pullulanase Gene

The recombinant pullulanase protein expressed by pEB301 was purified and the N-terminal sequence determined by conventional means. The protein is processed at the same position as the *B. stearothermophilus* α-amylase leader. The new N-terminus of the pullulanase protein is: Ala-Ala-Pro-Phe-Asn-Gly-Thr-Asp-Gly-Asn (residues 1 through 10 of SEQ. ID. NO: 19). The underlined amino acids are the first seven amino acids of mature *B. stearothermophilus* α-amylase followed by the mature pullulanase protein sequence. The amino acid sequence of the entire expressed fusion protein is shown in SEQ. ID. NO: 19. The fusion does not effect any of the physical characteristics of the expressed pullulanase but does stabilize expression and controls the lethality previously noted in all constructs containing the native pullulanase leader sequence.

EXAMPLES

The following Examples are provided solely to aid in a more complete understanding of the invention described and claimed herein. The Examples do not limit the scope of the invention in any fashion.

Example 1

Production of Recombinant Pullulanase

A culture of *B. subtilis* was transformed via the conventional competent cell method to contain pEB301 and was then cultured under the following conditions:

Cell culture medium
2.0% Difco (Detroit, Mich., USA) tryptone
1.0% Difco yeast extract
2.0% sodium chloride
2.0% Corn Products International (Summit-Argo, Ill., USA) "GLOBE 1910"-brand maltodextrin
20 μg/ml kanamycin sulfate The pH of the medium was adjusted to 6.0 and the cell cultures grown in shake flasks at 37° C. with agitation at 200 rpm for 43 hours.

The cell culture medium was assayed for pullulanase activity by the release of reducing sugar from pullulan in the presence of enzyme. A solution (0.5 ml) of 1.0% pullulan (Sigma P4516, Sigma Chemical Co., St. Louis, Mo.) in 50 mM acetic acid-sodium acetate buffer, pH 5.0 was incubated for 10 minutes at 60° C. in 16×125 mm culture tubes. An equal volume of sample (which contained from 0.02 to 0.1 U/ml of pullulanase activity) or buffer was added to the pullulan solution, and the resulting solution was incubated for 15 minutes at 60° C. The tubes were removed from the incubation, and enzyme action was terminated by adding 0.5 ml of 1 M sodium carbonate, followed by mixing. Distilled water (1.0 ml) and alkaline ferricyanide solution (2.5 ml of a solution containing 1.170 g/liter of potassium ferricyanide and 19.5 g/liter of anhydrous sodium carbonate) were added to each tube, and the tubes were again mixed. The tubes were then incubated at 100° C. for 7 minutes, cooled to room temperature, and the absorbance of each tube was measured at 373 nm. The absorbance was corrected for non-specific absorbance produced by the substrate and sample by subtracting the absorbance values of tubes carried through the assay which contained either substrate and buffer only or sample and buffer only. A standard curve of absorbance at 373 nm versus micromoles of reducing sugar was prepared using 1.0 ml samples of between 0.2 micromoles and 1.0 micromoles of glucose carried through the above procedure starting at the point of addition of 0.5 ml of 1 M sodium carbonate. The absorbance of enzyme-containing samples was then converted to micromoles of reducing sugar by comparing the corrected absorbance values for the samples to the absorbance values obtained for the standard glucose solutions. One (1) unit of pullulanase activity is defined as the amount of enzyme required to produce 1 micromoles of reducing sugar (as glucose) per minute at 60° C. and pH 5.0.

The cell culture medium of the *B. subtilis* transformed to contain pEB301 was found to have 42 U/ml of pullulanase activity as measured by the above-described assay.

Example 2
Isolation of Recombinant Pullulanase

Recombinant pullulanase from cell culture media produced as described in Example 1 was isolated as follows:

We adjusted about 250 ml of 700 U/ml pullulanase to 1 M $(NH_4)_2SO_4$ with 4 M salt and passed it through a laboratory column containing about 100 ml of phenyl sepharose (Phenyl Sepharose 6 Fast Flow; Pharmacia Biotech, Piscataway, N.J.) in 1 M $(NH_4)_2SO_4$. The material then was washed with 0.6 M $(NH_4)_2SO_4$ in 50 mM acetate buffer (pH 5.8), and the enzyme eluted with a 400 ml, reverse gradient from 0.6 M to 0.0 M $(NH_4)_2SO_4$ in 50 mM acetate buffer (pH 5.8). The pullulanase eluted as a broad peak in the final quarter of the gradient. We concentrated the pullulanase to 8 ml by ultrafiltration (YM10 membrane; Amicon, Beverly, Mass.), and further purifed it, in 4-ml aliquots, by size exclusion chromatography (HiPrep 26/60 Sephacryl S-100 HR; Pharmacia) in 50 mM acetate buffer (pH 5.8). In the last step, we applied the pullulanase to a column containing 4 ml of Maltotriose-Agarose (M2535; Sigma Chemical, St. Louis, Mo.) equilibrated in 50 mM acetate buffer (pH 5.8) and washed the material sequentially with 50 ml of equilibration buffer and 50 ml of 1 M NaCl in equilibration buffer. We then eluted the enzyme with 50 ml of 10% maltotriose in equilibration buffer.

The method purifies pullulanase from either the native source or the recombinant source to homogeneity as determined by SDS-PAGE (see Example 3). The native *B. naganoensis* pullulanase average specific activity of 948 U/mg (six events) was found to be equivalent to the average specific activity of 911 U/mg (two events) for the recombinant pullulanase from *B. subtilis*.

The alkaline ferricyanide method, described in Example 1, was used to measure enzyme activity and a Coomassie method, "Instructions for Coomassie Plus Protein Assay Reagent," and reagent (Pierce Chemical Company) to measure protein.

Example 3
Comparison of Recombinant Pullulanase to Native Pullulanase

We examined the general characteristics of the recombinant pullulanase produced by *B. subtilis* and compared them to the native pullulanase from *B. naganoensis*. In each case, the comparisons were performed using the pure native enzyme versus the pure recombinant enzyme. In fact, the pullulanase from either source can be isolated using the methods outlined in Example 2. The similarity of behavior during purification is one indicator that the recombinant protein is identical to the native protein.

Non-denaturing, Polyacrylamide Gel Electrophoresis (PAGE):

Recombinant and native pullulanase were run in parallel lanes in a Novex™ precast 10% tris-glycine acrylamide gel (Novel Experimental Technology, Inc., San Diego, Calif.). The results indicate that each enzyme has the same relative mobility. The electrophoresis was performed as described in "Novex™ Precast Gel Instructions" and the gel visualized by staining using a slight modification of the method described in "Specific Detection of Pullulanase Type I in Polyacrylamide Gels", Kim, C. H. (1994), *FEMS Microbiol. Lett.* 116:327–332 (we substituted 10% Globe 1910 maltodextrin (Corn Products) for soluble starch, which reduced the background color). The visualized enzymes had the same mobility.

Protein was then visualized using Coomassie stain following the protocol supplied with Novex™ Gel-Clear™ Destaining Solution (Novel Experimental Technology, Inc.). There was only one type of protein in each case, and the mobility indicated by the protein visualization method corresponded to the mobility indicated by the activity visualization method.

Figure 4:
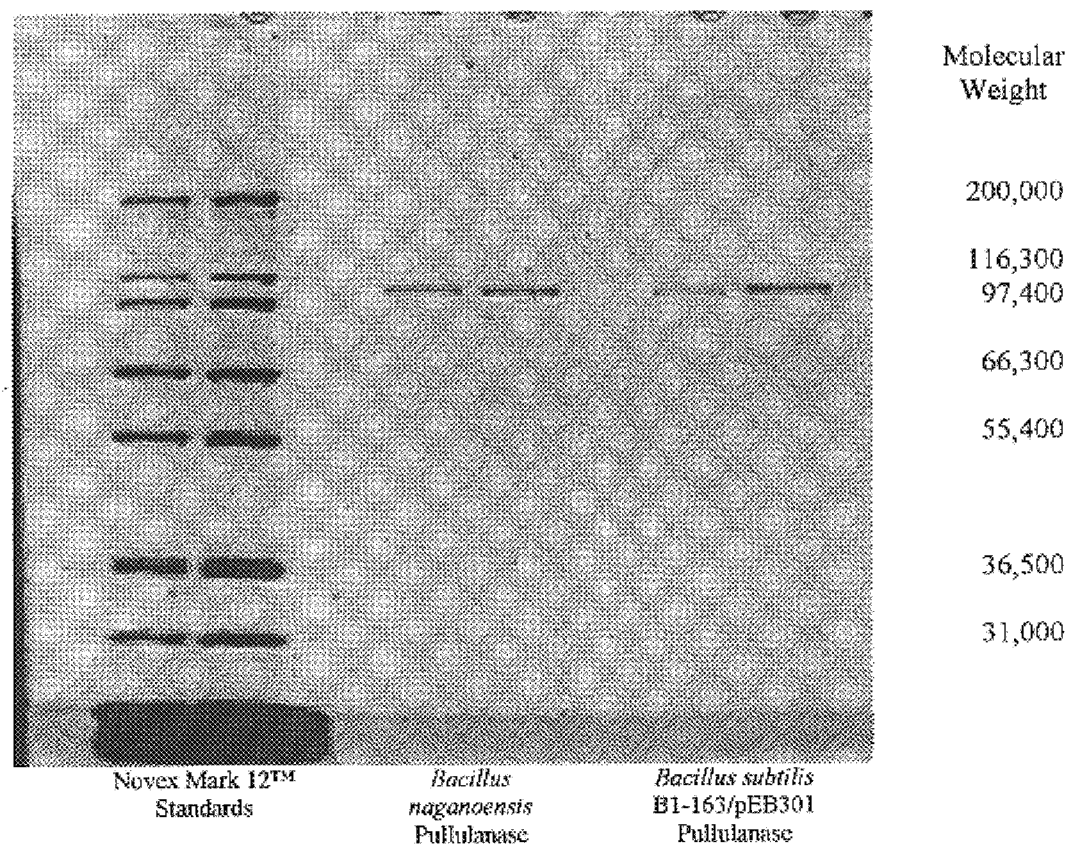
FIG. 4 is an SDS-PAGE gel comparing the recombinant pullulanase according to the present invention with native pullulanase from B. naganoensis.

Analyses by PAGE in sodium dodecyl-sulfate (SDS) indicates that the subunit molecular weight, which is related to the mobility, is about 109,000 for each of the proteins (see FIG. 4). To generate FIG. 4, we used the same materials and methods as described above. We determined the subunit molecular weight by comparison of the protein mobility, visualized with Coomassie as above, to that obtained using pure proteins of known subunit molecular weight (Novex™ Mark12™ protein standards; Novel Experimental Technology, Inc.) using the procedure as described in *Gel Electrophoresis of Proteins, A Practical Approach*, B. D. Hames and D. Rickwood, ed., IRL Press, Oxford, 1990, pp. 16–20. The molecular weight for the native pullulanase computed from the DNA sequence for *B. naganoensis* pullulanase is 101,343 while that for the recombinant pullulanase from *B. subtilis* is 102,000.

Isoelectric Point:

The isoelectric points for the native and recombinant pullulanases are both about 4.5. The isoelectric points were determined using Novex IEF 3–7 gels (Novel Experimental Technology, Inc.) while following the procedures described in "Novex Precast Gel Instructions." The isoelectric points were determined by comparison of position with that for proteins of known isoelectric point (IEF Mix 3.6–6.6, Sigma I 8012; Sigma Chemical Co.). The value is close to the computed pI of 4.6 for each.

Ouchterlony Double Diffusion:

It was also verified that the antigenic determinant of the recombinant pullulanase produced in *B. subtilis* is the same as that from the native *B. naganoensis* pullulanase. Ouchterlony double diffusions were performed with rabbit antiserum to pure *B. naganoensis* pullulanase using precast, double diffusion plates (ICN 64-275-1, ICN Pharmaceuticals, Inc., Costa Mesa, Calif.) and the results analyzed according to the method described in *Immunochemical Techniques for the Identification and Estimation of Macromolecules*, J. Clausen, Elsevier, 1988.

A summary of the above comparisons is presented in Table 1:

TABLE 1

| Method | *B. naganoensis* Pullulanase | *B. subtilis* Pullulanase |
|---|---|---|
| Specific Activity (U/mg protein) | 948 | 911 |
| Antigenicity | single precipitin line | single precipitin line |
| Isoelectric Point (pI) | 4.5 | 4.5 |
| Molecular Weight, SDS-PAGE | 109,000 | 109,000 |
| Appearance | clear, colorless solution | clear, colorless solution |
| Subunits | single | single |

Example 4
Comparison of Production of Full-Length Pullulanase and Truncated Pullulanase For this Example, the following fermentation conditions were employed:

The shake flask medium for seed development contained the following (g/L)

| | |
|---|---|
| Bio Springer yeast extract | 6.0 |
| Cargill soy flour | 45.0 |
| $K_2HPO_4$ | 3.25 |
| $KH_2PO_4$ | 1.875 |
| Corn Products corn syrup 1632* | 60.0 |

*Sterilized separately and added after cooling. Shake flasks were run with 150 ml medium/500 ml flask at 37° C. and 180 rpm.

Fermentations were run in 7.5 liter New Brunswick fermentors with 4.0 liters of medium. The fermentor medium contained the following (g/L):

| | |
|---|---|
| Bio Springer yeast extract | 3.5 |
| Cargill soy flour | 25.0 |
| $K_2HPO_4$ | 0.6 |
| $MgSO_4$ | 1.875 |
| $MnCl_2$ | 0.1 |
| $CaCl_2$ | 1.0 |
| $FeSO_4$ | 0.05 |
| Dextrose* | 40.0 |
| Neomycin* | 0.020 |
| Antifoam*† | 2.0 ml |

*Sterilized separately and added after cooling.
†2:1 mixture of Trans-10/PPG2000 antifoams.

Fermentors were inoculated with 150 ml of seed culture and were run at 37° C., 630 rpm with 0.5 vvm aeration (2 l/min.). Fermentors were fed with 1.6 g/l-hr. of dextrose and the pH was maintained between 6.8 and 6.9 by addition of ammonia.

| Age, hr | Control Pullulanase (Ferm D163) U/ml | Truncated Pullulanase (Ferm D165) U/ml |
|---|---|---|
| Comparison of Activity Production of Strains Producing Full-Size and Truncated Pullulanase in Batch Fermentations | | |
| 19 | 84 | 186 |
| 31 | 174 | 363 |
| 45 | 339 | 424 |
| 55 | 376 | 476 |
| 65 | 365 | 474 |
| 78 | 472 | 603 |
| 89 | 469 | 630 |
| 102 | 523 | 706 |
| 113 | 506 | 813 |
| Comparison of Plasmid Stability of Strains Producing Full-Size and Truncated Pullulanase in Batch Fermentations | | |
| 31 | 96.0 | 100 |
| 45 | 66.7 | 100 |
| 55 | 62.9 | 100 |
| 65 | 62.6 | 100 |
| 89 | 29.2 | 100 |

Values are
$$\frac{\text{(Colonies forming blue halos on the amylopectin plate)}}{\text{Colonies on amylopectin plate}} \times 100$$

Example 5
Comparison of Activity Production of Strains Producing Full-Size and Truncated Pullulanase in Batch Fermentations The shake flask medium for seed development contained the following (g/L):

| | |
|---|---|
| Bio Springer yeast extract | 6.0 |
| Cargill soy flour | 45.0 |
| $K_2HPO_4$ | 3.25 |
| $KH_2PO_4$ | 1.875 |
| Corn Products corn syrup 1632* | 60.0 |

*Sterilized separately and added after cooling. Shake flasks were run with 150 ml medium/500 ml flask at 37° C. and 180 rpm.

Fermentations were run in 7.5 liter New Brunswick fermentors with 4.0 liters of medium. The fermentor medium contained the following (g/L).

| | |
|---|---|
| Bio Springer yeast extract | 3.5 |
| Cargill soy flour | 25.0 |
| $K_2HPO_4$ | 0.6 |
| $MgSO_4$ | 1.875 |
| $MnCl_2$ | 0.1 |
| $CaCl_2$ | 1.0 |
| $FeSO_4$ | 0.05 |
| Dextrose* | 40.0 |
| Neomycin* | 0.020 |
| Antifoam*† | 2.0 ml |

*Sterilized separately and added after cooling.
†2:1 mixture of Trans-10/PPG2000 antifoams In this run, the fermentor were inoculated with twice the volume of culture from the seed flask as used in the previous experiment. Fermentors were inoculated with 300 ml of seed culture and were run at 37° C., 630 rpm with 0.5 vvm aeration (2 l/min). Fermentors were fed with 1.6 g/l-hr. of dextrose and the pH was maintained between 6.8 and 6.9 by addition of ammonia.

Comparison of Activity Production of Strains Producing Full-Size and Truncated Pullulanase in Batch Fermentations

| Age, hr | Control Pullulanase (Ferm D163) U/ml | Truncated Pullulanase (Ferm D165) U/ml |
| --- | --- | --- |
| 17 | 59 | 125 |
| 25 | 88 | 199 |
| 36 | 146 | 297 |
| 49 | 268 | 390 |
| 60 | 299 | 428 |
| 72 | 330 | 500 |
| 84 | 345 | 521 |
| 99 | 354 | 548 |
| 112 | 373 | 679 |

Cells were collected by centrifugation and suspended in 0.1 vol. of supernatant. From 5 to 50 μl of plasmid DNA was added to 200 μl of suspended cells, and the mixture was incubated at 37° C. (250 RPM) for 30 min. Then, 800 μl of pre-warmed TBAB broth was added; incubation continued for another 90 min. Cells were plated onto TBAB containing 10 μg/ml Kanamycin and 10 g/L amylopectin and incubated for 1 to 2 days at 37° C.

Colonies growing in the presence of kanamycin and exhibiting zones of clearing, which indicates amylopectin hydrolysis, were identified as transformants.

It is understood that the invention is not confined to the particular protocols, constructs, and arrangements of genetic elements herein illustrated and described, but embraces all modified forms thereof as come within the scope of the following claims.

What is claimed is:

1. A DNA expression construct comprising, in 5' to 3' order: an α-amylase promoter sequence derived from *Bacillus stearothermophilus* operationally linked to an α-amylase leader sequence derived from *Bacillus stearothermophilus* operationally linked to a DNA sequence encoding a pullulanase as shown in SEQ. ID. NO: 21.

2. The DNA expression construct of claim 1, wherein the DNA sequence encoding a pullulanase is SEQ. ID. NO: 1.

3. The DNA expression construct of claim 1, wherein the promoter sequence is included in nucleotides 1 through 361 of SEQ. ID. NO: 16.

4. The DNA expression construct of claim 1, wherein the leader sequence is nucleotides 361 to 462 of SEQ. ID. NO: 16.

5. The DNA expression construct of claim 1, further comprising a DNA sequence encoding from residue 1 to about residue 200 of the N-terminus of *Bacillus stearothermophilus* α-amylase, the DNA sequence operationally linked between the leader sequence and the DNA sequence encoding a pullulanase such that the expression construct expresses a fusion protein comprising from 1 to about 200 N-terminal residues of *Bacillus stearothermophilus* α-amylase bonded to a pullulanase.

6. The DNA expression construct of claim 5, wherein the DNA sequence encoding N-terminal residues of *Bacillus stearothermophilus* α-amylase consists of between at least 1 but no more than 200 codons encoding the α-amylase.

7. The DNA expression construct of claim 5, which encodes and expresses a mature fusion protein as shown in SEQ. ID. NO: 19.

8. The DNA expression construct of claim 5 which is SEQ. ID. NO: 16.

9. The DNA expression construct of claim 5 which is SEQ. ID. NO: 20.

10. A genetically-engineered microbe transformed to contain and express a DNA expression construct as recited in claim 1.

11. The genetically-engineered microbe of claim 10 which is *Bacillus subtilis*.

12. A genetically-engineered microbe transformed to contain and express a DNA expression construct as recited in claim 5.

13. The genetically-engineered microbe of claim 12 which is *Bacillus subtilis*.

14. The genetically engineered microbe of claim 12 transformed to contain and express SEQ. ID. NO: 16.

15. The genetically engineered microbe of claim 12 transformed to contain and express SEQ. ID. NO: 20.

16. A process for manufacturing a recombinant pullulanase comprising:

(a) transforming a microbial host to contain an expression construct comprising, in 5' to 3' order: an α-amylase promoter sequence derived from *Bacillus stearothermophilus* operationally linked to an α-amylase leader sequence derived from *Bacillus stearothermophilus* operationally linked to a DNA sequence encoding a pullulanase as shown in SEQ. ID. NO: 21; and then (b) culturing the transformed host on a suitable growth medium wherein the transformed host expresses the encoded pullulanase.

17. The process of claim 16, wherein in step (a) a *Bacillus subtilis* host is transformed.

18. The process of claim 16, wherein in step (a) the host is transformed with an expression construct wherein the DNA sequence encoding a pullulanase is SEQ. ID. NO: 1.

19. The process of claim 16, wherein in step (a) the host is transformed with an expression construct comprising SEQ. ID. NO: 16.

20. The process of claim 16, wherein in step (a) the host is transformed with an expression construct comprising SEQ. ID. NO: 20.

21. The process of claim 16, wherein in step (a), the host is transformed with an expression construct further comprising a DNA sequence encoding from residue 1 to about residue 200 of the N-terminus of *Bacillus stearothermophilus* α-amylase, the DNA sequence operationally linked between the leader sequence and the DNA sequence encoding a pullulanase; and in step (b), culturing the transformed host under conditions wherein the transformed host expresses a fusion protein comprising from residue 1 to about residue 200 of the N-terminus of *Bacillus stearothermophilus* α-amylase bonded to a pullulanase.

22. The process of claim 21, wherein in step (a) the host is transformed with an expression construct wherein the DNA sequence encoding a pullulanase encodes a pullulanase as shown in is SEQ. ID. NO: 19.

23. The process of claim 21, wherein in step (a) the host is transformed with an expression construct wherein the DNA sequence encoding a pullulanase encodes a pullulanase as shown in is SEQ. ID. NO: 21.

24. The process of claim 21, wherein in step (a), the host is transformed with SEQ. ID. NO: 16.

25. The process of claim 21, wherein in step (a), the host is transformed with SEQ. ID. NO: 20.

* * * * *

SEQUENCE LISTING

<160> NUMBER OF SEQ ID NOS: 22

<210> SEQ ID NO 1
<211> LENGTH: 2781
<212> TYPE: DNA
<213> ORGANISM: Bacillus naganoensis
<220> FEATURE:
<221> NAME/KEY: CDS
<222> LOCATION: (1)..(2778)

<400> SEQUENCE: 1

```
gat ggg aac acc aca aac atc gta gtc cat tat ttt cgt cct agt ggg      48
Asp Gly Asn Thr Thr Asn Ile Val Val His Tyr Phe Arg Pro Ser Gly
 1               5                  10                  15 gat tat acg gat tgg aat ctt tgg atg tgg ccg gag aac ggt gat ggg      96
Asp Tyr Thr Asp Trp Asn Leu Trp Met Trp Pro Glu Asn Gly Asp Gly
                20                  25                  30 gct gag tat gat ttt aat caa ccg act gat tct tat ggg gag gtt gca     144
Ala Glu Tyr Asp Phe Asn Gln Pro Thr Asp Ser Tyr Gly Glu Val Ala
            35                  40                  45 agt gtg gac att cct gga aac cca agt caa gta ggg att att gtc cgt     192
Ser Val Asp Ile Pro Gly Asn Pro Ser Gln Val Gly Ile Ile Val Arg
        50                  55                  60 aaa gga aat tgg gat gcg aaa gac att gat agt gac cgc tac atc gat     240
Lys Gly Asn Trp Asp Ala Lys Asp Ile Asp Ser Asp Arg Tyr Ile Asp
 65                  70                  75                  80 tta agc aaa ggg cat gag att tgg ctc gtc caa gga aac agc cag att     288
Leu Ser Lys Gly His Glu Ile Trp Leu Val Gln Gly Asn Ser Gln Ile
                85                  90                  95 ttc tat agt gaa aag gat gct gag gca gcc gca caa cct gct gta agt     336
Phe Tyr Ser Glu Lys Asp Ala Glu Ala Ala Ala Gln Pro Ala Val Ser
               100                 105                 110 aac gct tat tta gat gct tcc aac caa gtg ttg gtc aag ctt agc cag     384
Asn Ala Tyr Leu Asp Ala Ser Asn Gln Val Leu Val Lys Leu Ser Gln
           115                 120                 125 ccg ttt act ctt ggt gaa ggt tca agc ggt ttt acg gtt cat gat gac     432
Pro Phe Thr Leu Gly Glu Gly Ser Ser Gly Phe Thr Val His Asp Asp
       130                 135                 140
```

-continued

| | | |
|---|---|---|
| aca gca aat aag gat att cca gtt aca tct gtt agt gat gcc aat cag<br>Thr Ala Asn Lys Asp Ile Pro Val Thr Ser Val Ser Asp Ala Asn Gln<br>145                  150                  155                  160 | 480 | |
| gta acg gct gtt tta gca ggt act ttc cag cat att ttt ggg ggg agt<br>Val Thr Ala Val Leu Ala Gly Thr Phe Gln His Ile Phe Gly Gly Ser<br>                165                  170                  175 | 528 | |
| gat tgg gca ccg gat aat cac aat act tta cta aaa aag gtg aat agc<br>Asp Trp Ala Pro Asp Asn His Asn Thr Leu Leu Lys Lys Val Asn Ser<br>        180                  185                  190 | 576 | |
| aat ctc tat caa ttt tca gga aat ctt cct gaa gga aac tac caa tat<br>Asn Leu Tyr Gln Phe Ser Gly Asn Leu Pro Glu Gly Asn Tyr Gln Tyr<br>            195                  200                  205 | 624 | |
| aaa gtg gct tta aat gat agc tgg aat aat ccg agc tac cca tct gat<br>Lys Val Ala Leu Asn Asp Ser Trp Asn Asn Pro Ser Tyr Pro Ser Asp<br>210                  215                  220 | 672 | |
| aac att aat ttg aca gtg cca gct ggt ggt gcc cat gtt aca ttt tct<br>Asn Ile Asn Leu Thr Val Pro Ala Gly Gly Ala His Val Thr Phe Ser<br>225                  230                  235                  240 | 720 | |
| tat ata cca tcc acc cat gct gtt tat gac acg att aac aat cct aat<br>Tyr Ile Pro Ser Thr His Ala Val Tyr Asp Thr Ile Asn Asn Pro Asn<br>                245                  250                  255 | 768 | |
| gcg gat tta caa gta gat agc agc ggt gtt aag acg gat ctc gtg gcg<br>Ala Asp Leu Gln Val Asp Ser Ser Gly Val Lys Thr Asp Leu Val Ala<br>        260                  265                  270 | 816 | |
| gtt act ctt gga gaa aat cct gat gta agc cat acc ctg tcc att caa<br>Val Thr Leu Gly Glu Asn Pro Asp Val Ser His Thr Leu Ser Ile Gln<br>            275                  280                  285 | 864 | |
| aca gag gac tat cag gca gga cag gtc ata cct cgt aag gtg ctt gat<br>Thr Glu Asp Tyr Gln Ala Gly Gln Val Ile Pro Arg Lys Val Leu Asp<br>290                  295                  300 | 912 | |
| tca tcc cag tac tac tat tcc gga gat gat ctc ggg aat acc tat aca<br>Ser Ser Gln Tyr Tyr Tyr Ser Gly Asp Asp Leu Gly Asn Thr Tyr Thr<br>305                  310                  315                  320 | 960 | |
| aag aat gca act acc ttt aag gtc tgg gcg cct aca tcc act caa gta<br>Lys Asn Ala Thr Thr Phe Lys Val Trp Ala Pro Thr Ser Thr Gln Val<br>                325                  330                  335 | 1008 | |
| aat gtc ctt ctt tat aat agt gca acc ggc gcg gta act aaa acg gtt<br>Asn Val Leu Leu Tyr Asn Ser Ala Thr Gly Ala Val Thr Lys Thr Val<br>        340                  345                  350 | 1056 | |
| cca atg acc gca tca ggc cat ggt gta tgg gaa gca aca gtc aac caa<br>Pro Met Thr Ala Ser Gly His Gly Val Trp Glu Ala Thr Val Asn Gln<br>            355                  360                  365 | 1104 | |
| gac ctt gaa aat tgg tat tac atg tat gag gta aca gga caa ggc tca<br>Asp Leu Glu Asn Trp Tyr Tyr Met Tyr Glu Val Thr Gly Gln Gly Ser<br>370                  375                  380 | 1152 | |
| acc cga acg gct gtt gat ccg tat gca aca gct att gca cca aac gga<br>Thr Arg Thr Ala Val Asp Pro Tyr Ala Thr Ala Ile Ala Pro Asn Gly<br>385                  390                  395                  400 | 1200 | |
| acg aga ggc atg att gtg gac cta gcc aaa aca gac ccg gcc gga tgg<br>Thr Arg Gly Met Ile Val Asp Leu Ala Lys Thr Asp Pro Ala Gly Trp<br>                405                  410                  415 | 1248 | |
| gag agt gac aaa cat att acg cca aag aat ata gaa gat gaa gtc atc<br>Glu Ser Asp Lys His Ile Thr Pro Lys Asn Ile Glu Asp Glu Val Ile<br>        420                  425                  430 | 1296 | |
| tat gaa atg gat gtt cgt gac ttt tcc atc gac tct aat tcg ggt atg<br>Tyr Glu Met Asp Val Arg Asp Phe Ser Ile Asp Ser Asn Ser Gly Met<br>            435                  440                  445 | 1344 | |
| aaa aat aaa gga aag tat ttg gca ctt aca gaa aaa gga act aaa ggc<br>Lys Asn Lys Gly Lys Tyr Leu Ala Leu Thr Glu Lys Gly Thr Lys Gly<br>450                  455                  460 | 1392 | |

```
cct gac aat gta aag aca ggg gta gat tcc tta aaa caa ctt ggg att    1440
Pro Asp Asn Val Lys Thr Gly Val Asp Ser Leu Lys Gln Leu Gly Ile
465                 470                 475                 480 act cat gtt cag ctt cag cct gtt ttc gca ttt aat agt gtc aat gaa    1488
Thr His Val Gln Leu Gln Pro Val Phe Ala Phe Asn Ser Val Asn Glu
            485                 490                 495 aac gat cca act caa tat aat tgg ggt tat gac cct cgc aac tac aat    1536
Asn Asp Pro Thr Gln Tyr Asn Trp Gly Tyr Asp Pro Arg Asn Tyr Asn
        500                 505                 510 gtt cct gag gga caa tat gct act aat gca aac gga aca act cgg att    1584
Val Pro Glu Gly Gln Tyr Ala Thr Asn Ala Asn Gly Thr Thr Arg Ile
    515                 520                 525 aaa gag ttt aag gaa atg gtt ctt tca ctc cat cag gac cac att ggg    1632
Lys Glu Phe Lys Glu Met Val Leu Ser Leu His Gln Asp His Ile Gly
530                 535                 540 gtt aat atg gat gtt gtt tat aat cat acc ttt gcc acg caa atc tct    1680
Val Asn Met Asp Val Val Tyr Asn His Thr Phe Ala Thr Gln Ile Ser
545                 550                 555                 560 gac ttc gat aag att gtg cca gaa tat tac tac cgc acg gat gat gct    1728
Asp Phe Asp Lys Ile Val Pro Glu Tyr Tyr Tyr Arg Thr Asp Asp Ala
            565                 570                 575 ggt aac tac act aac ggc tca ggt act gga aac gaa atc gca gcc gaa    1776
Gly Asn Tyr Thr Asn Gly Ser Gly Thr Gly Asn Glu Ile Ala Ala Glu
        580                 585                 590 aga cca atg gtt caa aaa ttt att atc gat tca ctt aag ttt tgg gtc    1824
Arg Pro Met Val Gln Lys Phe Ile Ile Asp Ser Leu Lys Phe Trp Val
    595                 600                 605 aat gag tac cac gtt gac ggt ttc cgt ttt gac tta atg gcg ttg ctt    1872
Asn Glu Tyr His Val Asp Gly Phe Arg Phe Asp Leu Met Ala Leu Leu
610                 615                 620 gga aaa gat aca atg tct aaa gct gcc acg cag ctt cat gcc att gat    1920
Gly Lys Asp Thr Met Ser Lys Ala Ala Thr Gln Leu His Ala Ile Asp
625                 630                 635                 640 cca gga att gct ctc tac ggt gag cca tgg aca gga gga aca tcc gcg    1968
Pro Gly Ile Ala Leu Tyr Gly Glu Pro Trp Thr Gly Gly Thr Ser Ala
            645                 650                 655 ctg cca gcc gat cag ctt tta aca aaa gga gct caa aaa ggc atg gga    2016
Leu Pro Ala Asp Gln Leu Leu Thr Lys Gly Ala Gln Lys Gly Met Gly
        660                 665                 670 gtg gct gta ttt aat gac aat ctg cga aac ggt ttg gac ggc agt gtc    2064
Val Ala Val Phe Asn Asp Asn Leu Arg Asn Gly Leu Asp Gly Ser Val
    675                 680                 685 ttt gat tca tct gct caa ggt ttt gcg aca ggt gct act ggt tta acg    2112
Phe Asp Ser Ser Ala Gln Gly Phe Ala Thr Gly Ala Thr Gly Leu Thr
690                 695                 700 gat gct att aaa aat gga gtt gaa gga agt att aat gac ttc acc gct    2160
Asp Ala Ile Lys Asn Gly Val Glu Gly Ser Ile Asn Asp Phe Thr Ala
705                 710                 715                 720 tca cca ggc gag acg atc aac tat gtc aca agt cat gat aac tat acc    2208
Ser Pro Gly Glu Thr Ile Asn Tyr Val Thr Ser His Asp Asn Tyr Thr
            725                 730                 735 ctt tgg gac aag att gcc caa agc aat cca aac gat tct gaa gcg gat    2256
Leu Trp Asp Lys Ile Ala Gln Ser Asn Pro Asn Asp Ser Glu Ala Asp
        740                 745                 750 cga att aaa atg gat gag ctc gct caa gcg atc gtc atg acc tca caa    2304
Arg Ile Lys Met Asp Glu Leu Ala Gln Ala Ile Val Met Thr Ser Gln
    755                 760                 765 ggc att cct ttc atg cag ggc ggg gaa gaa atg ctt cgt acg aaa ggc    2352
Gly Ile Pro Phe Met Gln Gly Gly Glu Glu Met Leu Arg Thr Lys Gly
```

-continued

```
                      770                     775                     780
ggc aac gac aat agc tat aat gct ggt gat gta gtg aac gag ttt gat         2400
Gly Asn Asp Asn Ser Tyr Asn Ala Gly Asp Val Val Asn Glu Phe Asp
785                     790                     795                     800 tgg agc aga aaa gct caa tat cca gat gtt ttc aat tat tat agc ggg         2448
Trp Ser Arg Lys Ala Gln Tyr Pro Asp Val Phe Asn Tyr Tyr Ser Gly
                        805                     810                     815 ctg att cat ctt cgt ctt gat cac cca gcc ttc cgc atg acg aca gct         2496
Leu Ile His Leu Arg Leu Asp His Pro Ala Phe Arg Met Thr Thr Ala
                820                     825                     830 aat gaa atc aat agc cac ctc caa ttc cta aat agc cca gag aac aca         2544
Asn Glu Ile Asn Ser His Leu Gln Phe Leu Asn Ser Pro Glu Asn Thr
            835                     840                     845 gtg gcc tat gaa tta tct gat cat gca aat aaa gat aca tgg ggt aat         2592
Val Ala Tyr Glu Leu Ser Asp His Ala Asn Lys Asp Thr Trp Gly Asn
        850                     855                     860 att gtg gtt att tat aat cca aat aaa acg gca gaa acc att aat ttg         2640
Ile Val Val Ile Tyr Asn Pro Asn Lys Thr Ala Glu Thr Ile Asn Leu
865                     870                     875                     880 cca agc ggg aaa tgg gaa atc aat gcg acg agc ggt aag gtg gga gaa         2688
Pro Ser Gly Lys Trp Glu Ile Asn Ala Thr Ser Gly Lys Val Gly Glu
                        885                     890                     895 tcc aca ctt ggt caa gca gag ggc agt gtt caa gtt cca ggc ata tct         2736
Ser Thr Leu Gly Gln Ala Glu Gly Ser Val Gln Val Pro Gly Ile Ser
                900                     905                     910 atg atg att ctt cat caa gaa gta agc cca tct gat ggt aaa tag             2781
Met Met Ile Leu His Gln Glu Val Ser Pro Ser Asp Gly Lys
            915                     920                     925

<210> SEQ ID NO 2
<211> LENGTH: 926
<212> TYPE: PRT
<213> ORGANISM: Bacillus naganoensis

<400> SEQUENCE: 2

Asp Gly Asn Thr Thr Asn Ile Val Val His Tyr Phe Arg Pro Ser Gly
  1               5                  10                  15

Asp Tyr Thr Asp Trp Asn Leu Trp Met Trp Pro Glu Asn Gly Asp Gly
             20                  25                  30

Ala Glu Tyr Asp Phe Asn Gln Pro Thr Asp Ser Tyr Gly Glu Val Ala
         35                  40                  45

Ser Val Asp Ile Pro Gly Asn Pro Ser Gln Val Gly Ile Ile Val Arg
     50                  55                  60

Lys Gly Asn Trp Asp Ala Lys Asp Ile Asp Ser Asp Arg Tyr Ile Asp
 65                  70                  75                  80

Leu Ser Lys Gly His Glu Ile Trp Leu Val Gln Gly Asn Ser Gln Ile
                 85                  90                  95

Phe Tyr Ser Glu Lys Asp Ala Glu Ala Ala Gln Pro Ala Val Ser
             100                 105                 110

Asn Ala Tyr Leu Asp Ala Ser Asn Gln Val Leu Val Lys Leu Ser Gln
         115                 120                 125

Pro Phe Thr Leu Gly Glu Gly Ser Ser Gly Phe Thr Val His Asp Asp
     130                 135                 140

Thr Ala Asn Lys Asp Ile Pro Val Thr Ser Val Ser Asp Ala Asn Gln
145                 150                 155                 160

Val Thr Ala Val Leu Ala Gly Thr Phe Gln His Ile Phe Gly Gly Ser
                 165                 170                 175
```

-continued

```
Asp Trp Ala Pro Asp Asn His Asn Thr Leu Leu Lys Lys Val Asn Ser
            180                 185                 190

Asn Leu Tyr Gln Phe Ser Gly Asn Leu Pro Glu Gly Asn Tyr Gln Tyr
            195                 200                 205

Lys Val Ala Leu Asn Asp Ser Trp Asn Asn Pro Ser Tyr Pro Ser Asp
            210                 215                 220

Asn Ile Asn Leu Thr Val Pro Ala Gly Gly Ala His Val Thr Phe Ser
225                 230                 235                 240

Tyr Ile Pro Ser Thr His Ala Val Tyr Asp Thr Ile Asn Asn Pro Asn
                    245                 250                 255

Ala Asp Leu Gln Val Asp Ser Ser Gly Val Lys Thr Asp Leu Val Ala
            260                 265                 270

Val Thr Leu Gly Glu Asn Pro Asp Val Ser His Thr Leu Ser Ile Gln
            275                 280                 285

Thr Glu Asp Tyr Gln Ala Gly Gln Val Ile Pro Arg Lys Val Leu Asp
            290                 295                 300

Ser Ser Gln Tyr Tyr Ser Gly Asp Asp Leu Gly Asn Thr Tyr Thr
305                 310                 315                 320

Lys Asn Ala Thr Thr Phe Lys Val Trp Ala Pro Thr Ser Thr Gln Val
                    325                 330                 335

Asn Val Leu Leu Tyr Asn Ser Ala Thr Gly Ala Val Thr Lys Thr Val
            340                 345                 350

Pro Met Thr Ala Ser Gly His Gly Val Trp Glu Ala Thr Val Asn Gln
            355                 360                 365

Asp Leu Glu Asn Trp Tyr Tyr Met Tyr Glu Val Thr Gly Gln Gly Ser
            370                 375                 380

Thr Arg Thr Ala Val Asp Pro Tyr Ala Thr Ala Ile Ala Pro Asn Gly
385                 390                 395                 400

Thr Arg Gly Met Ile Val Asp Leu Ala Lys Thr Asp Pro Ala Gly Trp
                    405                 410                 415

Glu Ser Asp Lys His Ile Thr Pro Lys Asn Ile Glu Asp Glu Val Ile
            420                 425                 430

Tyr Glu Met Asp Val Arg Asp Phe Ser Ile Asp Ser Asn Ser Gly Met
            435                 440                 445

Lys Asn Lys Gly Lys Tyr Leu Ala Leu Thr Glu Lys Gly Thr Lys Gly
            450                 455                 460

Pro Asp Asn Val Lys Thr Gly Val Asp Ser Leu Lys Gln Leu Gly Ile
465                 470                 475                 480

Thr His Val Gln Leu Gln Pro Val Phe Ala Phe Asn Ser Val Asn Glu
                    485                 490                 495

Asn Asp Pro Thr Gln Tyr Asn Trp Gly Tyr Asp Pro Arg Asn Tyr Asn
            500                 505                 510

Val Pro Glu Gly Gln Tyr Ala Thr Asn Ala Asn Gly Thr Thr Arg Ile
            515                 520                 525

Lys Glu Phe Lys Glu Met Val Leu Ser Leu His Gln Asp His Ile Gly
            530                 535                 540

Val Asn Met Asp Val Val Tyr Asn His Thr Phe Ala Thr Gln Ile Ser
545                 550                 555                 560

Asp Phe Asp Lys Ile Val Pro Glu Tyr Tyr Tyr Arg Thr Asp Asp Ala
                    565                 570                 575

Gly Asn Tyr Thr Asn Gly Ser Gly Thr Gly Asn Glu Ile Ala Ala Glu
            580                 585                 590

Arg Pro Met Val Gln Lys Phe Ile Ile Asp Ser Leu Lys Phe Trp Val
```

```
              595                 600                 605
Asn Glu Tyr His Val Asp Gly Phe Arg Phe Asp Leu Met Ala Leu Leu
    610                 615                 620
Gly Lys Asp Thr Met Ser Lys Ala Ala Thr Gln Leu His Ala Ile Asp
625                 630                 635                 640
Pro Gly Ile Ala Leu Tyr Gly Glu Pro Trp Thr Gly Thr Ser Ala
                645                 650                 655
Leu Pro Ala Asp Gln Leu Leu Thr Lys Gly Ala Gln Lys Gly Met Gly
                660                 665                 670
Val Ala Val Phe Asn Asp Asn Leu Arg Asn Gly Leu Asp Gly Ser Val
            675                 680                 685
Phe Asp Ser Ser Ala Gln Gly Phe Ala Thr Gly Ala Thr Gly Leu Thr
    690                 695                 700
Asp Ala Ile Lys Asn Gly Val Glu Gly Ser Ile Asn Asp Phe Thr Ala
705                 710                 715                 720
Ser Pro Gly Glu Thr Ile Asn Tyr Val Thr Ser His Asp Asn Tyr Thr
                725                 730                 735
Leu Trp Asp Lys Ile Ala Gln Ser Asn Pro Asn Asp Ser Glu Ala Asp
                740                 745                 750
Arg Ile Lys Met Asp Glu Leu Ala Gln Ala Ile Val Met Thr Ser Gln
            755                 760                 765
Gly Ile Pro Phe Met Gln Gly Gly Glu Glu Met Leu Arg Thr Lys Gly
    770                 775                 780
Gly Asn Asp Asn Ser Tyr Asn Ala Gly Asp Val Val Asn Glu Phe Asp
785                 790                 795                 800
Trp Ser Arg Lys Ala Gln Tyr Pro Asp Val Phe Asn Tyr Tyr Ser Gly
                805                 810                 815
Leu Ile His Leu Arg Leu Asp His Pro Ala Phe Arg Met Thr Thr Ala
                820                 825                 830
Asn Glu Ile Asn Ser His Leu Gln Phe Leu Asn Ser Pro Glu Asn Thr
            835                 840                 845
Val Ala Tyr Glu Leu Ser Asp His Ala Asn Lys Asp Thr Trp Gly Asn
    850                 855                 860
Ile Val Val Ile Tyr Asn Pro Asn Lys Thr Ala Glu Thr Ile Asn Leu
865                 870                 875                 880
Pro Ser Gly Lys Trp Glu Ile Asn Ala Thr Ser Gly Lys Val Gly Glu
                885                 890                 895
Ser Thr Leu Gly Gln Ala Glu Gly Ser Val Gln Val Pro Gly Ile Ser
                900                 905                 910
Met Met Ile Leu His Gln Glu Val Ser Pro Ser Asp Gly Lys
            915                 920                 925

<210> SEQ ID NO 3
<211> LENGTH: 14
<212> TYPE: PRT
<213> ORGANISM: Bacillus naganoensis

<400> SEQUENCE: 3

```
<223> OTHER INFORMATION: Description of Artificial Sequence: Primer

<400> SEQUENCE: 4
gayggnaaya cnacnaayat hgtngtncay ta                              32

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: tryptic
      digest 1

<400> SEQUENCE: 5

Tyr Asn Val Pro Glu Gly Tyr Gln
  1               5

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 6
tccttcaggg acgttgta                                              18

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: tryptic
      digest 2

<400> SEQUENCE: 7

Asp Ala Glu Ala Ala Ala Gln Pro Ala Val Ser Asn Ala Tyr Leu Asp
  1               5                  10                  15

Ala

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 8
gtttcgaatg cgtatttgga t                                          21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 9
atccaaatac gcattcgaaa c                                          21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer
```

```
<400> SEQUENCE: 10
atgtggccgg agaacggtgg                                                    20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 11
gttgcgaggg tcataacccc aat                                                23

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
gggggtaccg atgggaacac cacaaacatc g                                       31

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: priimer

<400> SEQUENCE: 13
ggatcctaag ttcatttagg tcgatgaagg                                         30

<210> SEQ ID NO 14
<211> LENGTH: 5609
<212> TYPE: DNA
<213> ORGANISM: Artificial Sequence
<220> FEATURE:
<223> OTHER INFORMATION: Description of Artificial Sequence: pCPC717

<400> SEQUENCE: 14
gatcatcccc cgctcccttc tcctttgttt ggccaacttc cttctctcct ttccttttta       60
tattctttgt gcaatcgttt gcacaaaacg gttgatgcaa acgatttcat caataaacag      120
aatatttcaa ctatattttc cacttgttga aaaacgaatc gttctgttgt tctattttcg      180
attcgtgtca aactcaaaat tgtttaaatt cgatattgaa aacgattaca aataaaaatt      240
ataatagacg taaacgttcg agggtttgct cccttttac tcttttatg caatcgtttc        300 ccttaatttt ttggaagcca aaccgtcgaa tgtaacattt gattaagggg aagggcatt       360 gtgctaacgt ttcaccgcat cattcgaaaa ggatggatgt tcctgctcgc gttttgctc       420 actgcctcgc tgttctgccc aacaggacag cacgccaagg ctgccgcacc gtttaacggc      480
accatgatgc agtattttga atggtacttg ccggatgatg gcacgttatg gaccaaggtg      540
gccaatgaag ccaacaactt atccagcctt ggcatcaccg ctctttggct gccgcccgct      600
tacaaaggaa caagccgcag cgacgtaggg tacggagtat acgacttgta tgacctcggc      660
gaattcaatc aaaaagggac cgtccgcaca aaatatggaa caaaagctca atatcttcaa      720
gccattcaaa ccgcccaagc cgctggaatg caagtgtacg ccgatgtcgt gttcgaccat      780
aaaggccgcg ctgacggcac ggaatgggtg gacgccgtcg aagtcaatcc gtccgaccgc      840
```

```
                                             -continued aaccaagaaa tctcgggcac ctatcaaatc caagcatgga cgaaatttga ttttcccggg      900
cggggcaaca cctactccag ctttaagtgg cgctggtacc attttgacgg cgttgattgg      960
gacgaaagcc gaaaattaag ccgcatttac aaattccgcg gcatcggcaa agcgtgggat     1020
tgggaagtag acacagaaaa cggaaactat gactacttaa tgtatgccga ccttgatatg     1080
gatcatcccg aagtcgtgac cgagctgaaa actgggggaa atggtatgt caacacaacg      1140 aacattgatg ggttccggct tgatgccgtc aagcatatta agttcagttt ttttcctgat     1200
tggttgtcgt atgtgcgttc tcagactggc aagccgctat ttaccgtcgg ggaatattgg     1260
agctatgaca tcaacaagtt gcacaattac attacgaaaa caaacggaac gatgtctttg     1320
tttgatgccc cgttacacaa caaatttat accgcttcca atcaggggg cgcatttgat      1380 atgcgcacgt taatgaccaa tactctcatg aaagatcaac cgacattggc cgtcaccttc     1440
gttgataatc atgacaccga acccggccaa gcgctgcagt catgggtcga cccatggttc     1500
aaaccgttgg cttacgcctt tattctaact cggcaggaag atacccgtg cgtctttat      1560 ggtgactatt atggcattcc acaatataac attccttcgc tgaaaagcaa aatcgatccg     1620
ctcctcatcg cgcgcaggga ttatgcttac ggaacgcaac atgattatct tgatcactcc     1680
gacatcatcg ggtggacaag ggaagggtc actgaaaaac caggatccgg gctggccgca      1740
ctgatcaccg atgggccggg aggaagcaaa tggatgtacg ttggcaaaca acacgctgga     1800
aaagtgttct atgaccttac cggcaaccgg agtgacaccg tcaccatcaa cagtgatgga     1860 tgggggaat tcaaagtcaa tggcggttcg gtttcggttt gggttcctag aaaaacgacc     1920
gtttctacca tcgctcggcc gatcacaacc cgaccgtgga ctggtgaatt cgtccgttgg     1980
accgaaccac ggttggtggc atggccttga tgcctgcgat cagggaatga gtttataaaa     2040 taaaaaagc acctgaaaag gtgtcttttt ttgatggttt tgaacttgtt ctttcttatc      2100
ttgatacata tagaaataac gtcatttta tttagttgc tgaaaggtgc gttgaagtgt       2160
tggtatgtat gtgttttaaa gtattgaaaa cccttaaaat tggttgcaca gaaaaacccc     2220
atctgttaaa gttataagtg actaaacaaa taactaaata gatgggggtt tcttttaata     2280
ttatgtgtcc taatagtagc atttattcag atgaaaaatc aagggtttta gtggacaaga     2340 caaaagtgg aaaagtgaga ccatggagag aaaagaaaat cgctaatgtt gattactttg     2400
aacttctgca tattcttgaa tttaaaaagg ctgaaagagt aaaagattgt gctgaaatat      2460
tagagtataa acaaaatcgt gaaacaggcg aaagaaagtt gtatcgagtg tggttttgta     2520
aatccaggct ttgtccaatg tgcaactgga ggagagcaat gaaacatggc attcagtcac     2580
aaaaggttgt tgctgaagtt attaaacaaa agccaacagt tcgttggttg tttctcacat     2640
taacagttaa aaatgtttat gatggcgaag aattaaataa gagtttgtca gatatggctc     2700
aaggatttcg ccgaatgatg caatataaaa aaattaataa aaatcttgtt ggttttatgc     2760
gtgcaacgga agtgacaata aataataaag ataattctta taatcagcac atgcatgtat     2820
tggtatgtgt ggaaccaact tattttaaga atacagaaaa ctacgtgaat caaaaacaat     2880
ggattcaatt ttggaaaaag gcaatgaaat tagactatga tccaaatgta aaagttcaaa     2940
tgattcgacc gaaaaataaa tataaatcgg atatacaatc ggcaattgac gaaactgcaa     3000
aatatcctgt aaaggatacg gattttatga ccgatgatga agaaaagaat ttgaaacgtt     3060
tgtctgattt ggaggaaggt ttacaccgta aaaggttaat ctcctatggt ggtttgttaa     3120
aagaaataca taaaaaatta aaccttgatg acacagaaga aggcgatttg attcatacag     3180
atgatgacga aaaagccgat gaagatggat tttctattat tgcaatgtgg aattgggaac     3240
```

```
ggaaaaatta ttttattaaa gagtagttca acaaacgggc cagtttgttg aagattagat    3300
gctataattg ttattaaaag gattgaagga tgcttaggaa gacgagttat taatagctga    3360
ataagaacgg tgctctccaa atattcttat ttagaaaagc aaatctaaaa ttatctgaaa    3420
agatcgggaa tgagaatagt gaatggacca ataataatga ctagagaaga aagaatgaag    3480
attgttcatg aaattaagga acgaatattg gataaatatg gggatgatgt taaggctatt    3540
ggtgtttatg gctctcttgg tcgtcagact gatgggccct attcggatat tgagatgatg    3600
tgtgtcatgt caacagagga agcagagttc agccatgaat ggacaaccgg tgagtggaag    3660
gtggaagtga attttgatag cgaagagatt ctactagatt atgcatctca ggtggaatca    3720
gattggccgc ttacacatgg tcaattttc tctattttgc cgatttatga ttcaggtgga    3780
tacttagaga aagtgtatca aactgctaaa tcggtagaag cccaaacgtt ccacgatgcg    3840
atttgtgccc ttatcgtaga agagctgttt gaatatgcag gcaaatggcg taatattcgt    3900
gtgcaaggac cgacaacatt tctaccatcc ttgactgtac aggtagcaat ggcaggtgcc    3960
atgttgattg gtctgcatca tcgcatctgt tatacgacga gcgcttcggt cttaactgaa    4020
gcagttaagc aatcagatct tccttcaggt tatgaccatc tgtgccagtt cgtaatgtct    4080
ggtcaacttt ccgactctga gaacttctg gaatcgctag agaatttctg gaatgggatt    4140
caggagtgga cagaacgaca cggatatata gtggatgtgt caaaacgcat accatttga    4200 acgatgacct ctaataattg ttaatcatgt tggttacgta tttattaact ctcctagta    4260 ttagtaatta tcatggctgt catggcgcat taacggaata aagggtgtgc ttaaatcggg    4320 ccatttttgcg taataagaaa aaggattaat tatgagcgaa ttgaattaat aataaggtaa    4380
tagatttaca ttagaaaatg aaagggggatt ttatgcgtga aatgttaca gtctatcccg    4440 gcattgccag tcggggatat taaaaagagt ataggttttt attgcgataa actaggtttc    4500
actttggttc accatgaaga tggattcgca gttctaatgt gtaatgaggt tcggattcat    4560
ctatgggagg caagtgatga aggctggcgc tctcgtagta atgattcacc ggtttgtaca    4620
ggtgcggagt cgtttattgc tggtactgct agttgccgca ttgaagtaga gggaattgat    4680
gaattatatc aacatattaa gcctttgggc attttgcacc ccaatacatc attaaaagat    4740
cagtggtggg atgaacgaga cttttgcagta attgatcccg acaacaattt gattagcttt    4800
tttcaacaaa taaaaagcta aaatctatta ttaatctgtt cagcaatcgg gcgcgattgc    4860
tgaataaaag atacgagaga cctctcttgt atcttttta tttgagtgg ttttgtccgt    4920 tacactagaa aaccgaaaga caataaaaat tttattcttg ctgagtctgg ctttcggtaa    4980
gctagacaaa acggacaaaa taaaaattgg caagggttta aagtggaga tttttgagt    5040 gatcttctca aaaatacta cctgtcccct gctgatttt aaacgagcac gagagcaaaa    5100 ccccccttg ctgaggtggc agagggcagg ttttttgtt tctttttct cgtaaaaaaa    5160 agaaaggtct taaaggtttt atggttttgg tcggcactgc cgacagcctc gcagagcaca    5220
cactttatga atataaagta tagtgtgtta tactttactt ggaagtggtt gccggaaaga    5280
gcgaaaatgc ctcacatttg tgccacctaa aaggagcga tttacatatg agttatgcag    5340
tttgtagaat gcaaaaagtg aaatcagctg gactaaaagg catgcaattt cataatcaaa    5400
gagagcgaaa aagtagaacg aatgatgata ttgaccatga gcgaacacgt gaaaattatg    5460
atttgaaaaa tgataaaaat attgattaca acgaacgtgt caaagaaatt attgaatcac    5520
aaaaaacagg tacaagaaaa acgaggaaag atgctgttct tgtaaatgag ttgctagtaa    5580
```

-continued

| catctgaccg agatttttt gagcaactg | 5609 |

<210> SEQ ID NO 15
<211> LENGTH: 5609
<212> TYPE: DNA
<213> ORGANISM: Artificial Sequence
<220> FEATURE:
<223> OTHER INFORMATION: Description of Artificial Sequence: pEB200

<400> SEQUENCE: 15

| gatcatcccc cgctcccttc tcctttgttt ggccaacttc cttctctcct ttccttttta | 60 |
| tattctttgt gcaatcgttt gcacaaaacg gttgatgcaa acgatttcat caataaacag | 120 |
| aatatttcaa ctatattttc cacttgttga aaaacgaatc gttctgttgt tctattttcg | 180 |
| attcgtgtca aactcaaaat tgtttaaatt cgatattgaa aacgattaca aataaaaatt | 240 |
| ataatagacg taaacgttcg agggtttgct cccttttac tctttttatg caatcgtttc | 300 |
| ccttaatttt ttggaagcca aaccgtcgaa tgtaacattt gattaagggg aagggcatt | 360 |
| gtgctaacgt ttcaccgcat cattcgaaaa ggatggatgt tcctgctcgc gttttgctc | 420 |
| actgcctcgc tgttctgccc aacaggacag cacgccaagg ctgccgcacc gtttaacggt | 480 |
| accatgatgc agtattttga atggtacttg ccggatgatg gcacgttatg gaccaaggtg | 540 |
| gccaatgaag ccaacaactt atccagcctt ggcatcaccc tctttggct gccgcccgct | 600 |
| tacaaaggaa caagccgcag cgacgtaggg tacggagtat acgacttgta tgacctcggc | 660 |
| gaattcaatc aaaaagggac cgtccgcaca aaatatggaa caaaagctca atatcttcaa | 720 |
| gccattcaaa ccgcccaagc cgctggaatg caagtgtacg ccgatgtcgt gttcgaccat | 780 |
| aaaggccgcg ctgacggcac ggaatgggtg gacgccgtcg aagtcaatcc gtccgaccgc | 840 |
| aaccaagaaa tctcgggcac ctatcaaatc caagcatgga cgaaatttga ttttcccggg | 900 |
| cggggcaaca cctactccag ctttaagtgg cgctggtacc attttgacgg cgttgattgg | 960 |
| gacgaaagcc gaaaattaag ccgcatttac aaattccgcg gcatcggcaa agcgtgggat | 1020 |
| tgggaagtag acacagaaaa cggaaactat gactacttaa tgtatgccga ccttgatatg | 1080 |
| gatcatcccg aagtcgtgac cgagctgaaa aactgggga atggtatgt caacacaacg | 1140 |
| aacattgatg ggttccggct tgatgccgtc aagcatatta agttcagttt ttttcctgat | 1200 |
| tggttgtcgt atgtgcgttc tcagactggc aagccgctat ttaccgtcgg ggaatattgg | 1260 |
| agctatgaca tcaacaagtt gcacaattac attacgaaaa caaacggaac gatgtctttg | 1320 |
| tttgatgccc cgttacacaa caaatttat accgcttcca aatcagggg cgcatttgat | 1380 |
| atgcgcacgt taatgaccaa tactctcatg aaagatcaac cgacattggc cgtcaccttc | 1440 |
| gttgataatc atgacaccga acccggccaa gcgctgcagt catgggtcga cccatggttc | 1500 |
| aaaccgttgg cttacgcctt tattctaact cggcaggaag gatacccgtg cgtcttttat | 1560 |
| ggtgactatt atggcattcc acaatataac attccttcgc tgaaaagcaa aatcgatccg | 1620 |
| ctcctcatcg cgcgcaggga ttatgcttac ggaacgcaac atgattatct tgatcactcc | 1680 |
| gacatcatcg ggtggacaag ggaagggtc actgaaaaac caggatccgg gctggccgca | 1740 |
| ctgatcaccg atgggccggg aggaagcaaa tggatgtacg ttggcaaaca acacgctgga | 1800 |
| aaagtgttct atgaccttac cggcaaccgg agtgacaccg tcaccatcaa cagtgatgga | 1860 |
| tgggggggaat tcaaagtcaa tggcggttcg gtttcggttt gggttcctag aaaaacgacc | 1920 |
| gtttctacca tcgctcggcc gatcacaacc cgaccgtgga ctggtgaatt cgtccgttgg | 1980 |
| accgaaccac ggttggtggc atggccttga tgcctgcgat cagggaatga gtttataaaa | 2040 |

```
taaaaaaagc acctgaaaag gtgtcttttt ttgatggttt tgaacttgtt ctttcttatc    2100
ttgatacata tagaaataac gtcatttttta ttttagttgc tgaaaggtgc gttgaagtgt    2160
tggtatgtat gtgttttaaa gtattgaaaa cccttaaaat tggttgcaca gaaaaacccc    2220
atctgttaaa gttataagtg actaaacaaa taactaaata gatgggggtt tcttttaata    2280
ttatgtgtcc taatagtagc atttattcag atgaaaaatc aagggtttta gtggacaaga    2340 caaaagtgg aaaagtgaga ccatggagag aaaagaaaat cgctaatgtt gattactttg    2400
aacttctgca tattcttgaa tttaaaaagg ctgaaagagt aaaagattgt gctgaaatat    2460
tagagtataa acaaaatcgt gaaacaggcg aaagaaagtt gtatcgagtg tggttttgta    2520
aatccaggct ttgtccaatg tgcaactgga ggagagcaat gaaacatggc attcagtcac    2580
aaaaggttgt tgctgaagtt attaaacaaa agccaacagt tcgttggttg tttctcacat    2640
taacagttaa aaatgtttat gatggcgaag aattaaataa gagtttgtca gatatggctc    2700
aaggatttcg ccgaatgatg caatataaaa aaattaataa aaatcttgtt ggttttatgc    2760
gtgcaacgga agtgacaata aataataaag ataattctta taatcagcac atgcatgtat    2820
tggtatgtgt ggaaccaact tattttaaga atacagaaaa ctacgtgaat caaaaacaat    2880
ggattcaatt ttggaaaaag gcaatgaaat tagactatga tccaaatgta aaagttcaaa    2940
tgattcgacc gaaaaataaa tataaatcgg atatacaatc ggcaattgac gaaactgcaa    3000
aatatcctgt aaaggatacg gattttatga ccgatgatga agaaaagaat ttgaaacgtt    3060
tgtctgattt ggaggaaggt ttacaccgta aaaggttaat ctcctatggt ggtttgttaa    3120
aagaaataca taaaaaatta aaccttgatg acacagaaga aggcgatttg attcatacag    3180
atgatgacga aaaagccgat gaagatggat tttctattat tgcaatgtgg aattgggaac    3240
ggaaaaatta ttttattaaa gagtagttca acaaacgggc cagtttgttg aagattagat    3300
gctataattg ttattaaaag gattgaagga tgcttaggaa gacgagttat taatagctga    3360
ataagaacgg tgctctccaa atattcttat ttagaaaagc aaatctaaaa ttatctgaaa    3420
agatcgggaa tgagaatagt gaatggacca ataataatga ctagagaaga aagaatgaag    3480
attgttcatg aaattaagga acgaatattg gataaatatg gggatgatgt taaggctatt    3540
ggtgtttatg gctctcttgg tcgtcagact gatgggccct attcggatat tgagatgatg    3600
tgtgtcatgt caacagagga agcagagttc agccatgaat ggacaaccgg tgagtggaag    3660
gtggaagtga atttttgatag cgaagagatt ctactagatt atgcatctca ggtggaatca    3720
gattggccgc ttacacatgg tcaatttttc tctattttgc cgatttatga ttcaggtgga    3780
tacttagaga aagtgtatca aactgctaaa tcggtagaag cccaaacgtt ccacgatgcg    3840
atttgtgccc ttatcgtaga agagctgttt gaatatgcag gcaaatggcg taatattcgt    3900
gtgcaaggac cgacaacatt tctaccatcc ttgactgtac aggtagcaat ggcaggtgcc    3960
atgttgattg gtctgcatca tcgcatctgt tatacgacga gcgcttcggt cttaactgaa    4020
gcagttaagc aatcagatct tccttcaggt tatgaccatc tgtgccagtt cgtaatgtct    4080
ggtcaacttt ccgactctga gaacttctg gaatcgctag agaatttctg gaatgggatt    4140
caggagtgga cagaacgaca cggatatata gtggatgtgt caaaacgcat accattttga    4200
acgatgacct ctaataattg ttaatcatgt tggttacgta tttattaact ctcctagta    4260 ttagtaatta tcatggctgt catggcgcat taacggaata aagggtgtgc ttaaatcggg    4320 ccatttttgcg taataagaaa aaggattaat tatgagcgaa ttgaattaat aataaggtaa    4380
```

-continued

```
tagatttaca ttagaaaatg aaagggatt ttatgcgtga gaatgttaca gtctatcccg      4440
gcattgccag tcgggatat taaaaagagt ataggttttt attgcgataa actaggtttc      4500
actttggttc accatgaaga tggattcgca gttctaatgt gtaatgaggt tcggattcat      4560
ctatgggagg caagtgatga aggctggcgc tctcgtagta atgattcacc ggtttgtaca      4620
ggtgcggagt cgtttattgc tggtactgct agttgccgca ttgaagtaga gggaattgat      4680
gaattatatc aacatattaa gcctttgggc attttgcacc ccaatacatc attaaaagat      4740
cagtggtggg atgaacgaga ctttgcagta attgatcccg acaacaattt gattagcttt      4800
tttcaacaaa taaaaagcta aaatctatta ttaatctgtt cagcaatcgg gcgcgattgc      4860
tgaataaaag atacgagaga cctctcttgt atcttttta ttttgagtgg ttttgtccgt       4920
tacactagaa aaccgaaaga caataaaaat tttattcttg ctgagtctgg ctttcggtaa      4980
gctagacaaa acgacaaaa taaaaattgg caagggttta aaggtggaga ttttttgagt      5040
gatcttctca aaaatacta cctgtccctt gctgattttt aaacgagcac gagagcaaaa       5100 cccccttg ctgaggtggc agagggcagg ttttttttgtt tcttttttct cgtaaaaaaa       5160
agaaaggtct taaggttttt atggttttgg tcggcactgc cgacagcctc gcagagcaca      5220
cactttatga atataaagta tagtgtgtta tactttactt ggaagtggtt gccgaaaga       5280 gcgaaaatgc ctcacatttg tgccacctaa aaaggagcga tttacatatg agttatgcag      5340
tttgtagaat gcaaaaagtg aaatcagctg gactaaaagg catgcaattt cataatcaaa      5400
gagagcgaaa aagtagaacg aatgatgata ttgaccatga gcgaacacgt gaaaattatg      5460
atttgaaaaa tgataaaaat attgattaca cgaacgtgt caagaaatt attgaatcac       5520 aaaaacagg tacaagaaaa acgaggaaag atgctgttct tgtaaatgag ttgctagtaa       5580
catctgaccg agattttttt gagcaactg                                        5609
```

<210> SEQ ID NO 16
<211> LENGTH: 7344
<212> TYPE: DNA
<213> ORGANISM: Artificial Sequence
<220> FEATURE:
<221> NAME/KEY: CDS
<222> LOCATION: (361)..(3261)
<220> FEATURE:
<221> NAME/KEY: sig_peptide
<222> LOCATION: (361)..(462)
<220> FEATURE:
<223> OTHER INFORMATION: Description of Artificial Sequence:pEB301

<400> SEQUENCE: 16

```
gatcatcccc cgctcccttc tcctttgttt ggccaacttc cttctctcct ttcctttta      60 tattctttgt gcaatcgttt gcacaaaacg gttgatgcaa acgatttcat caataaacag      120
aatatttcaa ctatattttc cacttgttga aaaacgaatc gttctgttgt tctattttcg      180
attcgtgtca aactcaaaat tgtttaaatt cgatattgaa aacgattaca ataaaaatt       240 ataatagacg taaacgttcg agggtttgct cccttttac tcttttatg caatcgtttc        300 ccttaatttt ttggaagcca aaccgtcgaa tgtaacattt gattaagggg aagggcatt       360 gtg cta acg ttt cac cgc atc att cga aaa gga tgg atg ttc ctg ctc       408
Val Leu Thr Phe His Arg Ile Ile Arg Lys Gly Trp Met Phe Leu Leu
 1               5                  10                  15 gcg ttt ttg ctc act gcc tcg ctg ttc tgc cca aca gga cag cac gcc       456
Ala Phe Leu Leu Thr Ala Ser Leu Phe Cys Pro Thr Gly Gln His Ala
            20                  25                  30 aag gct gcc gca ccg ttt aac ggt acc gat ggg aac acc aca aac atc       504
```

```
                    Lys Ala Ala Pro Phe Asn Gly Thr Asp Gly Asn Thr Thr Asn Ile
                        35                  40                  45 gta gtc cat tat ttt cgt cct agt ggg gat tat acg gat tgg aat ctt              552
Val Val His Tyr Phe Arg Pro Ser Gly Asp Tyr Thr Asp Trp Asn Leu
 50              55                  60 tgg atg tgg ccg gag aac ggt gat ggg gct gag tat gat ttt aat caa              600
Trp Met Trp Pro Glu Asn Gly Asp Gly Ala Glu Tyr Asp Phe Asn Gln
 65              70                  75                  80 ccg act gat tct tat ggg gag gtt gca agt gtg gac att cct gga aac              648
Pro Thr Asp Ser Tyr Gly Glu Val Ala Ser Val Asp Ile Pro Gly Asn
             85                  90                  95 cca agt caa gta ggg att att gtc cgt aaa gga aat tgg gat gcg aaa              696
Pro Ser Gln Val Gly Ile Ile Val Arg Lys Gly Asn Trp Asp Ala Lys
            100                 105                 110 gac att gat agt gac cgc tac atc gat tta agc aaa ggg cat gag att              744
Asp Ile Asp Ser Asp Arg Tyr Ile Asp Leu Ser Lys Gly His Glu Ile
            115                 120                 125 tgg ctc gtc caa gga aac agc cag att ttc tat agt gaa aag gat gct              792
Trp Leu Val Gln Gly Asn Ser Gln Ile Phe Tyr Ser Glu Lys Asp Ala
130                 135                 140 gag gca gcc gca caa cct gct gta agt aac gct tat tta gat gct tcc              840
Glu Ala Ala Ala Gln Pro Ala Val Ser Asn Ala Tyr Leu Asp Ala Ser
145                 150                 155                 160 aac caa gtg ttg gtc aag ctt agc cag ccg ttt act ctt ggt gaa ggt              888
Asn Gln Val Leu Val Lys Leu Ser Gln Pro Phe Thr Leu Gly Glu Gly
                165                 170                 175 tca agc ggt ttt acg gtt cat gat gac aca gca aat aag gat att cca              936
Ser Ser Gly Phe Thr Val His Asp Asp Thr Ala Asn Lys Asp Ile Pro
                180                 185                 190 gtt aca tct gtt agt gat gcc aat cag gta acg gct gtt tta gca ggt              984
Val Thr Ser Val Ser Asp Ala Asn Gln Val Thr Ala Val Leu Ala Gly
            195                 200                 205 act ttc cag cat att ttt ggg ggt agt gat tgg gca ccg gat aat cac             1032
Thr Phe Gln His Ile Phe Gly Gly Ser Asp Trp Ala Pro Asp Asn His
            210                 215                 220 aat act tta cta aaa aag gtg aat agc aat ctc tat caa ttt tca gga             1080
Asn Thr Leu Leu Lys Lys Val Asn Ser Asn Leu Tyr Gln Phe Ser Gly
225                 230                 235                 240 aat ctt cct gaa gga aac tac caa tat aaa gtg gct tta aat gat agc             1128
Asn Leu Pro Glu Gly Asn Tyr Gln Tyr Lys Val Ala Leu Asn Asp Ser
                245                 250                 255 tgg aat aat ccg agc tac cca tct gat aac att aat ttg aca gtg cca             1176
Trp Asn Asn Pro Ser Tyr Pro Ser Asp Asn Ile Asn Leu Thr Val Pro
                260                 265                 270 gct ggt ggt gcc cat gtt aca ttt tct tat ata cca tcc acc cat gct             1224
Ala Gly Gly Ala His Val Thr Phe Ser Tyr Ile Pro Ser Thr His Ala
            275                 280                 285 gtt tat gac acg att aac aat cct aat gcg gat tta caa gta gat agc             1272
Val Tyr Asp Thr Ile Asn Asn Pro Asn Ala Asp Leu Gln Val Asp Ser
            290                 295                 300 agc ggt gtt aag acg gat ctc gtg gcg gtt act ctt gga gaa aat cct             1320
Ser Gly Val Lys Thr Asp Leu Val Ala Val Thr Leu Gly Glu Asn Pro
305                 310                 315                 320 gat gta agc cat acc ctg tcc att caa aca gag gac tat cag gca gga             1368
Asp Val Ser His Thr Leu Ser Ile Gln Thr Glu Asp Tyr Gln Ala Gly
                325                 330                 335 cag gtc ata cct cgt aag gtg ctt gat tca tcc cag tac tac tat tcc             1416
Gln Val Ile Pro Arg Lys Val Leu Asp Ser Ser Gln Tyr Tyr Tyr Ser
            340                 345                 350
```

-continued

| | |
|---|---|
| gga gat gat ctc ggg aat acc tat aca aag aat gca act acc ttt aag<br>Gly Asp Asp Leu Gly Asn Thr Tyr Thr Lys Asn Ala Thr Thr Phe Lys<br>355                     360                    365 | 1464 |
| gtc tgg gcg cct aca tcc act caa gta aat gtc ctt ctt tat aat agt<br>Val Trp Ala Pro Thr Ser Thr Gln Val Asn Val Leu Leu Tyr Asn Ser<br>370                     375                    380 | 1512 |
| gca acc ggc gcg gta act aaa acg gtt cca atg acc gca tca ggc cat<br>Ala Thr Gly Ala Val Thr Lys Thr Val Pro Met Thr Ala Ser Gly His<br>385                     390                    395                   400 | 1560 |
| ggt gta tgg gaa gca aca gtc aac caa gac ctt gaa aat tgg tat tac<br>Gly Val Trp Glu Ala Thr Val Asn Gln Asp Leu Glu Asn Trp Tyr Tyr<br>                    405                    410                    415 | 1608 |
| atg tat gag gta aca gga caa ggc tca acc cga acg gct gtt gat ccg<br>Met Tyr Glu Val Thr Gly Gln Gly Ser Thr Arg Thr Ala Val Asp Pro<br>          420                    425                    430 | 1656 |
| tat gca aca gct att gca cca aac gga acg aga ggc atg att gtg gac<br>Tyr Ala Thr Ala Ile Ala Pro Asn Gly Thr Arg Gly Met Ile Val Asp<br>               435                    440                    445 | 1704 |
| cta gcc aaa aca gac ccg gcc gga tgg gag agt gac aaa cat att acg<br>Leu Ala Lys Thr Asp Pro Ala Gly Trp Glu Ser Asp Lys His Ile Thr<br>450                     455                    460 | 1752 |
| cca aag aat ata gaa gat gaa gtc atc tat gaa atg gat gtt cgt gac<br>Pro Lys Asn Ile Glu Asp Glu Val Ile Tyr Glu Met Asp Val Arg Asp<br>465                     470                    475                   480 | 1800 |
| ttt tcc atc gac tct aat tcg ggt atg aaa aat aaa gga aag tat ttg<br>Phe Ser Ile Asp Ser Asn Ser Gly Met Lys Asn Lys Gly Lys Tyr Leu<br>                    485                    490                    495 | 1848 |
| gca ctt aca gaa aaa gga act aaa ggc cct gac aat gta aag aca ggg<br>Ala Leu Thr Glu Lys Gly Thr Lys Gly Pro Asp Asn Val Lys Thr Gly<br>          500                    505                    510 | 1896 |
| gta gat tcc tta aaa caa ctt ggg att act cat gtt cag ctt cag cct<br>Val Asp Ser Leu Lys Gln Leu Gly Ile Thr His Val Gln Leu Gln Pro<br>               515                    520                    525 | 1944 |
| gtt ttc gca ttt aat agt gtc aat gaa aac gat cca act caa tat aat<br>Val Phe Ala Phe Asn Ser Val Asn Glu Asn Asp Pro Thr Gln Tyr Asn<br>530                     535                    540 | 1992 |
| tgg ggt tat gac cct cgc aac tac aat gtt cct gag gga caa tat gct<br>Trp Gly Tyr Asp Pro Arg Asn Tyr Asn Val Pro Glu Gly Gln Tyr Ala<br>545                     550                    555                   560 | 2040 |
| act aat gca aac gga aca act cgg att aaa gag ttt aag gaa atg gtt<br>Thr Asn Ala Asn Gly Thr Thr Arg Ile Lys Glu Phe Lys Glu Met Val<br>               565                    570                    575 | 2088 |
| ctt tca ctc cat cag gac cac att ggg gtt aat atg gat gtt gtt tat<br>Leu Ser Leu His Gln Asp His Ile Gly Val Asn Met Asp Val Val Tyr<br>          580                    585                    590 | 2136 |
| aat cat acc ttt gcc acg caa atc tct gac ttc gat aag att gtg cca<br>Asn His Thr Phe Ala Thr Gln Ile Ser Asp Phe Asp Lys Ile Val Pro<br>               595                    600                    605 | 2184 |
| gaa tat tac tac cgc acg gat gat gct ggt aac tac act aac ggc tca<br>Glu Tyr Tyr Tyr Arg Thr Asp Asp Ala Gly Asn Tyr Thr Asn Gly Ser<br>610                     615                    620 | 2232 |
| ggt act gga aac gaa atc gca gcc gaa aga cca atg gtt caa aaa ttt<br>Gly Thr Gly Asn Glu Ile Ala Ala Glu Arg Pro Met Val Gln Lys Phe<br>625                     630                    635                   640 | 2280 |
| att atc gat tca ctt aag ttt tgg gtc aat gag tac cac gtt gac ggt<br>Ile Ile Asp Ser Leu Lys Phe Trp Val Asn Glu Tyr His Val Asp Gly<br>                      645                    650                    655 | 2328 |
| ttc cgt ttt gac tta atg gcg ttg ctt gga aaa gat aca atg tct aaa<br>Phe Arg Phe Asp Leu Met Ala Leu Leu Gly Lys Asp Thr Met Ser Lys<br>          660                    665                    670 | 2376 |

```
gct gcc acg cag ctt cat gcc att gat cca gga att gct ctc tac ggt     2424
Ala Ala Thr Gln Leu His Ala Ile Asp Pro Gly Ile Ala Leu Tyr Gly
            675                 680                 685 gag cca tgg aca gga gga aca tcc gcg ctg cca gcc gat cag ctt tta     2472
Glu Pro Trp Thr Gly Gly Thr Ser Ala Leu Pro Ala Asp Gln Leu Leu
    690                 695                 700 aca aaa gga gct caa aaa ggc atg gga gtg gct gta ttt aat gac aat     2520
Thr Lys Gly Ala Gln Lys Gly Met Gly Val Ala Val Phe Asn Asp Asn
705                 710                 715                 720 ctg cga aac ggt ttg gac ggc agt gtc ttt gat tca tct gct caa ggt     2568
Leu Arg Asn Gly Leu Asp Gly Ser Val Phe Asp Ser Ser Ala Gln Gly
                725                 730                 735 ttt gcg aca ggt gct act ggt tta acg gat gct att aaa aat gga gtt     2616
Phe Ala Thr Gly Ala Thr Gly Leu Thr Asp Ala Ile Lys Asn Gly Val
            740                 745                 750 gaa gga agt att aat gac ttc acc gct tca cca ggc gag acg atc aac     2664
Glu Gly Ser Ile Asn Asp Phe Thr Ala Ser Pro Gly Glu Thr Ile Asn
        755                 760                 765 tat gtc aca agt cat gat aac tat acc ctt tgg gac aag att gcc caa     2712
Tyr Val Thr Ser His Asp Asn Tyr Thr Leu Trp Asp Lys Ile Ala Gln
    770                 775                 780 agc aat cca aac gat tct gaa gcg gat cga att aaa atg gat gag ctc     2760
Ser Asn Pro Asn Asp Ser Glu Ala Asp Arg Ile Lys Met Asp Glu Leu
785                 790                 795                 800 gct caa gcg atc gtc atg acc tca caa ggc att cct ttc atg cag ggc     2808
Ala Gln Ala Ile Val Met Thr Ser Gln Gly Ile Pro Phe Met Gln Gly
                805                 810                 815 ggg gaa gaa atg ctt cgt acg aaa ggc ggc aac gac aat agc tat aat     2856
Gly Glu Glu Met Leu Arg Thr Lys Gly Gly Asn Asp Asn Ser Tyr Asn
            820                 825                 830 gct ggt gat gta gtg aac gag ttt gat tgg agc aga aaa gct caa tat     2904
Ala Gly Asp Val Val Asn Glu Phe Asp Trp Ser Arg Lys Ala Gln Tyr
        835                 840                 845 cca gat gtt ttc aat tat tat agc ggg ctg att cat ctt cgt ctt gat     2952
Pro Asp Val Phe Asn Tyr Tyr Ser Gly Leu Ile His Leu Arg Leu Asp
    850                 855                 860 cac cca gcc ttc cgc atg acg aca gct aat gaa atc aat agc cac ctc     3000
His Pro Ala Phe Arg Met Thr Thr Ala Asn Glu Ile Asn Ser His Leu
865                 870                 875                 880 caa ttc cta aat agc cca gag aac aca gtg gcc tat gaa tta tct gat     3048
Gln Phe Leu Asn Ser Pro Glu Asn Thr Val Ala Tyr Glu Leu Ser Asp
                885                 890                 895 cat gca aat aaa gat aca tgg ggt aat att gtg gtt att tat aat cca     3096
His Ala Asn Lys Asp Thr Trp Gly Asn Ile Val Val Ile Tyr Asn Pro
            900                 905                 910 aat aaa acg gca gaa acc att aat ttg cca agc ggg aaa tgg gaa atc     3144
Asn Lys Thr Ala Glu Thr Ile Asn Leu Pro Ser Gly Lys Trp Glu Ile
        915                 920                 925 aat gcg acg agc ggt aag gtg gga gaa tcc aca ctt ggt caa gca gag     3192
Asn Ala Thr Ser Gly Lys Val Gly Glu Ser Thr Leu Gly Gln Ala Glu
    930                 935                 940 ggc agt gtt caa gtt cca ggc ata tct atg atg att ctt cat caa gaa     3240
Gly Ser Val Gln Val Pro Gly Ile Ser Met Met Ile Leu His Gln Glu
945                 950                 955                 960 gta agc cca tct gat ggt aaa tagaattaaa aaattgaaat cccccctcaag       3291
Val Ser Pro Ser Asp Gly Lys
                965 attttttgag ggggatttag tctcttctta tccaatttaa tttgcggctt cgttcttttc   3351
```

-continued

```
gatggacaac gtgttcggtc ggttgtgaga tagaaaaatt gggagtgagt aggtcacaag    3411
agcagccaat tcgcttccaa atccttcatc gacctaaatg aacttaggat ccgggctggc    3471
cgcactgatc accgatgggc cgggaggaag caaatggatg tacgttggca acaacacgc     3531 tggaaaagtg ttctatgacc ttaccggcaa ccggagtgac accgtcacca tcaacagtga    3591
tggatggggg gaattcaaag tcaatggcgg ttcggtttcg gtttgggttc ctagaaaaac    3651
gaccgtttct accatcgctc ggccgatcac aacccgaccg tggactggtg aattcgtccg    3711
ttggaccgaa ccacggttgg tggcatggcc ttgatgcctg cgatcaggga atgagtttat    3771
aaaataaaaa aagcacctga aaaggtgtct tttttgatg gttttgaact tgttctttct     3831
tatcttgata catatagaaa taacgtcatt tttattttag ttgctgaaag gtgcgttgaa    3891
gtgttggtat gtatgtgttt taaagtattg aaaacccta aaattggttg cacagaaaaa     3951
ccccatctgt taaagttata agtgactaaa caaataacta aatagatggg ggtttctttt    4011
aatattatgt gtcctaatag tagcatttat tcagatgaaa atcaagggt tttagtggac      4071 aagacaaaaa gtggaaaagt gagaccatgg agagaaaaga aaatcgctaa tgttgattac    4131
tttgaacttc tgcatattct tgaatttaaa aaggctgaaa gagtaaaaga ttgtgctgaa    4191
atattagagt ataaacaaaa tcgtgaaaca ggcgaaagaa agttgtatcg agtgtggttt    4251
tgtaaatcca ggctttgtcc aatgtgcaac tggaggagag caatgaaaca tggcattcag    4311
tcacaaaagg ttgttgctga agttattaaa caaaagccaa cagttcgttg gttgtttctc    4371
acattaacag ttaaaaatgt ttatgatggc gaagaattaa ataagagttt gtcagatatg    4431
gctcaaggat ttcgccgaat gatgcaatat aaaaaaatta ataaaaatct tgttggtttt    4491
atgcgtgcaa cggaagtgac aataaataat aaagataatt cttataatca gcacatgcat    4551
gtattggtat gtgtggaacc aacttattt aagaatacag aaaactacgt gaatcaaaaa      4611
caatggattc aattttggaa aaaggcaatg aaattagact atgatccaaa tgtaaaagtt    4671
caaatgattc gaccgaaaaa taaatataaa tcggatatac aatcggcaat tgacgaaact    4731
gcaaaatatc ctgtaaagga tacgattttt atgaccgatg atgaagaaaa gaatttgaaa    4791
cgtttgtctg atttggagga aggtttacac cgtaaaaggt taatctccta tggtggtttg    4851
ttaaaagaaa tacataaaaa attaaaccctt gatgacacag aagaaggcga tttgattcat    4911
acagatgatg acgaaaaagc cgatgaagat ggattttcta ttattgcaat gtggaattgg    4971
gaacggaaaa attattttat taaagagtag ttcaacaaac gggccagttt gttgaagatt    5031
agatgctata attgttatta aaaggattga aggatgctta ggaagacgag ttattaatag    5091
ctgaataaga acgtgctctc ccaaatattc ttatttagaa aagcaaatct aaaattatct    5151
gaaaagatcg ggaatgagaa tagtgaatgg accaataata atgactagag aagaaagaat    5211
gaagattgtt catgaaatta aggaacgaat attggataaa tatggggatg atgttaaggc    5271
tattggtgtt tatggctctc ttggtcgtca gactgatggg ccctattcgg atattgagat    5331
gatgtgtgtc atgtcaacag aggaagcaga gttcagccat gaatgggaca ccggtgagtg    5391
gaaggtggaa gtgaattttg atagcgaaga gattctacta gattatgcat ctcaggtgga    5451
atcagattgg ccgcttacac atggtcaatt tttctctatt ttgccgattt atgattcagg    5511
tggatactta gagaaagtgt atcaaactgc taaatcggta gaagcccaaa cgttccacga    5571
tgcgatttgt gcccttatcg tagaagagct gtttgaatat gcaggcaaat ggcgtaatat    5631
tcgtgtgcaa ggaccgacaa catttctacc atccttgact gtacaggtag caatggcagg    5691
tgccatgttg attggtctgc atcatcgcat ctgttatacg acgagcgctt cggtcttaac    5751
```

-continued

```
tgaagcagtt aagcaatcag atcttccttc aggttatgac catctgtgcc agttcgtaat    5811
gtctggtcaa ctttccgact ctgagaaact tctggaatcg ctagagaatt tctggaatgg    5871
gattcaggag tggacagaac gacacggata tatagtggat gtgtcaaaac gcataccatt    5931
ttgaacgatg acctctaata attgttaatc atgttggtta cgtatttatt aacttctcct    5991
agtattagta attatcatgg ctgtcatggc gcattaacgg aataaagggt gtgcttaaat    6051
cgggccattt tgcgtaataa gaaaaaggat taattatgag cgaattgaat taataataag    6111
gtaatagatt tacattagaa aatgaaaggg gattttatgc gtgagaatgt tacagtctat    6171
cccggcattg ccagtcgggg atattaaaaa gagtataggt ttttattgcg ataaactagg    6231
tttcactttg gttcaccatg aagatggatt cgcagttcta atgtgtaatg aggttcggat    6291
tcatctatgg gaggcaagtg atgaaggctg gcgctctcgt agtaatgatt caccggtttg    6351
tacaggtgcg gagtcgttta ttgctggtac tgctagttgc cgcattgaag tagagggaat    6411
tgatgaatta tatcaacata ttaagccttt gggcattttg cacccaata catcattaaa     6471
agatcagtgg tgggatgaac gagactttgc agtaattgat cccgacaaca atttgattag    6531
cttttttcaa caaataaaaa gctaaaatct attattaatc tgttcagcaa tcgggcgcga    6591
ttgctgaata aagatacga gagacctctc ttgtatcttt tttatttttga gtggttttgt    6651
ccgttacact agaaaaccga agacaataa aaatttttatt cttgctgagt ctggctttcg    6711
gtaagctaga caaaacggac aaaataaaaa ttggcaaggg tttaaaggtg gagatttttt    6771
gagtgatctt ctcaaaaaat actacctgtc ccttgctgat ttttaaacga gcacgagagc    6831
aaaacccccc tttgctgagg tggcagaggg caggttttttt tgtttctttt ttctcgtaaa    6891
aaaaagaaag gtcttaaagg ttttatggtt ttggtcggca ctgccgacag cctcgcagag    6951
cacacacttt atgaatataa agtatagtgt gttatacttt acttggaagt ggttgccgga    7011
aagagcgaaa atgcctcaca tttgtgccac ctaaaaagga gcgatttaca tatgagttat    7071
gcagtttgta gaatgcaaaa agtgaaatca gctggactaa aagcatgca atttcataat    7131
caaagagagc gaaaaagtag aacgaatgat gatattgacc atgagcgaac acgtgaaaat    7191
tatgatttga aaaatgataa aaatattgat tacaacgaac gtgtcaaaga aattattgaa    7251
tcacaaaaaa caggtacaag aaaaacgagg aaagatgctg ttcttgtaaa tgagttgcta    7311
gtaacatctg accgagattt ttttgagcaa ctg                                 7344
```

<210> SEQ ID NO 17
<211> LENGTH: 967
<212> TYPE: PRT
<213> ORGANISM: Artificial Sequence

<400> SEQUENCE: 17

```
Val Leu Thr Phe His Arg Ile Ile Arg Lys Gly Trp Met Phe Leu Leu
  1               5                  10                  15

Ala Phe Leu Leu Thr Ala Ser Leu Phe Cys Pro Thr Gly Gln His Ala
             20                  25                  30

Lys Ala Ala Ala Pro Phe Asn Gly Thr Asp Gly Asn Thr Thr Asn Ile
         35                  40                  45

Val Val His Tyr Phe Arg Pro Ser Gly Asp Tyr Thr Asp Trp Asn Leu
     50                  55                  60

Trp Met Trp Pro Glu Asn Gly Asp Gly Ala Glu Tyr Asp Phe Asn Gln
 65                  70                  75                  80

Pro Thr Asp Ser Tyr Gly Glu Val Ala Ser Val Asp Ile Pro Gly Asn
```

-continued

```
                    85                  90                  95
Pro Ser Gln Val Gly Ile Ile Val Arg Lys Gly Asn Trp Asp Ala Lys
                100                 105                 110
Asp Ile Asp Ser Asp Arg Tyr Ile Asp Leu Ser Lys Gly His Glu Ile
                115                 120                 125
Trp Leu Val Gln Gly Asn Ser Gln Ile Phe Tyr Ser Glu Lys Asp Ala
            130                 135                 140
Glu Ala Ala Gln Pro Ala Val Ser Asn Ala Tyr Leu Asp Ala Ser
145                 150                 155                 160
Asn Gln Val Leu Val Lys Leu Ser Gln Pro Phe Thr Leu Gly Glu Gly
                    165                 170                 175
Ser Ser Gly Phe Thr Val His Asp Asp Thr Ala Asn Lys Asp Ile Pro
                180                 185                 190
Val Thr Ser Val Ser Asp Ala Asn Gln Val Thr Ala Val Leu Ala Gly
            195                 200                 205
Thr Phe Gln His Ile Phe Gly Gly Ser Asp Trp Ala Pro Asp Asn His
        210                 215                 220
Asn Thr Leu Leu Lys Lys Val Asn Ser Asn Leu Tyr Gln Phe Ser Gly
225                 230                 235                 240
Asn Leu Pro Glu Gly Asn Tyr Gln Tyr Lys Val Ala Leu Asn Asp Ser
                    245                 250                 255
Trp Asn Asn Pro Ser Tyr Pro Ser Asp Asn Ile Asn Leu Thr Val Pro
                260                 265                 270
Ala Gly Gly Ala His Val Thr Phe Ser Tyr Ile Pro Ser Thr His Ala
            275                 280                 285
Val Tyr Asp Thr Ile Asn Asn Pro Asn Ala Asp Leu Gln Val Asp Ser
        290                 295                 300
Ser Gly Val Lys Thr Asp Leu Val Ala Val Thr Leu Gly Glu Asn Pro
305                 310                 315                 320
Asp Val Ser His Thr Leu Ser Ile Gln Thr Glu Asp Tyr Gln Ala Gly
                    325                 330                 335
Gln Val Ile Pro Arg Lys Val Leu Asp Ser Ser Gln Tyr Tyr Tyr Ser
                340                 345                 350
Gly Asp Asp Leu Gly Asn Thr Tyr Thr Lys Asn Ala Thr Thr Phe Lys
            355                 360                 365
Val Trp Ala Pro Thr Ser Thr Gln Val Asn Val Leu Leu Tyr Asn Ser
        370                 375                 380
Ala Thr Gly Ala Val Thr Lys Thr Val Pro Met Thr Ala Ser Gly His
385                 390                 395                 400
Gly Val Trp Glu Ala Thr Val Asn Gln Asp Leu Glu Asn Trp Tyr Tyr
                    405                 410                 415
Met Tyr Glu Val Thr Gly Gln Gly Ser Thr Arg Thr Ala Val Asp Pro
                420                 425                 430
Tyr Ala Thr Ala Ile Ala Pro Asn Gly Thr Arg Gly Met Ile Val Asp
            435                 440                 445
Leu Ala Lys Thr Asp Pro Ala Gly Trp Glu Ser Asp Lys His Ile Thr
        450                 455                 460
Pro Lys Asn Ile Glu Asp Glu Val Ile Tyr Glu Met Asp Val Arg Asp
465                 470                 475                 480
Phe Ser Ile Asp Ser Asn Ser Gly Met Lys Asn Lys Gly Lys Tyr Leu
                    485                 490                 495
Ala Leu Thr Glu Lys Gly Thr Lys Gly Pro Asp Asn Val Lys Thr Gly
                500                 505                 510
```

-continued

```
Val Asp Ser Leu Lys Gln Leu Gly Ile Thr His Val Gln Leu Gln Pro
        515                 520                 525

Val Phe Ala Phe Asn Ser Val Asn Glu Asn Asp Pro Thr Gln Tyr Asn
        530                 535                 540

Trp Gly Tyr Asp Pro Arg Asn Tyr Asn Val Pro Glu Gly Gln Tyr Ala
545                 550                 555                 560

Thr Asn Ala Asn Gly Thr Thr Arg Ile Lys Glu Phe Lys Glu Met Val
                565                 570                 575

Leu Ser Leu His Gln Asp His Ile Gly Val Asn Met Asp Val Val Tyr
                580                 585                 590

Asn His Thr Phe Ala Thr Gln Ile Ser Asp Phe Asp Lys Ile Val Pro
                595                 600                 605

Glu Tyr Tyr Arg Thr Asp Asp Ala Gly Asn Tyr Thr Asn Gly Ser
        610                 615                 620

Gly Thr Gly Asn Glu Ile Ala Ala Glu Arg Pro Met Val Gln Lys Phe
625                 630                 635                 640

Ile Ile Asp Ser Leu Lys Phe Trp Val Asn Glu Tyr His Val Asp Gly
                645                 650                 655

Phe Arg Phe Asp Leu Met Ala Leu Leu Gly Lys Asp Thr Met Ser Lys
                660                 665                 670

Ala Ala Thr Gln Leu His Ala Ile Asp Pro Gly Ile Ala Leu Tyr Gly
                675                 680                 685

Glu Pro Trp Thr Gly Gly Thr Ser Ala Leu Pro Ala Asp Gln Leu Leu
        690                 695                 700

Thr Lys Gly Ala Gln Lys Gly Met Gly Val Ala Val Phe Asn Asp Asn
705                 710                 715                 720

Leu Arg Asn Gly Leu Asp Gly Ser Val Phe Asp Ser Ser Ala Gln Gly
                725                 730                 735

Phe Ala Thr Gly Ala Thr Gly Leu Thr Asp Ala Ile Lys Asn Gly Val
                740                 745                 750

Glu Gly Ser Ile Asn Asp Phe Thr Ala Ser Pro Gly Glu Thr Ile Asn
        755                 760                 765

Tyr Val Thr Ser His Asp Asn Tyr Thr Leu Trp Asp Lys Ile Ala Gln
        770                 775                 780

Ser Asn Pro Asn Asp Ser Glu Ala Asp Arg Ile Lys Met Asp Glu Leu
785                 790                 795                 800

Ala Gln Ala Ile Val Met Thr Ser Gln Gly Ile Pro Phe Met Gln Gly
                805                 810                 815

Gly Glu Glu Met Leu Arg Thr Lys Gly Gly Asn Asp Asn Ser Tyr Asn
                820                 825                 830

Ala Gly Asp Val Val Asn Glu Phe Asp Trp Ser Arg Lys Ala Gln Tyr
                835                 840                 845

Pro Asp Val Phe Asn Tyr Tyr Ser Gly Leu Ile His Leu Arg Leu Asp
        850                 855                 860

His Pro Ala Phe Arg Met Thr Thr Ala Asn Glu Ile Asn Ser His Leu
865                 870                 875                 880

Gln Phe Leu Asn Ser Pro Glu Asn Thr Val Ala Tyr Glu Leu Ser Asp
                885                 890                 895

His Ala Asn Lys Asp Thr Trp Gly Asn Ile Val Ile Tyr Asn Pro
                900                 905                 910

Asn Lys Thr Ala Glu Thr Ile Asn Leu Pro Ser Gly Lys Trp Glu Ile
        915                 920                 925
```

-continued

```
Asn Ala Thr Ser Gly Lys Val Gly Glu Ser Thr Leu Gly Gln Ala Glu
            930                 935                 940

Gly Ser Val Gln Val Pro Gly Ile Ser Met Met Ile Leu His Gln Glu
945                 950                 955                 960

Val Ser Pro Ser Asp Gly Lys
                965

<210> SEQ ID NO 18
<211> LENGTH: 2799
<212> TYPE: DNA
<213> ORGANISM: Artificial Sequence
<220> FEATURE:
<223> OTHER INFORMATION: Description of Artificial Sequence: expressed
      pullulanase
<220> FEATURE:
<221> NAME/KEY: CDS
<222> LOCATION: (1)..(2799)

<400> SEQUENCE: 18 gcc gca ccg ttt aac ggt acc gat ggg aac acc aca aac atc gta gtc      48
Ala Ala Pro Phe Asn Gly Thr Asp Gly Asn Thr Thr Asn Ile Val Val
  1               5                  10                  15 cat tat ttt cgt cct agt ggg gat tat acg gat tgg aat ctt tgg atg      96
His Tyr Phe Arg Pro Ser Gly Asp Tyr Thr Asp Trp Asn Leu Trp Met
                 20                  25                  30 tgg ccg gag aac ggt gat ggg gct gag tat gat ttt aat caa ccg act     144
Trp Pro Glu Asn Gly Asp Gly Ala Glu Tyr Asp Phe Asn Gln Pro Thr
             35                  40                  45 gat tct tat ggg gag gtt gca agt gtg gac att cct gga aac cca agt     192
Asp Ser Tyr Gly Glu Val Ala Ser Val Asp Ile Pro Gly Asn Pro Ser
         50                  55                  60 caa gta ggg att att gtc cgt aaa gga aat tgg gat gcg aaa gac att     240
Gln Val Gly Ile Ile Val Arg Lys Gly Asn Trp Asp Ala Lys Asp Ile
     65                  70                  75                  80 gat agt gac cgc tac atc gat tta agc aaa ggg cat gag att tgg ctc     288
Asp Ser Asp Arg Tyr Ile Asp Leu Ser Lys Gly His Glu Ile Trp Leu
                 85                  90                  95 gtc caa gga aac agc cag att ttc tat agt gaa aag gat gct gag gca     336
Val Gln Gly Asn Ser Gln Ile Phe Tyr Ser Glu Lys Asp Ala Glu Ala
                100                 105                 110 gcc gca caa cct gct gta agt aac gct tat tta gat gct tcc aac caa     384
Ala Ala Gln Pro Ala Val Ser Asn Ala Tyr Leu Asp Ala Ser Asn Gln
            115                 120                 125 gtg ttg gtc aag ctt agc cag ccg ttt act ctt ggt gaa ggt tca agc     432
Val Leu Val Lys Leu Ser Gln Pro Phe Thr Leu Gly Glu Gly Ser Ser
        130                 135                 140 ggt ttt acg gtt cat gat gac aca gca aat aag gat att cca gtt aca     480
Gly Phe Thr Val His Asp Asp Thr Ala Asn Lys Asp Ile Pro Val Thr
145                 150                 155                 160 tct gtt agt gat gcc aat cag gta acg gct gtt tta gca ggt act ttc     528
Ser Val Ser Asp Ala Asn Gln Val Thr Ala Val Leu Ala Gly Thr Phe
                165                 170                 175 cag cat att ttt ggg ggt agt gat tgg gca ccg gat aat cac aat act     576
Gln His Ile Phe Gly Gly Ser Asp Trp Ala Pro Asp Asn His Asn Thr
            180                 185                 190 tta cta aaa aag gtg aat agc aat ctc tat caa ttt tca gga aat ctt     624
Leu Leu Lys Lys Val Asn Ser Asn Leu Tyr Gln Phe Ser Gly Asn Leu
        195                 200                 205 cct gaa gga aac tac caa tat aaa gtg gct tta aat gat agc tgg aat     672
Pro Glu Gly Asn Tyr Gln Tyr Lys Val Ala Leu Asn Asp Ser Trp Asn
    210                 215                 220
```

```
aat ccg agc tac cca tct gat aac att aat ttg aca gtg cca gct ggt        720
Asn Pro Ser Tyr Pro Ser Asp Asn Ile Asn Leu Thr Val Pro Ala Gly
225             230                 235                 240 ggt gcc cat gtt aca ttt tct tat ata cca tcc acc cat gct gtt tat        768
Gly Ala His Val Thr Phe Ser Tyr Ile Pro Ser Thr His Ala Val Tyr
                245                 250                 255 gac acg att aac aat cct aat gcg gat tta caa gta gat agc agc ggt        816
Asp Thr Ile Asn Asn Pro Asn Ala Asp Leu Gln Val Asp Ser Ser Gly
            260                 265                 270 gtt aag acg gat ctc gtg gcg gtt act ctt gga gaa aat cct gat gta        864
Val Lys Thr Asp Leu Val Ala Val Thr Leu Gly Glu Asn Pro Asp Val
        275                 280                 285 agc cat acc ctg tcc att caa aca gag gac tat cag gca gga cag gtc        912
Ser His Thr Leu Ser Ile Gln Thr Glu Asp Tyr Gln Ala Gly Gln Val
    290                 295                 300 ata cct cgt aag gtg ctt gat tca tcc cag tac tac tat tcc gga gat        960
Ile Pro Arg Lys Val Leu Asp Ser Ser Gln Tyr Tyr Tyr Ser Gly Asp
305                 310                 315                 320 gat ctc ggg aat acc tat aca aag aat gca act acc ttt aag gtc tgg       1008
Asp Leu Gly Asn Thr Tyr Thr Lys Asn Ala Thr Thr Phe Lys Val Trp
                325                 330                 335 gcg cct aca tcc act caa gta aat gtc ctt ctt tat aat agt gca acc       1056
Ala Pro Thr Ser Thr Gln Val Asn Val Leu Leu Tyr Asn Ser Ala Thr
            340                 345                 350 ggc gcg gta act aaa acg gtt cca atg acc gca tca ggc cat ggt gta       1104
Gly Ala Val Thr Lys Thr Val Pro Met Thr Ala Ser Gly His Gly Val
        355                 360                 365 tgg gaa gca aca gtc aac caa gac ctt gaa aat tgg tat tac atg tat       1152
Trp Glu Ala Thr Val Asn Gln Asp Leu Glu Asn Trp Tyr Tyr Met Tyr
    370                 375                 380 gag gta aca gga caa ggc tca acc cga acg gct gtt gat ccg tat gca       1200
Glu Val Thr Gly Gln Gly Ser Thr Arg Thr Ala Val Asp Pro Tyr Ala
385                 390                 395                 400 aca gct att gca cca aac gga acg aga ggc atg att gtg gac cta gcc       1248
Thr Ala Ile Ala Pro Asn Gly Thr Arg Gly Met Ile Val Asp Leu Ala
                405                 410                 415 aaa aca gac ccg gcc gga tgg gag agt gac aaa cat att acg cca aag       1296
Lys Thr Asp Pro Ala Gly Trp Glu Ser Asp Lys His Ile Thr Pro Lys
            420                 425                 430 aat ata gaa gat gaa gtc atc tat gaa atg gat gtt cgt gac ttt tcc       1344
Asn Ile Glu Asp Glu Val Ile Tyr Glu Met Asp Val Arg Asp Phe Ser
        435                 440                 445 atc gac tct aat tcg ggt atg aaa aat aaa gga aag tat ttg gca ctt       1392
Ile Asp Ser Asn Ser Gly Met Lys Asn Lys Gly Lys Tyr Leu Ala Leu
    450                 455                 460 aca gaa aaa gga act aaa ggc cct gac aat gta aag aca ggg gta gat       1440
Thr Glu Lys Gly Thr Lys Gly Pro Asp Asn Val Lys Thr Gly Val Asp
465                 470                 475                 480 tcc tta aaa caa ctt ggg att act cat gtt cag ctt cag cct gtt ttc       1488
Ser Leu Lys Gln Leu Gly Ile Thr His Val Gln Leu Gln Pro Val Phe
                485                 490                 495 gca ttt aat agt gtc aat gaa aac gat cca act caa tat aat tgg ggt       1536
Ala Phe Asn Ser Val Asn Glu Asn Asp Pro Thr Gln Tyr Asn Trp Gly
            500                 505                 510 tat gac cct cgc aac tac aat gtt cct gag gga caa tat gct act aat       1584
Tyr Asp Pro Arg Asn Tyr Asn Val Pro Glu Gly Gln Tyr Ala Thr Asn
        515                 520                 525 gca aac gga aca act cgg att aaa gag ttt aag gaa atg gtt ctt tca       1632
Ala Asn Gly Thr Thr Arg Ile Lys Glu Phe Lys Glu Met Val Leu Ser
    530                 535                 540
```

```
ctc cat cag gac cac att ggg gtt aat atg gat gtt gtt tat aat cat    1680
Leu His Gln Asp His Ile Gly Val Asn Met Asp Val Val Tyr Asn His
545             550                 555                 560 acc ttt gcc acg caa atc tct gac ttc gat aag att gtg cca gaa tat    1728
Thr Phe Ala Thr Gln Ile Ser Asp Phe Asp Lys Ile Val Pro Glu Tyr
                565                 570                 575 tac tac cgc acg gat gat gct ggt aac tac act aac ggc tca ggt act    1776
Tyr Tyr Arg Thr Asp Asp Ala Gly Asn Tyr Thr Asn Gly Ser Gly Thr
            580                 585                 590 gga aac gaa atc gca gcc gaa aga cca atg gtt caa aaa ttt att atc    1824
Gly Asn Glu Ile Ala Ala Glu Arg Pro Met Val Gln Lys Phe Ile Ile
        595                 600                 605 gat tca ctt aag ttt tgg gtc aat gag tac cac gtt gac ggt ttc cgt    1872
Asp Ser Leu Lys Phe Trp Val Asn Glu Tyr His Val Asp Gly Phe Arg
610                 615                 620 ttt gac tta atg gcg ttg ctt gga aaa gat aca atg tct aaa gct gcc    1920
Phe Asp Leu Met Ala Leu Leu Gly Lys Asp Thr Met Ser Lys Ala Ala
625                 630                 635                 640 acg cag ctt cat gcc att gat cca gga att gct ctc tac ggt gag cca    1968
Thr Gln Leu His Ala Ile Asp Pro Gly Ile Ala Leu Tyr Gly Glu Pro
                645                 650                 655 tgg aca gga gga aca tcc gcg ctg cca gcc gat cag ctt tta aca aaa    2016
Trp Thr Gly Gly Thr Ser Ala Leu Pro Ala Asp Gln Leu Leu Thr Lys
            660                 665                 670 gga gct caa aaa ggc atg gga gtg gct gta ttt aat gac aat ctg cga    2064
Gly Ala Gln Lys Gly Met Gly Val Ala Val Phe Asn Asp Asn Leu Arg
        675                 680                 685 aac ggt ttg gac ggc agt gtc ttt gat tca tct gct caa ggt ttt gcg    2112
Asn Gly Leu Asp Gly Ser Val Phe Asp Ser Ser Ala Gln Gly Phe Ala
690                 695                 700 aca ggt gct act ggt tta acg gat gct att aaa aat gga gtt gaa gga    2160
Thr Gly Ala Thr Gly Leu Thr Asp Ala Ile Lys Asn Gly Val Glu Gly
705                 710                 715                 720 agt att aat gac ttc acc gct tca cca ggc gag acg atc aac tat gtc    2208
Ser Ile Asn Asp Phe Thr Ala Ser Pro Gly Glu Thr Ile Asn Tyr Val
                725                 730                 735 aca agt cat gat aac tat acc ctt tgg gac aag att gcc caa agc aat    2256
Thr Ser His Asp Asn Tyr Thr Leu Trp Asp Lys Ile Ala Gln Ser Asn
            740                 745                 750 cca aac gat tct gaa gcg gat cga att aaa atg gat gag ctc gct caa    2304
Pro Asn Asp Ser Glu Ala Asp Arg Ile Lys Met Asp Glu Leu Ala Gln
        755                 760                 765 gcg atc gtc atg acc tca caa ggc att cct ttc atg cag ggc ggg gaa    2352
Ala Ile Val Met Thr Ser Gln Gly Ile Pro Phe Met Gln Gly Gly Glu
770                 775                 780 gaa atg ctt cgt acg aaa ggc ggc aac gac aat agc tat aat gct ggt    2400
Glu Met Leu Arg Thr Lys Gly Gly Asn Asp Asn Ser Tyr Asn Ala Gly
785                 790                 795                 800 gat gta gtg aac gag ttt gat tgg agc aga aaa gct caa tat cca gat    2448
Asp Val Val Asn Glu Phe Asp Trp Ser Arg Lys Ala Gln Tyr Pro Asp
                805                 810                 815 gtt ttc aat tat tat agc ggg ctg att cat ctt cgt ctt gat cac cca    2496
Val Phe Asn Tyr Tyr Ser Gly Leu Ile His Leu Arg Leu Asp His Pro
            820                 825                 830 gcc ttc cgc atg acg aca gct aat gaa atc aat agc cac ctc caa ttc    2544
Ala Phe Arg Met Thr Thr Ala Asn Glu Ile Asn Ser His Leu Gln Phe
        835                 840                 845 cta aat agc cca gag aac aca gtg gcc tat gaa tta tct gat cat gca    2592
Leu Asn Ser Pro Glu Asn Thr Val Ala Tyr Glu Leu Ser Asp His Ala
```

```
                850                 855                 860
aat aaa gat aca tgg ggt aat att gtg gtt att tat aat cca aat aaa      2640
Asn Lys Asp Thr Trp Gly Asn Ile Val Val Ile Tyr Asn Pro Asn Lys
865                 870                 875                 880 acg gca gaa acc att aat ttg cca agc ggg aaa tgg gaa atc aat gcg      2688
Thr Ala Glu Thr Ile Asn Leu Pro Ser Gly Lys Trp Glu Ile Asn Ala
                885                 890                 895 acg agc ggt aag gtg gga gaa tcc aca ctt ggt caa gca gag ggc agt      2736
Thr Ser Gly Lys Val Gly Glu Ser Thr Leu Gly Gln Ala Glu Gly Ser
900                 905                 910 gtt caa gtt cca ggc ata tct atg atg att ctt cat caa gaa gta agc      2784
Val Gln Val Pro Gly Ile Ser Met Met Ile Leu His Gln Glu Val Ser
        915                 920                 925 cca tct gat ggt aaa                                                  2799
Pro Ser Asp Gly Lys
930

<210> SEQ ID NO 19
<211> LENGTH: 933
<212> TYPE: PRT
<213> ORGANISM: Artificial Sequence

<400> SEQUENCE: 19

Ala Ala Pro Phe Asn Gly Thr Asp Gly Asn Thr Thr Asn Ile Val Val
 1               5                  10                  15

His Tyr Phe Arg Pro Ser Gly Asp Tyr Thr Asp Trp Asn Leu Trp Met
            20                  25                  30

Trp Pro Glu Asn Gly Asp Gly Ala Glu Tyr Asp Phe Asn Gln Pro Thr
        35                  40                  45

Asp Ser Tyr Gly Glu Val Ala Ser Val Asp Ile Pro Gly Asn Pro Ser
    50                  55                  60

Gln Val Gly Ile Ile Val Arg Lys Gly Asn Trp Asp Ala Lys Asp Ile
65                  70                  75                  80

Asp Ser Asp Arg Tyr Ile Asp Leu Ser Lys Gly His Glu Ile Trp Leu
                85                  90                  95

Val Gln Gly Asn Ser Gln Ile Phe Tyr Ser Glu Lys Asp Ala Glu Ala
            100                 105                 110

Ala Ala Gln Pro Ala Val Ser Asn Ala Tyr Leu Asp Ala Ser Asn Gln
        115                 120                 125

Val Leu Val Lys Leu Ser Gln Pro Phe Thr Leu Gly Glu Gly Ser Ser
    130                 135                 140

Gly Phe Thr Val His Asp Asp Thr Ala Asn Lys Asp Ile Pro Val Thr
145                 150                 155                 160

Ser Val Ser Asp Ala Asn Gln Val Thr Ala Val Leu Ala Gly Thr Phe
                165                 170                 175

Gln His Ile Phe Gly Gly Ser Asp Trp Ala Pro Asp Asn His Asn Thr
            180                 185                 190

Leu Leu Lys Lys Val Asn Ser Asn Leu Tyr Gln Phe Ser Gly Asn Leu
        195                 200                 205

Pro Glu Gly Asn Tyr Gln Tyr Lys Val Ala Leu Asn Asp Ser Trp Asn
    210                 215                 220

Asn Pro Ser Tyr Pro Ser Asp Asn Ile Asn Leu Thr Val Pro Ala Gly
225                 230                 235                 240

Gly Ala His Val Thr Phe Ser Tyr Ile Pro Ser Thr His Ala Val Tyr
                245                 250                 255

Asp Thr Ile Asn Asn Pro Asn Ala Asp Leu Gln Val Asp Ser Ser Gly
```

-continued

```
                    260                 265                 270
Val Lys Thr Asp Leu Val Ala Val Thr Leu Gly Glu Asn Pro Asp Val
            275                 280                 285
Ser His Thr Leu Ser Ile Gln Thr Glu Asp Tyr Gln Ala Gly Gln Val
            290                 295                 300
Ile Pro Arg Lys Val Leu Asp Ser Ser Gln Tyr Tyr Ser Gly Asp
305                 310                 315                 320
Asp Leu Gly Asn Thr Tyr Thr Lys Asn Ala Thr Thr Phe Lys Val Trp
                    325                 330                 335
Ala Pro Thr Ser Thr Gln Val Asn Val Leu Leu Tyr Asn Ser Ala Thr
                    340                 345                 350
Gly Ala Val Thr Lys Thr Val Pro Met Thr Ala Ser Gly His Gly Val
            355                 360                 365
Trp Glu Ala Thr Val Asn Gln Asp Leu Glu Asn Trp Tyr Tyr Met Tyr
            370                 375                 380
Glu Val Thr Gly Gln Gly Ser Thr Arg Thr Ala Val Asp Pro Tyr Ala
385                 390                 395                 400
Thr Ala Ile Ala Pro Asn Gly Thr Arg Gly Met Ile Val Asp Leu Ala
                    405                 410                 415
Lys Thr Asp Pro Ala Gly Trp Glu Ser Asp Lys His Ile Thr Pro Lys
                    420                 425                 430
Asn Ile Glu Asp Glu Val Ile Tyr Glu Met Asp Val Arg Asp Phe Ser
                    435                 440                 445
Ile Asp Ser Asn Ser Gly Met Lys Asn Lys Gly Lys Tyr Leu Ala Leu
            450                 455                 460
Thr Glu Lys Gly Thr Lys Gly Pro Asp Asn Val Lys Thr Gly Val Asp
465                 470                 475                 480
Ser Leu Lys Gln Leu Gly Ile Thr His Val Gln Leu Gln Pro Val Phe
                    485                 490                 495
Ala Phe Asn Ser Val Asn Glu Asn Asp Pro Thr Gln Tyr Asn Trp Gly
                    500                 505                 510
Tyr Asp Pro Arg Asn Tyr Asn Val Pro Glu Gly Gln Tyr Ala Thr Asn
            515                 520                 525
Ala Asn Gly Thr Thr Arg Ile Lys Glu Phe Lys Glu Met Val Leu Ser
            530                 535                 540
Leu His Gln Asp His Ile Gly Val Asn Met Asp Val Val Tyr Asn His
545                 550                 555                 560
Thr Phe Ala Thr Gln Ile Ser Asp Phe Asp Lys Ile Val Pro Glu Tyr
                    565                 570                 575
Tyr Tyr Arg Thr Asp Asp Ala Gly Asn Tyr Thr Asn Gly Ser Gly Thr
                    580                 585                 590
Gly Asn Glu Ile Ala Ala Glu Arg Pro Met Val Gln Lys Phe Ile Ile
            595                 600                 605
Asp Ser Leu Lys Phe Trp Val Asn Glu Tyr His Val Asp Gly Phe Arg
610                 615                 620
Phe Asp Leu Met Ala Leu Leu Gly Lys Asp Thr Met Ser Lys Ala Ala
625                 630                 635                 640
Thr Gln Leu His Ala Ile Asp Pro Gly Ile Ala Leu Tyr Gly Glu Pro
                    645                 650                 655
Trp Thr Gly Gly Thr Ser Ala Leu Pro Ala Asp Gln Leu Leu Thr Lys
            660                 665                 670
Gly Ala Gln Lys Gly Met Gly Val Ala Val Phe Asn Asp Asn Leu Arg
            675                 680                 685
```

Asn Gly Leu Asp Gly Ser Val Phe Asp Ser Ser Ala Gln Gly Phe Ala
    690                 695                 700
Thr Gly Ala Thr Gly Leu Thr Asp Ala Ile Lys Asn Gly Val Glu Gly
705                 710                 715                 720
Ser Ile Asn Asp Phe Thr Ala Ser Pro Gly Glu Thr Ile Asn Tyr Val
                725                 730                 735
Thr Ser His Asp Asn Tyr Thr Leu Trp Asp Lys Ile Ala Gln Ser Asn
                740                 745                 750
Pro Asn Asp Ser Glu Ala Asp Arg Ile Lys Met Asp Glu Leu Ala Gln
            755                 760                 765
Ala Ile Val Met Thr Ser Gln Gly Ile Pro Phe Met Gln Gly Gly Glu
770                 775                 780
Glu Met Leu Arg Thr Lys Gly Gly Asn Asp Asn Ser Tyr Asn Ala Gly
785                 790                 795                 800
Asp Val Val Asn Glu Phe Asp Trp Ser Arg Lys Ala Gln Tyr Pro Asp
                805                 810                 815
Val Phe Asn Tyr Tyr Ser Gly Leu Ile His Leu Arg Leu Asp His Pro
            820                 825                 830
Ala Phe Arg Met Thr Thr Ala Asn Glu Ile Asn Ser His Leu Gln Phe
835                 840                 845
Leu Asn Ser Pro Glu Asn Thr Val Ala Tyr Glu Leu Ser Asp His Ala
850                 855                 860
Asn Lys Asp Thr Trp Gly Asn Ile Val Val Ile Tyr Asn Pro Asn Lys
865                 870                 875                 880
Thr Ala Glu Thr Ile Asn Leu Pro Ser Gly Lys Trp Glu Ile Asn Ala
                885                 890                 895
Thr Ser Gly Lys Val Gly Glu Ser Thr Leu Gly Gln Ala Glu Gly Ser
            900                 905                 910
Val Gln Val Pro Gly Ile Ser Met Met Ile Leu His Gln Glu Val Ser
        915                 920                 925
Pro Ser Asp Gly Lys
    930

<210> SEQ ID NO 20
<211> LENGTH: 7026
<212> TYPE: DNA
<213> ORGANISM: Artificial Sequence
<220> FEATURE:
<223> OTHER INFORMATION: Description of Artificial Sequence:pEB303
<220> FEATURE:
<221> NAME/KEY: CDS
<222> LOCATION: (484)..(2943)

<400> SEQUENCE: 20

| | | | | | |
|---|---|---|---|---|---|
| gatcatcccc | cgctcccttc | tcctttgttt | ggccaacttc | cttctctcct | ttccttttta | 60 |
| tattctttgt | gcaatcgttt | gcacaaaacg | gttgatgcaa | acgatttcat | caataaacag | 120 |
| aatatttcaa | ctatattttc | cacttgttga | aaaacgaatc | gttctgttgt | tctattttcg | 180 |
| attcgtgtca | aactcaaaat | tgtttaaatt | cgatattgaa | aacgattaca | aataaaaatt | 240 |
| ataatagacg | taaacgttcg | agggtttgct | ccctttttac | tcttttttatg | caatcgtttc | 300 |
| ccttaatttt | ttggaagcca | aaccgtcgaa | tgtaacattt | gattaagggg | gaagggcatt | 360 |
| gtgctaacgt | ttcaccgcat | cattcgaaaa | ggatggatgt | tcctgctcgc | gttttttgctc | 420 |
| actgcctcgc | tgttctgccc | aacaggacag | cacgccaagg | ctgccgcacc | gtttaacggt | 480 |
| acc gca caa cct gct gta agt aac gct tat tta gat gct tcc aac caa | | | | | | 528 |

```
        Ala Gln Pro Ala Val Ser Asn Ala Tyr Leu Asp Ala Ser Asn Gln
         1               5                  10                  15 gtg ttg gtc aag ctt agc cag ccg ttt act ctt ggt gaa ggt tca agc        576
Val Leu Val Lys Leu Ser Gln Pro Phe Thr Leu Gly Glu Gly Ser Ser
             20                  25                  30 ggt ttt acg gtt cat gat gac aca gca aat aag gat att cca gtt aca        624
Gly Phe Thr Val His Asp Asp Thr Ala Asn Lys Asp Ile Pro Val Thr
         35                  40                  45 tct gtt agt gat gcc aat cag gta acg gct gtt tta gca ggt act ttc        672
Ser Val Ser Asp Ala Asn Gln Val Thr Ala Val Leu Ala Gly Thr Phe
             50                  55                  60 cag cat att ttt ggg ggg agt gat tgg gca ccg gat aat cac aat act        720
Gln His Ile Phe Gly Gly Ser Asp Trp Ala Pro Asp Asn His Asn Thr
         65                  70                  75 tta cta aaa aag gtg aat agc aat ctc tat caa ttt tca gga aat ctt        768
Leu Leu Lys Lys Val Asn Ser Asn Leu Tyr Gln Phe Ser Gly Asn Leu
 80                  85                  90                  95 cct gaa gga aac tac caa tat aaa gtg gct tta aat gat agc tgg aat        816
Pro Glu Gly Asn Tyr Gln Tyr Lys Val Ala Leu Asn Asp Ser Trp Asn
                 100                 105                 110 aat ccg agc tac cca tct gat aac att aat ttg aca gtg cca gct ggt        864
Asn Pro Ser Tyr Pro Ser Asp Asn Ile Asn Leu Thr Val Pro Ala Gly
             115                 120                 125 ggt gcc cat gtt aca ttt tct tat ata cca tcc acc cat gct gtt tat        912
Gly Ala His Val Thr Phe Ser Tyr Ile Pro Ser Thr His Ala Val Tyr
         130                 135                 140 gac acg att aac aat cct aat gcg gat tta caa gta gat agc agc ggt        960
Asp Thr Ile Asn Asn Pro Asn Ala Asp Leu Gln Val Asp Ser Ser Gly
         145                 150                 155 gtt aag acg gat ctc gtg gcg gtt act ctt gga gaa aat cct gat gta       1008
Val Lys Thr Asp Leu Val Ala Val Thr Leu Gly Glu Asn Pro Asp Val
160                 165                 170                 175 agc cat acc ctg tcc att caa aca gag gac tat cag gca gga cag gtc       1056
Ser His Thr Leu Ser Ile Gln Thr Glu Asp Tyr Gln Ala Gly Gln Val
             180                 185                 190 ata cct cgt aag gtg ctt gat tca tcc cag tac tac tat tcc gga gat       1104
Ile Pro Arg Lys Val Leu Asp Ser Ser Gln Tyr Tyr Tyr Ser Gly Asp
         195                 200                 205 gat ctc ggg aat acc tat aca aag aat gca act acc ttt aag gtc tgg       1152
Asp Leu Gly Asn Thr Tyr Thr Lys Asn Ala Thr Thr Phe Lys Val Trp
         210                 215                 220 gcg cct aca tcc act caa gta aat gtc ctt ctt tat aat agt gca acc       1200
Ala Pro Thr Ser Thr Gln Val Asn Val Leu Leu Tyr Asn Ser Ala Thr
225                 230                 235 ggc gcg gta act aaa acg gtt cca atg acc gca tca ggc cat ggt gta       1248
Gly Ala Val Thr Lys Thr Val Pro Met Thr Ala Ser Gly His Gly Val
240                 245                 250                 255 tgg gaa gca aca gtc aac caa gac ctt gaa aat tgg tat tac atg tat       1296
Trp Glu Ala Thr Val Asn Gln Asp Leu Glu Asn Trp Tyr Tyr Met Tyr
             260                 265                 270 gag gta aca gga caa ggc tca acc cga acg gct gtt gat ccg tat gca       1344
Glu Val Thr Gly Gln Gly Ser Thr Arg Thr Ala Val Asp Pro Tyr Ala
         275                 280                 285 aca gct att gca cca aac gga acg aga ggc atg att gtg gac cta gcc       1392
Thr Ala Ile Ala Pro Asn Gly Thr Arg Gly Met Ile Val Asp Leu Ala
         290                 295                 300 aaa aca gac ccg gcc gga tgg gag agt gac aaa cat att acg cca aag       1440
Lys Thr Asp Pro Ala Gly Trp Glu Ser Asp Lys His Ile Thr Pro Lys
305                 310                 315
```

-continued

```
aat ata gaa gat gaa gtc atc tat gaa atg gat gtt cgt gac ttt tcc      1488
Asn Ile Glu Asp Glu Val Ile Tyr Glu Met Asp Val Arg Asp Phe Ser
320                 325                 330                 335 atc gac tct aat tcg ggt atg aaa aat aaa gga aag tat ttg gca ctt      1536
Ile Asp Ser Asn Ser Gly Met Lys Asn Lys Gly Lys Tyr Leu Ala Leu
                340                 345                 350 aca gaa aaa gga act aaa ggc cct gac aat gta aag aca ggg gta gat      1584
Thr Glu Lys Gly Thr Lys Gly Pro Asp Asn Val Lys Thr Gly Val Asp
            355                 360                 365 tcc tta aaa caa ctt ggg att act cat gtt cag ctt cag cct gtt ttc      1632
Ser Leu Lys Gln Leu Gly Ile Thr His Val Gln Leu Gln Pro Val Phe
        370                 375                 380 gca ttt aat agt gtc aat gaa aac gat cca act caa tat aat tgg ggt      1680
Ala Phe Asn Ser Val Asn Glu Asn Asp Pro Thr Gln Tyr Asn Trp Gly
385                 390                 395 tat gac cct cgc aac tac aat gtt cct gag gga caa tat gct act aat      1728
Tyr Asp Pro Arg Asn Tyr Asn Val Pro Glu Gly Gln Tyr Ala Thr Asn
400                 405                 410                 415 gca aac gga aca act cgg att aaa gag ttt aag gaa atg gtt ctt tca      1776
Ala Asn Gly Thr Thr Arg Ile Lys Glu Phe Lys Glu Met Val Leu Ser
                420                 425                 430 ctc cat cag gac cac att ggg gtt aat atg gat gtt gtt tat aat cat      1824
Leu His Gln Asp His Ile Gly Val Asn Met Asp Val Val Tyr Asn His
            435                 440                 445 acc ttt gcc acg caa atc tct gac ttc gat aag att gtg cca gaa tat      1872
Thr Phe Ala Thr Gln Ile Ser Asp Phe Asp Lys Ile Val Pro Glu Tyr
        450                 455                 460 tac tac cgc acg gat gat gct ggt aac tac act aac ggc tca ggt act      1920
Tyr Tyr Arg Thr Asp Asp Ala Gly Asn Tyr Thr Asn Gly Ser Gly Thr
465                 470                 475 gga aac gaa atc gca gcc gaa aga cca atg gtt caa aaa ttt att atc      1968
Gly Asn Glu Ile Ala Ala Glu Arg Pro Met Val Gln Lys Phe Ile Ile
480                 485                 490                 495 gat tca ctt aag ttt tgg gtc aat gag tac cac gtt gac ggt ttc cgt      2016
Asp Ser Leu Lys Phe Trp Val Asn Glu Tyr His Val Asp Gly Phe Arg
                500                 505                 510 ttt gac tta atg gcg ttg ctt gga aaa gat aca atg tct aaa gct gcc      2064
Phe Asp Leu Met Ala Leu Leu Gly Lys Asp Thr Met Ser Lys Ala Ala
            515                 520                 525 acg cag ctt cat gcc att gat cca gga att gct ctc tac ggt gag cca      2112
Thr Gln Leu His Ala Ile Asp Pro Gly Ile Ala Leu Tyr Gly Glu Pro
        530                 535                 540 tgg aca gga gga aca tcc gcg ctg cca gcc gat cag ctt tta aca aaa      2160
Trp Thr Gly Gly Thr Ser Ala Leu Pro Ala Asp Gln Leu Leu Thr Lys
545                 550                 555 gga gct caa aaa ggc atg gga gtg gct gta ttt aat gac aat ctg cga      2208
Gly Ala Gln Lys Gly Met Gly Val Ala Val Phe Asn Asp Asn Leu Arg
560                 565                 570                 575 aac ggt ttg gac ggc agt gtc ttt gat tca tct gct caa ggt ttt gcg      2256
Asn Gly Leu Asp Gly Ser Val Phe Asp Ser Ser Ala Gln Gly Phe Ala
                580                 585                 590 aca ggt gct act ggt tta acg gat gct att aaa aat gga gtt gaa gga      2304
Thr Gly Ala Thr Gly Leu Thr Asp Ala Ile Lys Asn Gly Val Glu Gly
            595                 600                 605 agt att aat gac ttc acc gct tca cca ggc gag acg atc aac tat gtc      2352
Ser Ile Asn Asp Phe Thr Ala Ser Pro Gly Glu Thr Ile Asn Tyr Val
        610                 615                 620 aca agt cat gat aac tat acc ctt tgg gac aag att gcc caa agc aat      2400
Thr Ser His Asp Asn Tyr Thr Leu Trp Asp Lys Ile Ala Gln Ser Asn
625                 630                 635
```

-continued

```
cca aac gat tct gaa gcg gat cga att aaa atg gat gag ctc gct caa    2448
Pro Asn Asp Ser Glu Ala Asp Arg Ile Lys Met Asp Glu Leu Ala Gln
640                 645                 650                 655 gcg atc gtc atg acc tca caa ggc att cct ttc atg cag ggc ggg gaa    2496
Ala Ile Val Met Thr Ser Gln Gly Ile Pro Phe Met Gln Gly Gly Glu
                660                 665                 670 gaa atg ctt cgt acg aaa ggc ggc aac gac aat agc tat aat gct ggt    2544
Glu Met Leu Arg Thr Lys Gly Gly Asn Asp Asn Ser Tyr Asn Ala Gly
            675                 680                 685 gat gta gtg aac gag ttt gat tgg agc aga aaa gct caa tat cca gat    2592
Asp Val Val Asn Glu Phe Asp Trp Ser Arg Lys Ala Gln Tyr Pro Asp
        690                 695                 700 gtt ttc aat tat tat agc ggg ctg att cat ctt cgt ctt gat cac cca    2640
Val Phe Asn Tyr Tyr Ser Gly Leu Ile His Leu Arg Leu Asp His Pro
705                 710                 715 gcc ttc cgc atg acg aca gct aat gaa atc aat agc cac ctc caa ttc    2688
Ala Phe Arg Met Thr Thr Ala Asn Glu Ile Asn Ser His Leu Gln Phe
720                 725                 730                 735 cta aat agc cca gag aac aca gtg gcc tat gaa tta tct gat cat gca    2736
Leu Asn Ser Pro Glu Asn Thr Val Ala Tyr Glu Leu Ser Asp His Ala
                740                 745                 750 aat aaa gat aca tgg ggt aat att gtg gtt att tat aat cca aat aaa    2784
Asn Lys Asp Thr Trp Gly Asn Ile Val Val Ile Tyr Asn Pro Asn Lys
            755                 760                 765 acg gca gaa acc att aat ttg cca agc ggg aaa tgg gaa atc aat gcg    2832
Thr Ala Glu Thr Ile Asn Leu Pro Ser Gly Lys Trp Glu Ile Asn Ala
        770                 775                 780 acg agc ggt aag gtg gga gaa tcc aca ctt ggt caa gca gag ggc agt    2880
Thr Ser Gly Lys Val Gly Glu Ser Thr Leu Gly Gln Ala Glu Gly Ser
    785                 790                 795 gtt caa gtt cca ggc ata tct atg atg att ctt cat caa gaa gta agc    2928
Val Gln Val Pro Gly Ile Ser Met Met Ile Leu His Gln Glu Val Ser
800                 805                 810                 815 cca tct gat ggt aaa tagaattaaa aaattgaaat cccctcaag attttttgag    2983
Pro Ser Asp Gly Lys
                820 ggggatttag tctcttctta tccaatttaa tttgcggctt cgttcttttc gatggacaac    3043
gtgttcggtc ggttgtgaga tagaaaaatt gggagtgagt aggtcacaag agcagccaat    3103
tcgcttccaa atccttcatc gacctaaatg aacttaggat ccgggctggc cgcactgatc    3163
accgatgggc cgggaggaag caaatggatg tacgttggca acaacacgc tggaaaagtg    3223
ttctatgacc ttaccggcaa ccggagtgac accgtcacca tcaacagtga tggatggggg    3283
gaattcaaag tcaatggcgg ttcggtttcg gtttgggttc ctagaaaaac gaccgttct    3343
accatcgctc ggccgatcac aacccgaccg tggactggtg aattcgtccg ttggaccgaa    3403
ccacggttgg tggcatggcc ttgatgcctg cgatcaggga atgagtttat aaaataaaaa    3463
aagcacctga aaaggtgtct ttttttgatg gttttgaact tgttctttct tatcttgata    3523
catatagaaa taacgtcatt tttattttag ttgctgaaag gtgcgttgaa gtgttggtat    3583
gtatgtgttt taaagtattg aaaacccctta aaattggttg cacagaaaaa ccccatctgt    3643
taaagttata agtgactaaa caataacta aatagatggg ggtttctttt aatattatgt    3703
gtcctaatag tagcatttat tcagatgaaa atcaagggt tttagtggac aagacaaaaa    3763
gtggaaaagt gagaccatgg agagaaaaga aaatcgctaa tgttgattac tttgaacttc    3823
tgcatattct tgaatttaaa aaggctgaaa gagtaaaaga ttgtgctgaa atattagagt    3883
```

```
ataaacaaaa tcgtgaaaca ggcgaaagaa agttgtatcg agtgtggttt tgtaaatcca   3943
ggctttgtcc aatgtgcaac tggaggagag caatgaaaca tggcattcag tcacaaaagg   4003
ttgttgctga agttattaaa caaaagccaa cagttcgttg gttgtttctc acattaacag   4063
ttaaaaatgt ttatgatggc gaagaattaa ataagagttt gtcagatatg gctcaaggat   4123
ttcgccgaat gatgcaatat aaaaaaatta ataaaaatct tgttggtttt atgcgtgcaa   4183
cggaagtgac aataataat aaagataatt cttataatca gcacatgcat gtattggtat   4243
gtgtggaacc aacttatttt aagaatacag aaaactacgt gaatcaaaaa caatggattc   4303
aattttggaa aaaggcaatg aaattagact atgatccaaa tgtaaaagtt caaatgattc   4363
gaccgaaaaa taaatataaa tcggatatac aatcggcaat tgacgaaact gcaaaatatc   4423
ctgtaaagga tacggatttt atgaccgatg atgaagaaaa gaatttgaaa cgtttgtctg   4483
atttggagga aggtttacac cgtaaaaggt taatctccta tggtggtttg ttaaaagaaa   4543
tacataaaaa attaaacctt gatgacacag aagaaggcga tttgattcat acagatgatg   4603
acgaaaaagc cgatgaagat ggattttcta ttattgcaat gtggaattgg aacggaaaa   4663 attattttat taagagtag ttcaacaaac gggccagttt gttgaagatt agatgctata   4723
attgttatta aaaggattga aggatgctta ggaagacgag ttattaatag ctgataaga   4783 acggtgctct ccaaatattc ttatttagaa aagcaaatct aaaattatct gaaaagatcg   4843
ggaatgagaa tagtgaatgg accaataata atgactagag aagaaagaat gaagattgtt   4903
catgaaatta aggaacgaat attggataaa tatggggatg atgttaaggc tattggtgtt   4963
tatggctctc ttggtcgtca gactgatggg ccctattcgg atattgagat gatgtgtgtc   5023
atgtcaacag aggaagcaga gttcagccat gaatggacaa ccggtgagtg gaaggtggaa   5083
gtgaattttg atagcgaaga gattctacta gattatgcat ctcaggtgga atcagattgg   5143
ccgcttacac atggtcaatt tttctctatt ttgccgattt atgattcagg tggatactta   5203
gagaaagtgt atcaaactgc taaatcggta gaagcccaaa cgttccacga tgcgatttgt   5263
gcccttatcg tagaagagct gtttgaatat gcaggcaaat ggcgtaatat tcgtgtgcaa   5323
ggaccgacaa catttctacc atccttgact gtacaggtag caatggcagg tgccatgttg   5383
attggtctgc atcatcgcat ctgttatacg acgagcgctt cggtcttaac tgaagcagtt   5443
aagcaatcag atcttccttc aggttatgac catctgtgcc agttcgtaat gtctggtcaa   5503
ctttccgact ctgagaaact tctggaatcg ctagagaatt tctggaatgg gattcaggag   5563
tggacagaac gacacggata tatagtggat gtgtcaaaac gcataccatt ttgaacgatg   5623
acctctaata attgttaatc atgttggtta cgtatttatt aacttctcct agtattagta   5683
attatcatgg ctgtcatggc gcattaacgg aataaagggt gtgcttaaat cgggccattt   5743
tgcgtaataa gaaaaaggat taattatgag cgaattgaat taataataag gtaatagatt   5803
tacattagaa aatgaaaggg gattttatgc gtgagaatgt tacagtctat cccggcattg   5863
ccagtcgggg atattaaaaa gagtataggt ttttattgcg ataaactagg tttcactttg   5923
gttcaccatg aagatggatt cgcagttcta atgtgtaatg aggttcggat tcatctatgg   5983
gaggcaagtg atgaaggctg gcgctctcgt agtaatgatt caccggtttg tacaggtgcg   6043 gagtcgtttta ttgctggtac tgctagttgc cgcattgaag tagagggaat tgatgaatta   6103
tatcaacata ttaagccttt gggcattttt cacccaata catcattaa agatcagtgg   6163 tgggatgaac gagactttgc agtaattgat cccgacaaca atttgattag cttttttcaa   6223 caaataaaa gctaaaatct attattaatc tgttcagcaa tcgggcgcga ttgctgaata   6283
```

-continued

```
aaagatacga gagacctctc ttgtatctttt tttattttga gtggttttgt ccgttacact    6343
agaaaaccga aagacaataa aaattttatt cttgctgagt ctggctttcg gtaagctaga    6403
caaaacggac aaaataaaaa ttggcaaggg tttaaaggtg gagatttttt gagtgatctt    6463
ctcaaaaaat actacctgtc ccttgctgat ttttaaacga gcacgagagc aaaccccccc    6523
tttgctgagg tggcagaggg caggttttt tgtttctttt ttctcgtaaa aaaagaaag     6583 gtcttaaagg ttttatggtt ttggtcggca ctgccgacag cctcgcagag cacacacttt    6643
atgaatataa agtatagtgt gttatacttt acttggaagt ggttgccgga aagagcgaaa    6703
atgcctcaca tttgtgccac ctaaaaagga gcgatttaca tatgagttat gcagtttgta    6763
gaatgcaaaa agtgaaatca gctggactaa aaggcatgca atttcataat caaagagagc    6823
gaaaaagtag aacgaatgat gatattgacc atgagcgaac acgtgaaaat tatgatttga    6883
aaaatgataa aaatattgat tacaacgaac gtgtcaaaga aattattgaa tcacaaaaaa    6943
caggtacaag aaaaacgagg aaagatgctg ttcttgtaaa tgagttgcta gtaacatctg    7003
accgagattt ttttgagcaa ctg                                            7026
```

<210> SEQ ID NO 21
<211> LENGTH: 820
<212> TYPE: PRT
<213> ORGANISM: Artificial Sequence

<400> SEQUENCE: 21

```
Ala Gln Pro Ala Val Ser Asn Ala Tyr Leu Asp Ala Ser Asn Gln Val
 1               5                  10                  15

Leu Val Lys Leu Ser Gln Pro Phe Thr Leu Gly Glu Gly Ser Ser Gly
            20                  25                  30

Phe Thr Val His Asp Asp Thr Ala Asn Lys Asp Ile Pro Val Thr Ser
        35                  40                  45

Val Ser Asp Ala Asn Gln Val Thr Ala Val Leu Ala Gly Thr Phe Gln
    50                  55                  60

His Ile Phe Gly Gly Ser Asp Trp Ala Pro Asp Asn His Asn Thr Leu
65                  70                  75                  80

Leu Lys Lys Val Asn Ser Asn Leu Tyr Gln Phe Ser Gly Asn Leu Pro
                85                  90                  95

Glu Gly Asn Tyr Gln Tyr Lys Val Ala Leu Asn Asp Ser Trp Asn Asn
            100                 105                 110

Pro Ser Tyr Pro Ser Asp Asn Ile Asn Leu Thr Val Pro Ala Gly Gly
        115                 120                 125

Ala His Val Thr Phe Ser Tyr Ile Pro Ser Thr His Ala Val Tyr Asp
    130                 135                 140

Thr Ile Asn Asn Pro Asn Ala Asp Leu Gln Val Asp Ser Ser Gly Val
145                 150                 155                 160

Lys Thr Asp Leu Val Ala Val Thr Leu Gly Glu Asn Pro Asp Val Ser
                165                 170                 175

His Thr Leu Ser Ile Gln Thr Glu Asp Tyr Gln Ala Gly Gln Val Ile
            180                 185                 190

Pro Arg Lys Val Leu Asp Ser Ser Gln Tyr Tyr Ser Gly Asp Asp
        195                 200                 205

Leu Gly Asn Thr Tyr Thr Lys Asn Ala Thr Thr Phe Lys Val Trp Ala
    210                 215                 220

Pro Thr Ser Thr Gln Val Asn Val Leu Leu Tyr Asn Ser Ala Thr Gly
225                 230                 235                 240
```

```
Ala Val Thr Lys Thr Val Pro Met Thr Ala Ser Gly His Gly Val Trp
            245                 250                 255

Glu Ala Thr Val Asn Gln Asp Leu Glu Asn Trp Tyr Tyr Met Tyr Glu
            260                 265                 270

Val Thr Gly Gln Gly Ser Thr Arg Thr Ala Val Asp Pro Tyr Ala Thr
            275                 280                 285

Ala Ile Ala Pro Asn Gly Thr Arg Gly Met Ile Val Asp Leu Ala Lys
            290                 295                 300

Thr Asp Pro Ala Gly Trp Glu Ser Asp Lys His Ile Thr Pro Lys Asn
305                 310                 315                 320

Ile Glu Asp Glu Val Ile Tyr Glu Met Asp Val Arg Asp Phe Ser Ile
                325                 330                 335

Asp Ser Asn Ser Gly Met Lys Asn Lys Gly Lys Tyr Leu Ala Leu Thr
                340                 345                 350

Glu Lys Gly Thr Lys Gly Pro Asp Asn Val Lys Thr Gly Val Asp Ser
            355                 360                 365

Leu Lys Gln Leu Gly Ile Thr His Val Gln Leu Gln Pro Val Phe Ala
            370                 375                 380

Phe Asn Ser Val Asn Glu Asn Asp Pro Thr Gln Tyr Asn Trp Gly Tyr
385                 390                 395                 400

Asp Pro Arg Asn Tyr Asn Val Pro Glu Gly Gln Tyr Ala Thr Asn Ala
                405                 410                 415

Asn Gly Thr Thr Arg Ile Lys Glu Phe Lys Glu Met Val Leu Ser Leu
            420                 425                 430

His Gln Asp His Ile Gly Val Asn Met Asp Val Val Tyr Asn His Thr
            435                 440                 445

Phe Ala Thr Gln Ile Ser Asp Phe Asp Lys Ile Val Pro Glu Tyr Tyr
            450                 455                 460

Tyr Arg Thr Asp Asp Ala Gly Asn Tyr Thr Asn Gly Ser Gly Thr Gly
465                 470                 475                 480

Asn Glu Ile Ala Ala Glu Arg Pro Met Val Gln Lys Phe Ile Ile Asp
                485                 490                 495

Ser Leu Lys Phe Trp Val Asn Glu Tyr His Val Asp Gly Phe Arg Phe
            500                 505                 510

Asp Leu Met Ala Leu Leu Gly Lys Asp Thr Met Ser Lys Ala Ala Thr
            515                 520                 525

Gln Leu His Ala Ile Asp Pro Gly Ile Ala Leu Tyr Gly Glu Pro Trp
            530                 535                 540

Thr Gly Gly Thr Ser Ala Leu Pro Ala Asp Gln Leu Leu Thr Lys Gly
545                 550                 555                 560

Ala Gln Lys Gly Met Gly Val Ala Val Phe Asn Asp Asn Leu Arg Asn
            565                 570                 575

Gly Leu Asp Gly Ser Val Phe Asp Ser Ser Ala Gln Gly Phe Ala Thr
            580                 585                 590

Gly Ala Thr Gly Leu Thr Asp Ala Ile Lys Asn Gly Val Glu Gly Ser
            595                 600                 605

Ile Asn Asp Phe Thr Ala Ser Pro Gly Glu Thr Ile Asn Tyr Val Thr
            610                 615                 620

Ser His Asp Asn Tyr Thr Leu Trp Asp Lys Ile Ala Gln Ser Asn Pro
625                 630                 635                 640

Asn Asp Ser Glu Ala Asp Arg Ile Lys Met Asp Glu Leu Ala Gln Ala
                645                 650                 655
```

```
Ile Val Met Thr Ser Gln Gly Ile Pro Phe Met Gln Gly Gly Glu Glu
            660             665             670

Met Leu Arg Thr Lys Gly Gly Asn Asp Asn Ser Tyr Asn Ala Gly Asp
            675             680             685

Val Val Asn Glu Phe Asp Trp Ser Arg Lys Ala Gln Tyr Pro Asp Val
    690             695             700

Phe Asn Tyr Tyr Ser Gly Leu Ile His Leu Arg Leu Asp His Pro Ala
705             710             715             720

Phe Arg Met Thr Thr Ala Asn Glu Ile Asn Ser His Leu Gln Phe Leu
            725             730             735

Asn Ser Pro Glu Asn Thr Val Ala Tyr Glu Leu Ser Asp His Ala Asn
            740             745             750

Lys Asp Thr Trp Gly Asn Ile Val Val Ile Tyr Asn Pro Asn Lys Thr
            755             760             765

Ala Glu Thr Ile Asn Leu Pro Ser Gly Lys Trp Glu Ile Asn Ala Thr
    770             775             780

Ser Gly Lys Val Gly Glu Ser Thr Leu Gly Gln Ala Glu Gly Ser Val
785             790             795             800

Gln Val Pro Gly Ile Ser Met Met Ile Leu His Gln Glu Val Ser Pro
            805             810             815

Ser Asp Gly Lys
            820

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 22
gggggtaccg cacaacctgc tgtaagtaac gc                              32
```